US012617793B2

(12) United States Patent
Shin et al.

(10) Patent No.: US 12,617,793 B2

(45) Date of Patent: May 5, 2026

(54) ORGANIC ELECTRON TRANSFER MEDIATOR AND DEVICE COMPRISING SAME

(71) Applicants: I-sens, Inc., Seoul (KR); SOGANG UNIVERSITY RESEARCH & BUSINESS DEVELOPMENT FOUNDATION, Seoul (KR)

(72) Inventors: Hyunseo Shin, Seoul (KR); Young Jea Kang, Seoul (KR); Seok-Won Lee, Seoul (KR); Bongjin Moon, Seoul (KR); Myeonghwa Jeong, Seoul (KR); Sangeun Yoon, Seoul (KR)

(73) Assignees: I-SENS, INC., Seoul (KR); SOGANG UNIVERSITY RESEARCH & BUSINESS DEVELOPMENT FOUNDATION, Seoul (KR)

( * ) Notice: Subject to any disclaimer, the term of this patent is extended or adjusted under 35 U.S.C. 154(b) by 850 days.

(21) Appl. No.: 17/787,389

(22) PCT Filed: Dec. 28, 2020

(86) PCT No.: PCT/KR2020/019228

§ 371 (c)(1),
(2) Date: Jun. 20, 2022

(87) PCT Pub. No.: WO2021/133144

PCT Pub. Date: Jul. 1, 2021

(65) Prior Publication Data

US 2023/0102721 A1 Mar. 30, 2023

(30) Foreign Application Priority Data

Dec. 26, 2019 (KR) ........................ 10-2019-0175535

(51) Int. Cl.

*C07D 475/12* (2006.01)
*C12Q 1/00* (2006.01)
*C12Q 1/26* (2006.01)

(52) U.S. Cl.

CPC ........... *C07D 475/12* (2013.01); *C12Q 1/006* (2013.01); *C12Q 1/26* (2013.01); *C12Y 101/03004* (2013.01)

(58) Field of Classification Search

CPC .................................................... C07D 475/12

See application file for complete search history.

(56) References Cited

U.S. PATENT DOCUMENTS

| | | | |
|---|---|---|---|
| 4,224,125 | A | 9/1980 | Nakamura et al. |
| 4,965,133 | A | 10/1990 | Ueyama |
| 5,520,786 | A | 5/1996 | Bloczynski et al. |
| 5,998,616 | A | 12/1999 | Murthy et al. |
| 2019/0036124 | A1 | 1/2019 | Seferos et al. |

FOREIGN PATENT DOCUMENTS

| | | |
|---|---|---|
| CN | 1620462 | 5/2005 |
| CN | 1639206 | 7/2005 |
| JP | 2003-005355 | 1/2003 |
| JP | 2008-056585 | 3/2008 |
| JP | 2008-222615 | 9/2008 |
| JP | 2008-239615 | 10/2008 |
| KR | 10-2019-0123169 | 10/2019 |
| RU | 2009118990 | 11/2010 |
| RU | 2409586 | 1/2011 |
| WO | 2008-036516 | 3/2008 |
| WO | 2011-126567 | 10/2011 |

OTHER PUBLICATIONS

KIPO, PCT Search Report & Written Opinion of PCT/KR2020/019228 dated Apr. 16, 2021.

D.E. Edmondson, "E1ectronic Effects of 7 and 8 Ring Substituents as Predictors of Flavin Oxidation-Reduction Potentials", In: Flavins and flavoproteins 1999 : proceedings of the thirteenth international symposium, konstanz, Germany, 1999, pp. 71-76.

Justin J. Hasford et al., "Linear Free Energy Substituent Effect on Flavin Redox Chemistry", Journal of the american chemical society, 1998, pp. 2251-2255, Feb. 27, 1998.

Roopali Rai et al., "Comparative binding study of steroidal adenine with flavin and uracil derivatives", Bioorganic & medicinal chemistry letters, 2005, pp. 2923-2925, Apr. 29, 2005.

Sahu Kasai et al., "Synthesis of 10-(8-Aminooctyl)flavin and Its Use in Affinity Chromatography", Bulletin of the chemical society of japan, 1989, pp. 611-613.

*Primary Examiner* — John S Kenyon

(74) *Attorney, Agent, or Firm* — LEX IP MEISTER, PLLC

(57) ABSTRACT

The present invention relates to a novel organic electron-transfer mediator showing an excellent oxidation-reduction potential and a device such as an electrochemical biosensor having improved performance comprising the same.

17 Claims, 26 Drawing Sheets

【FIG. 1】
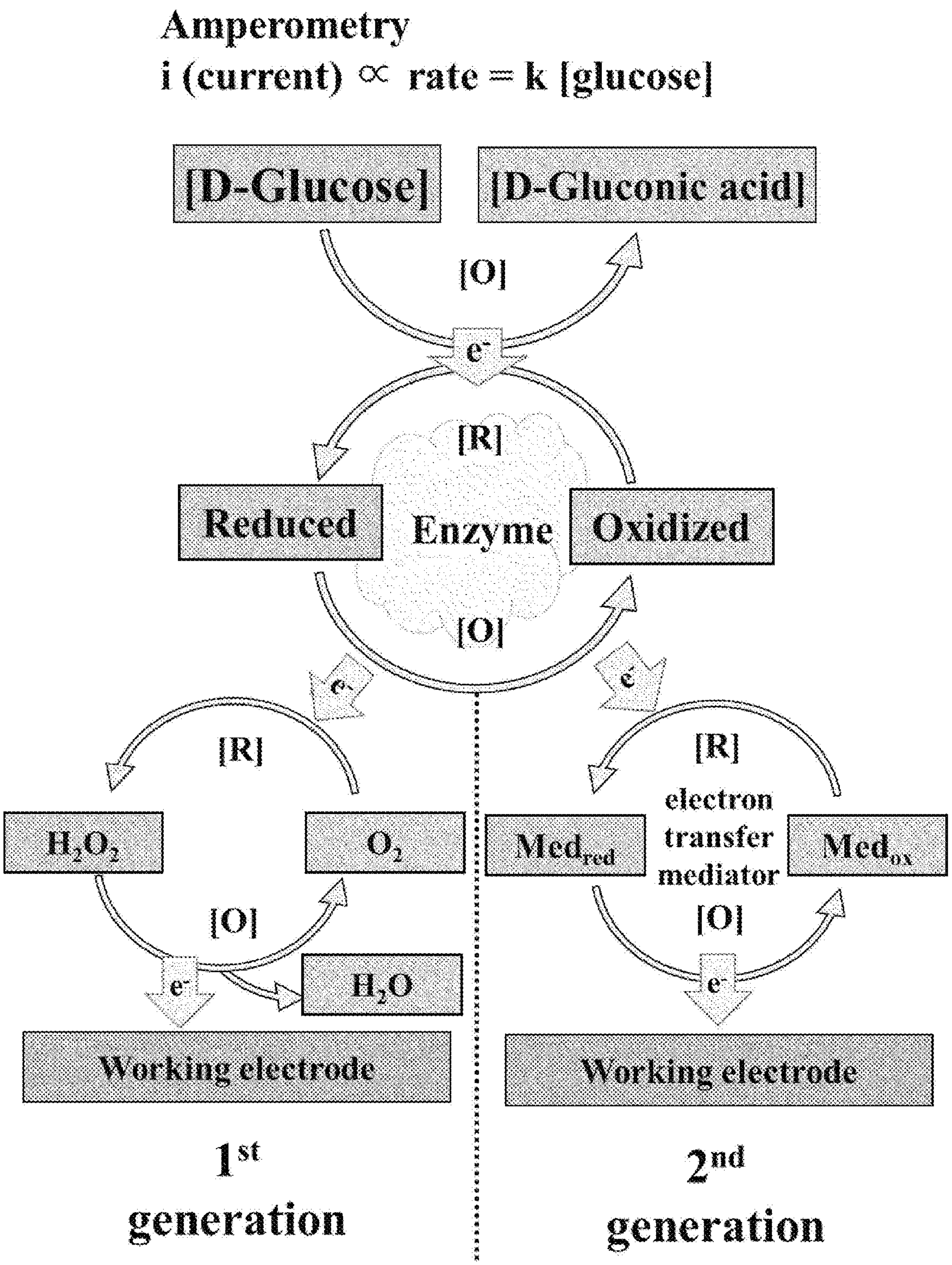

【FIG. 2】
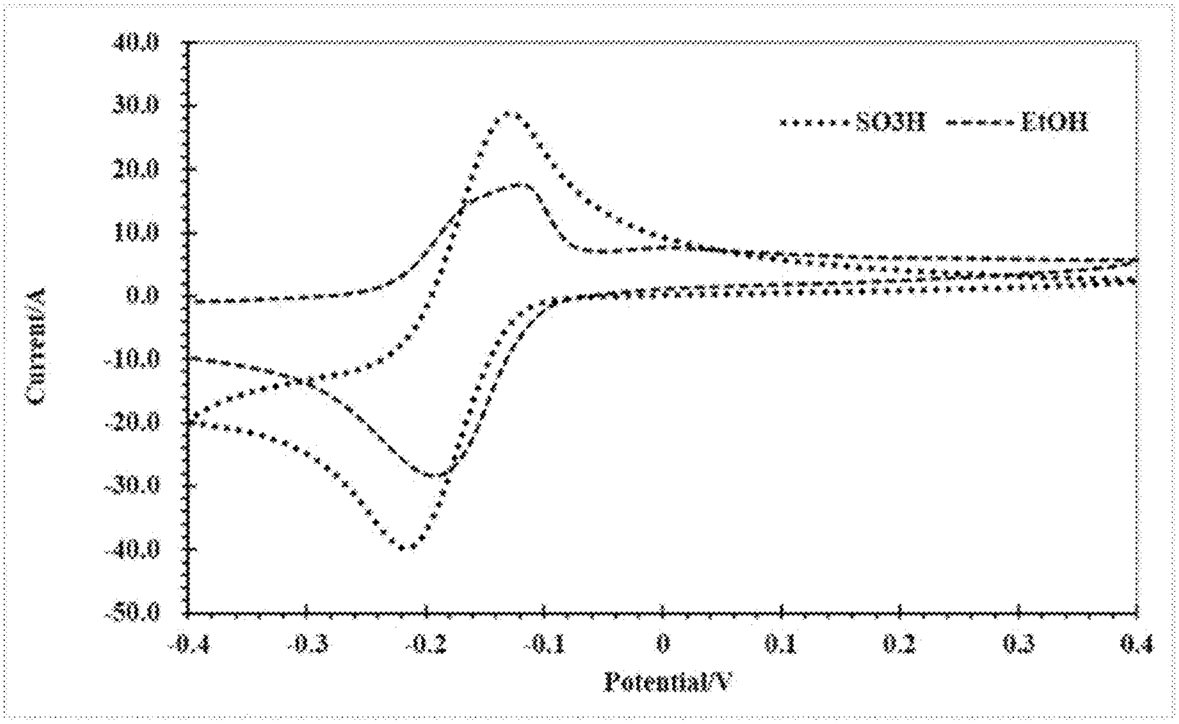

【FIG. 3a】
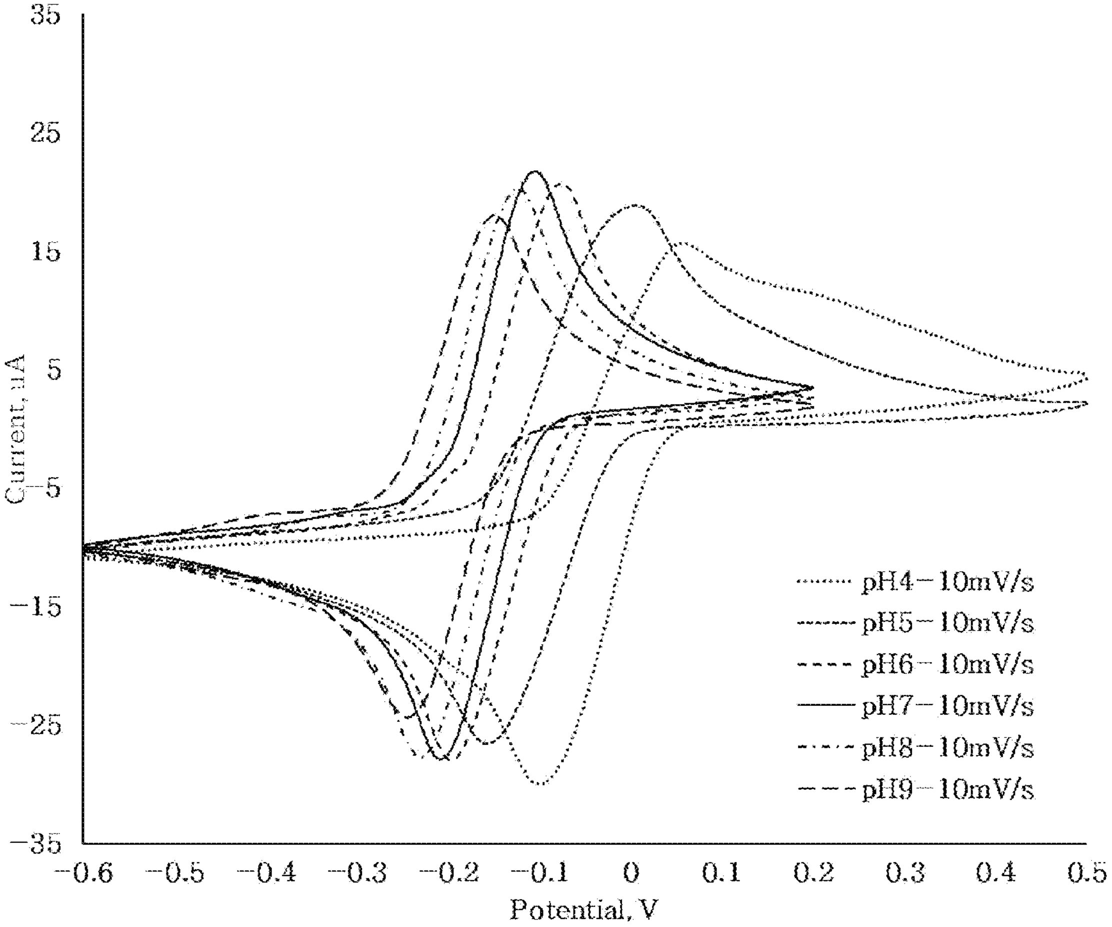

【FIG. 3b】
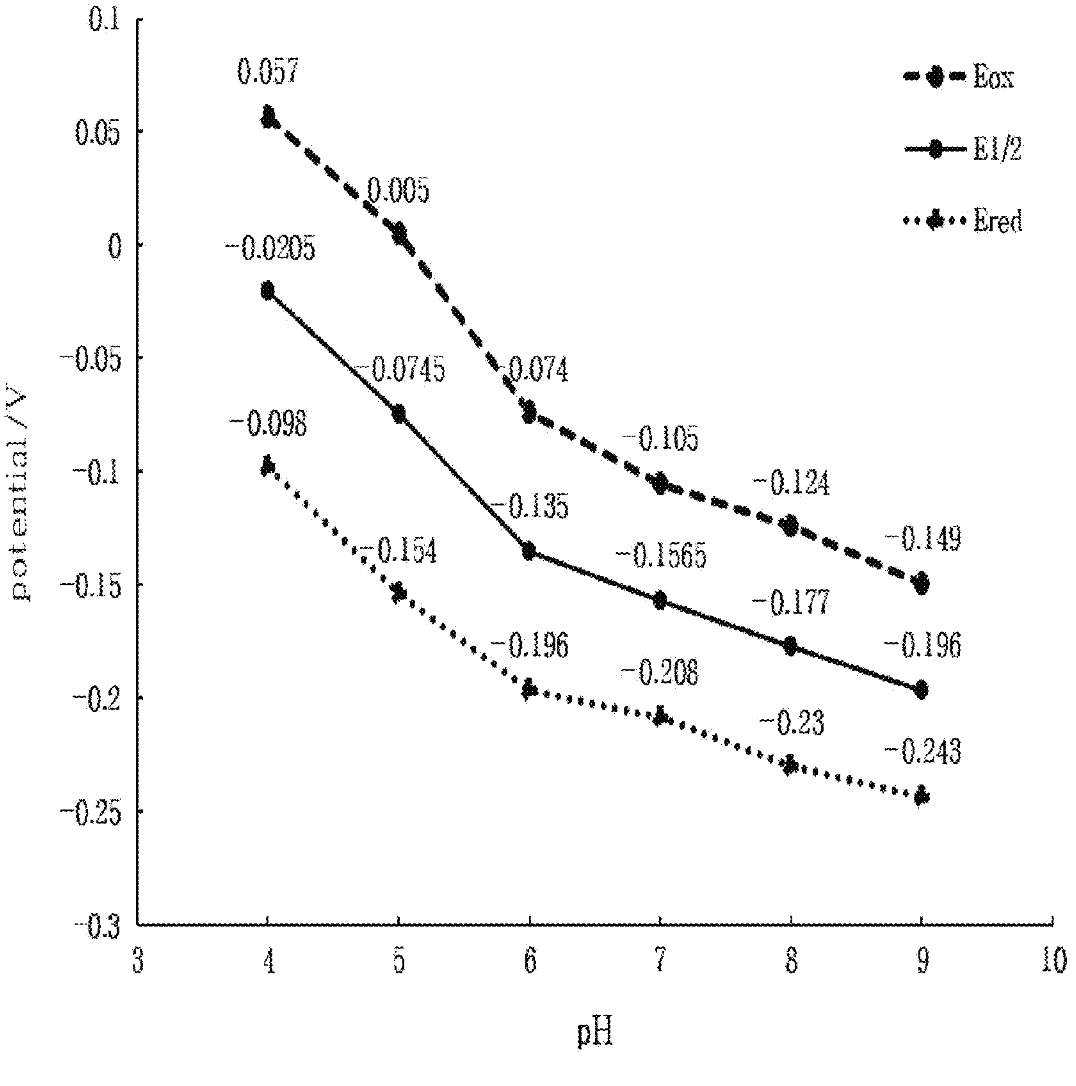

【FIG. 4a】
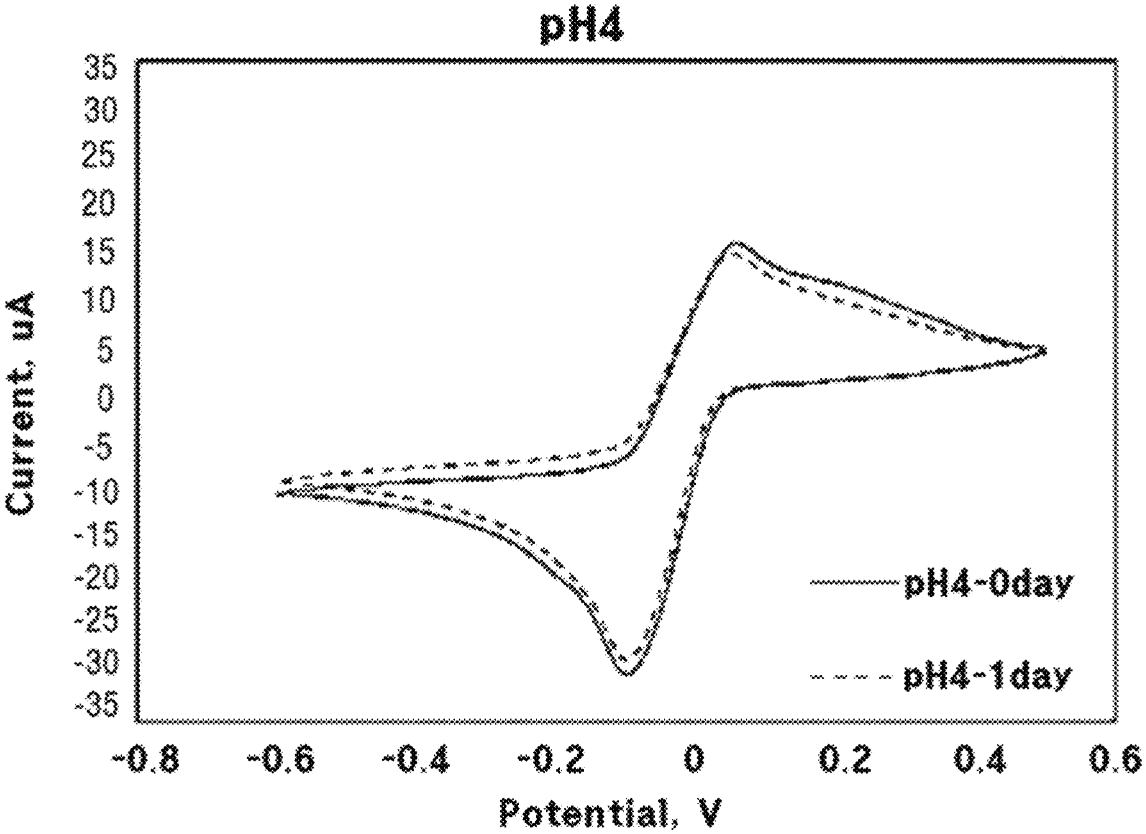

【FIG. 4b】
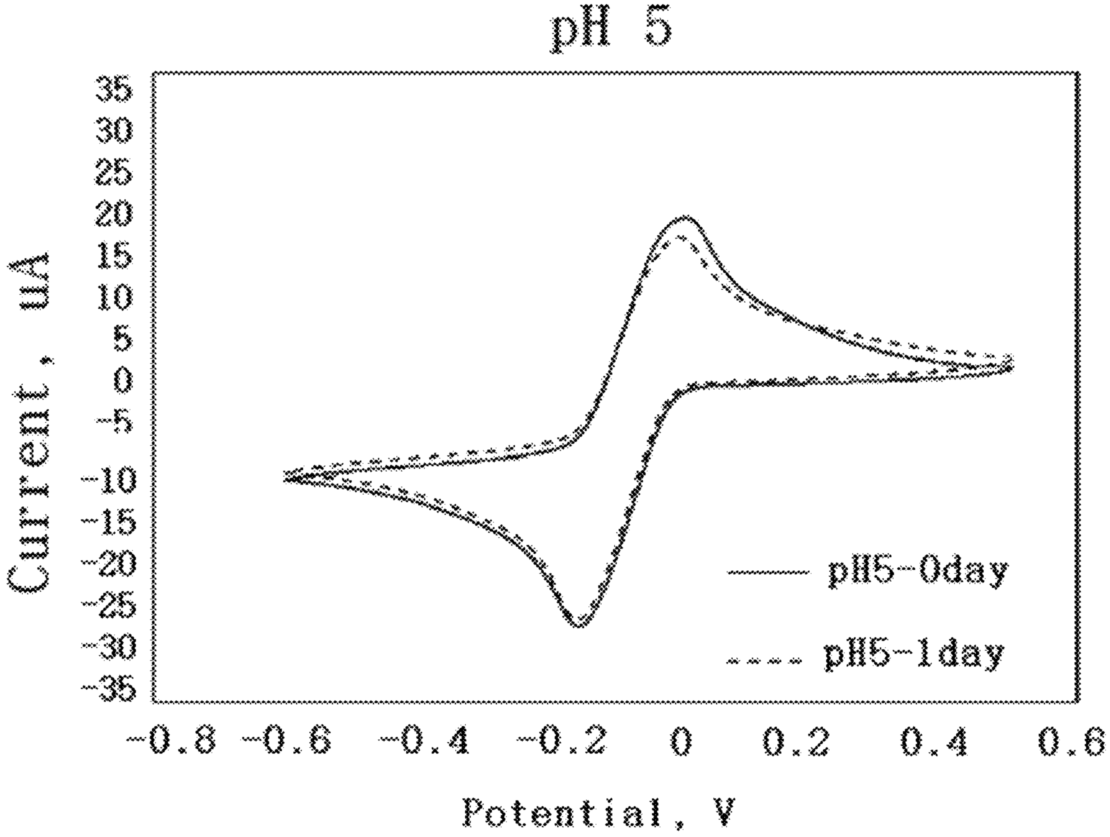

【FIG. 4c】
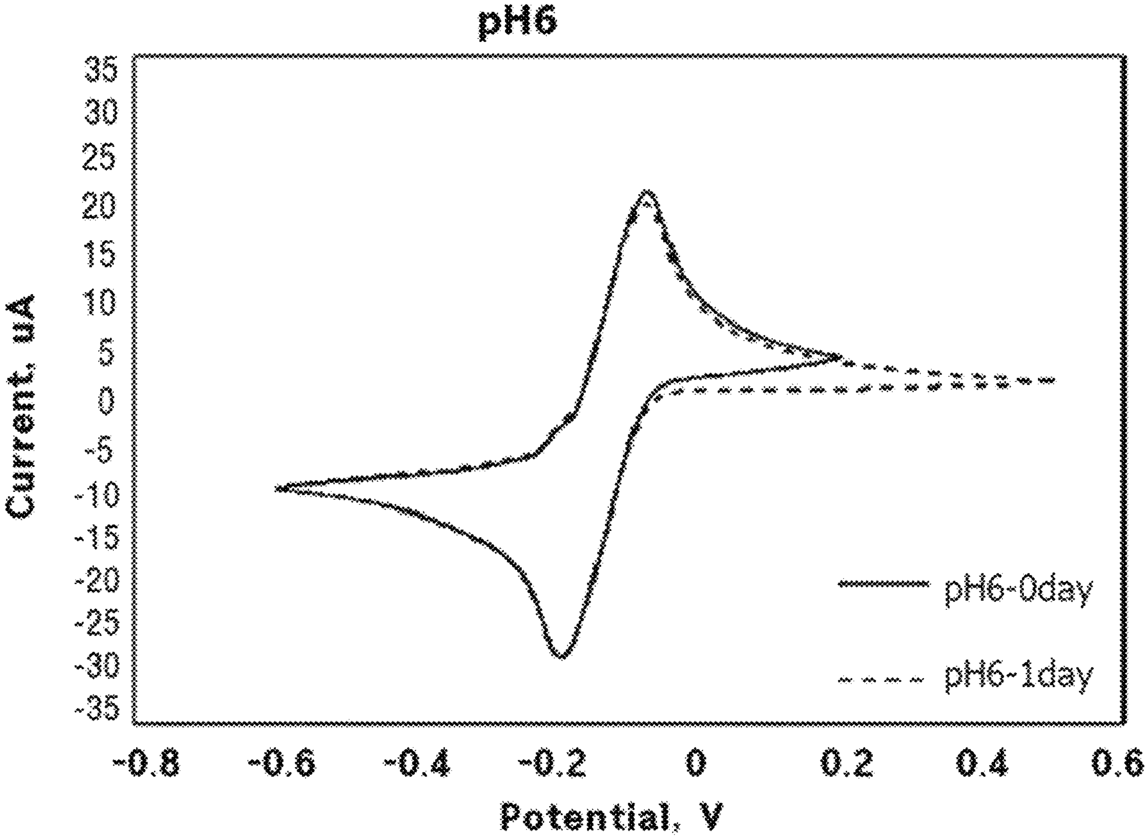

【FIG. 4d】
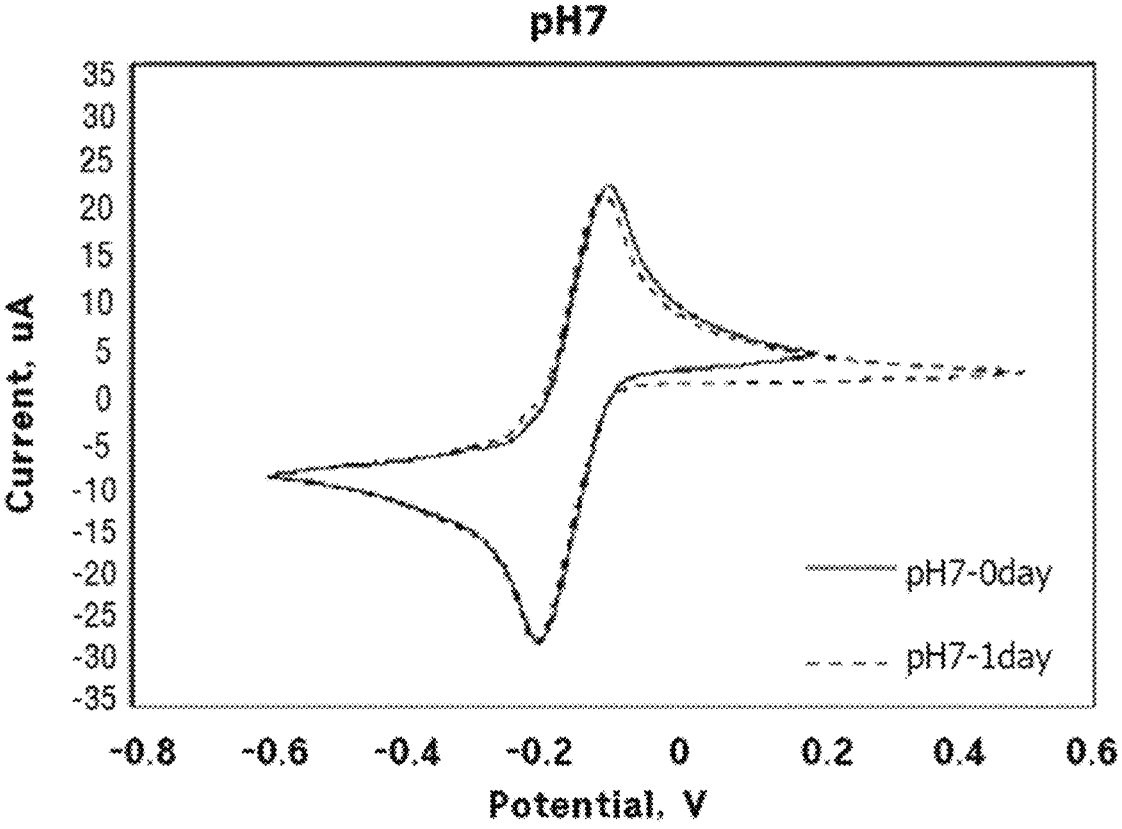

【FIG. 4e】
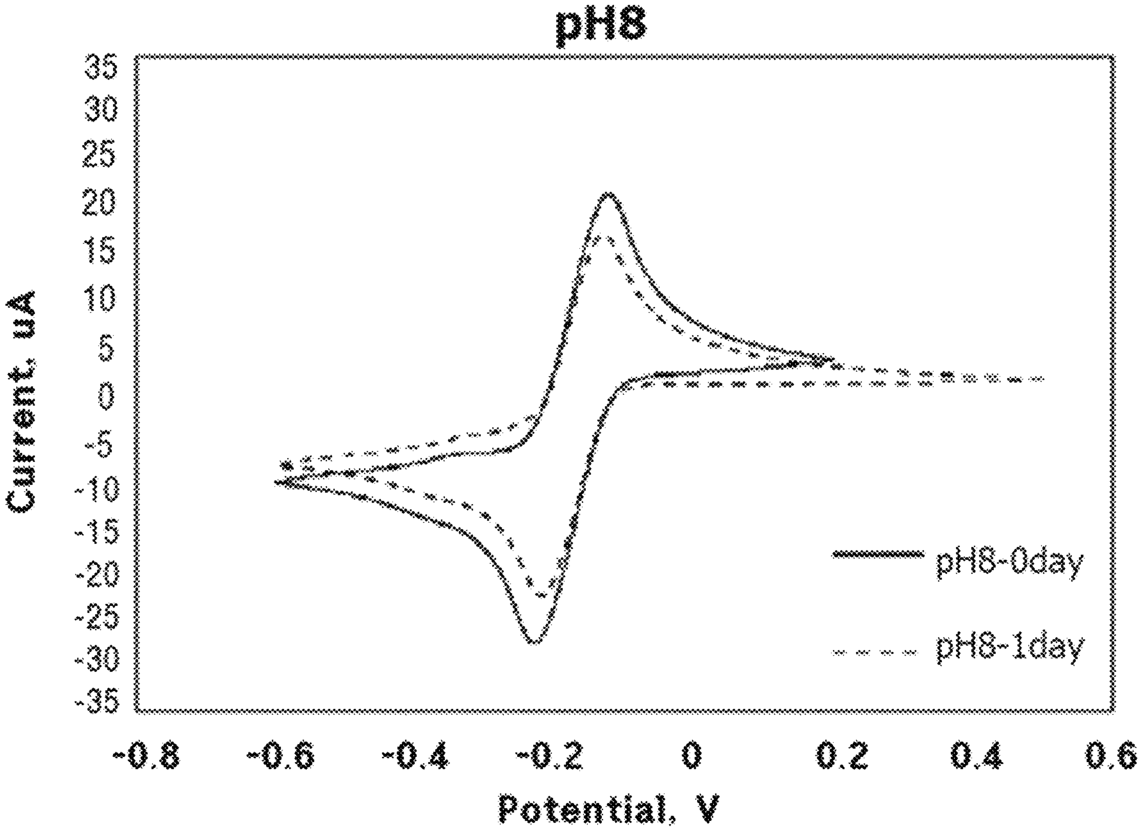

【FIG. 4f】
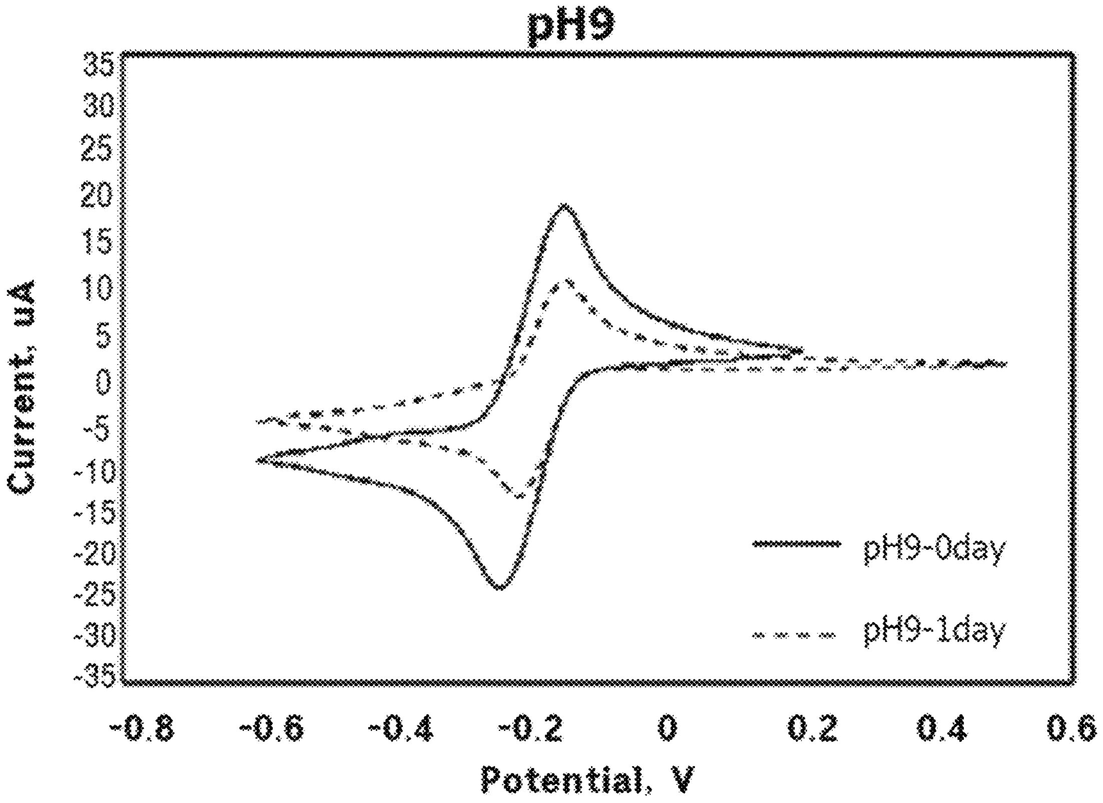

【FIG. 5a】
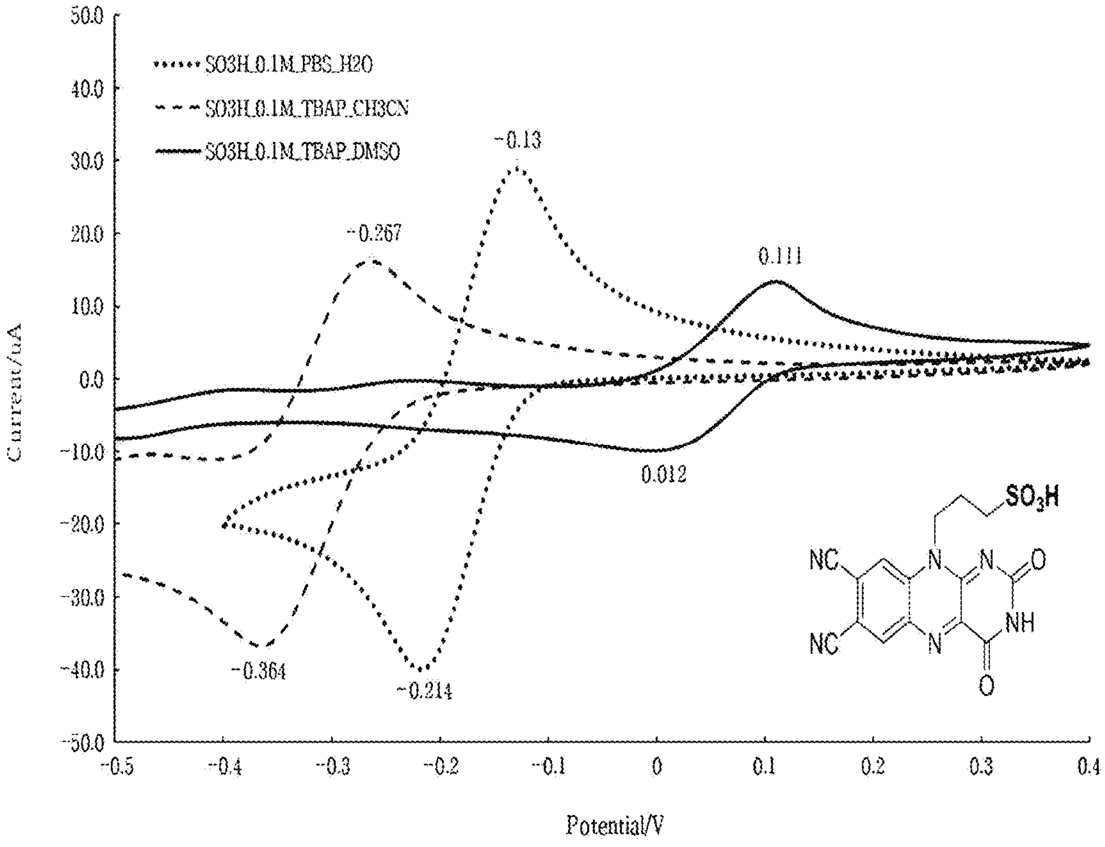
| $SO_3H$ | 0.1M PBS in $H_2O$ | 0.1M TBAP in $CH_3CN$ | 0.1M TBAP in DMSO |
|---|---|---|---|
| $E_{ox}$ | −0.130 | −0.267 | 0.111 |
| $E_{red}$ | −0.214 | −0.364 | 0.012 |
| $E_{1/2}$ | −0.172 | −0.315 | 0.061 |

【FIG. 5b】
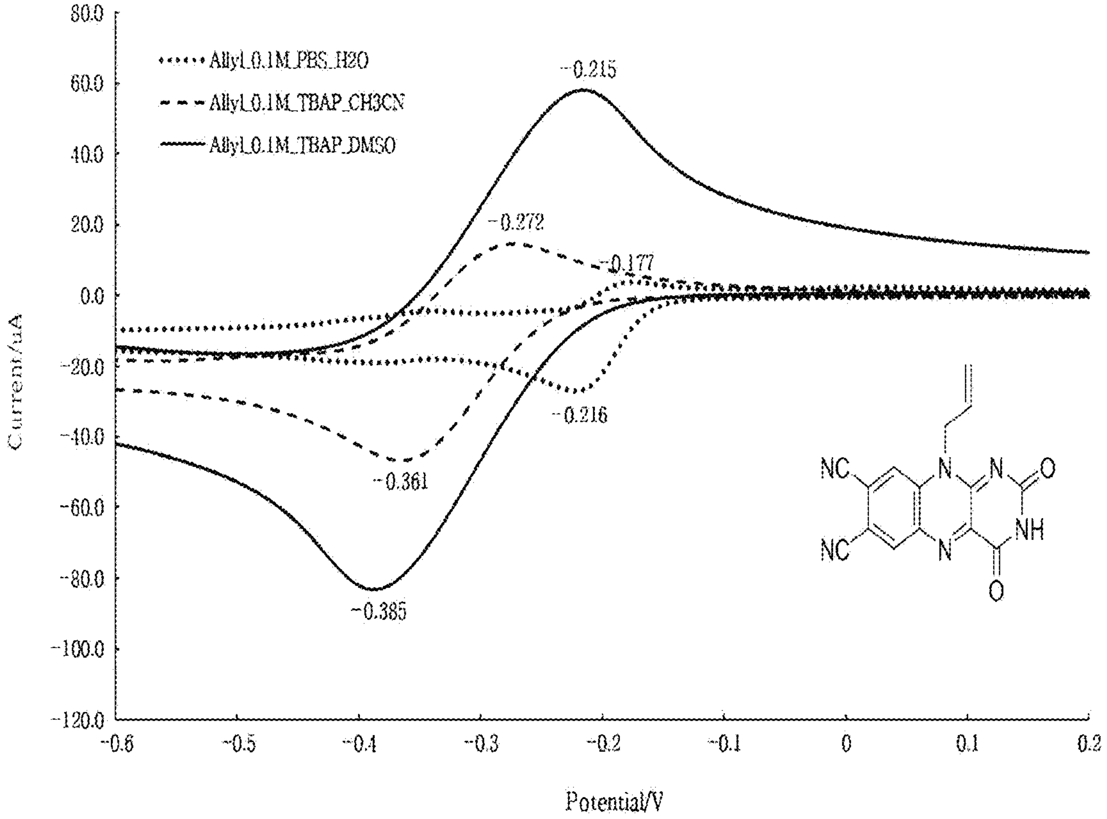
| | 0.1M PBS in $H_2O$ | 0.1M TBAP in $CH_3CN$ | 0.1M TBAP in DMSO |
|---|---|---|---|
| $E_{ox}$ | −0.177 | −0.272 | −0.215 |
| $E_{red}$ | −0.216 | −0.361 | −0.385 |
| $E_{1/2}$ | −0.196 | −0.316 | −0.300 |

【FIG. 5c】
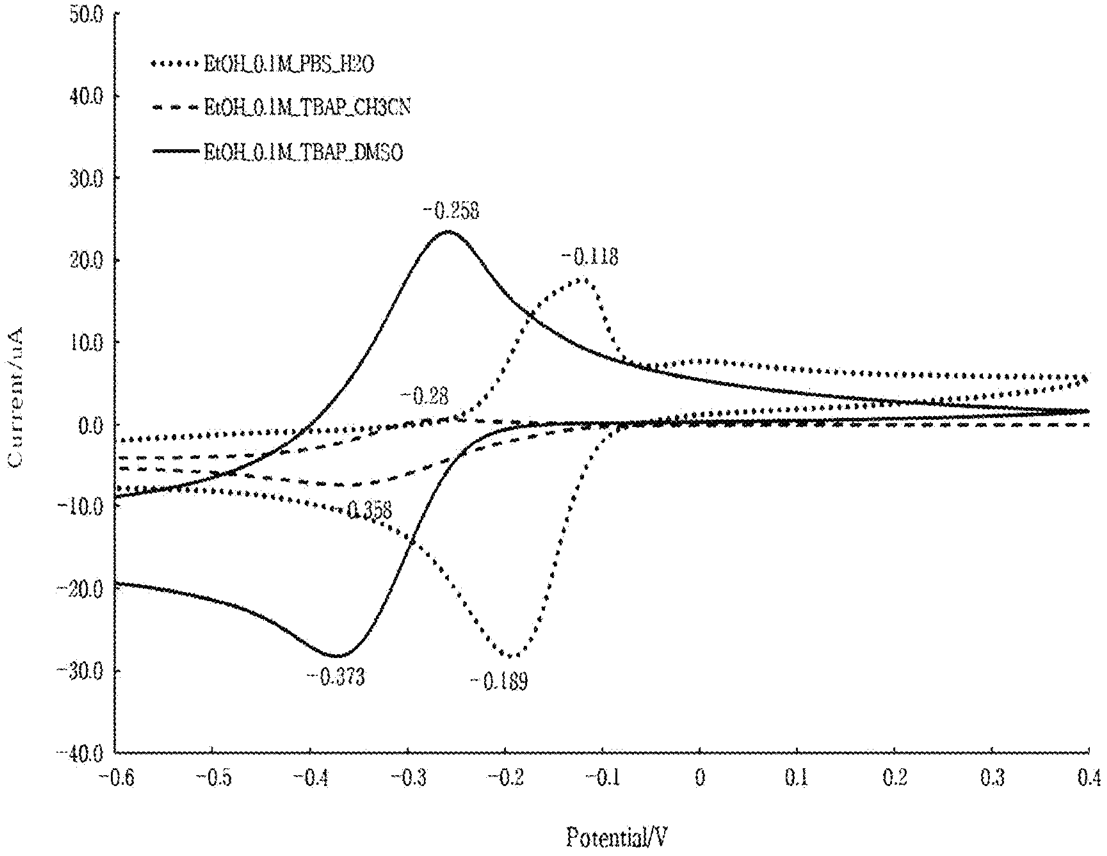
| | 0.1M PBS in $H_2O$ | 0.1M TBAP in $CH_3CN$ | 0.1M TBAP in DMSO |
|---|---|---|---|
| $E_{ox}$ | −0.118 | −0.267 | −0.259 |
| $E_{red}$ | −0.191 | −0.358 | −0.368 |
| $E_{1/2}$ | −0.154 | −0.312 | −0.313 |

【FIG. 6】
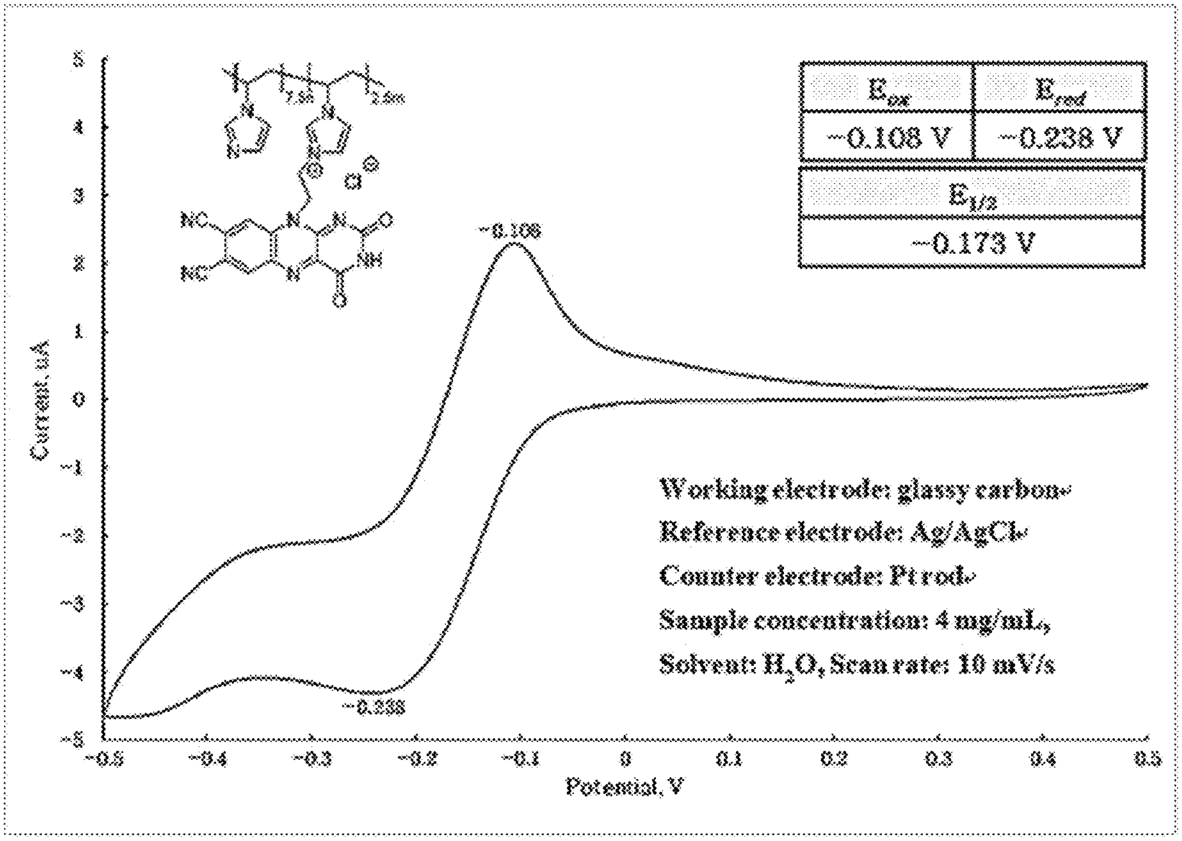

【FIG. 7】
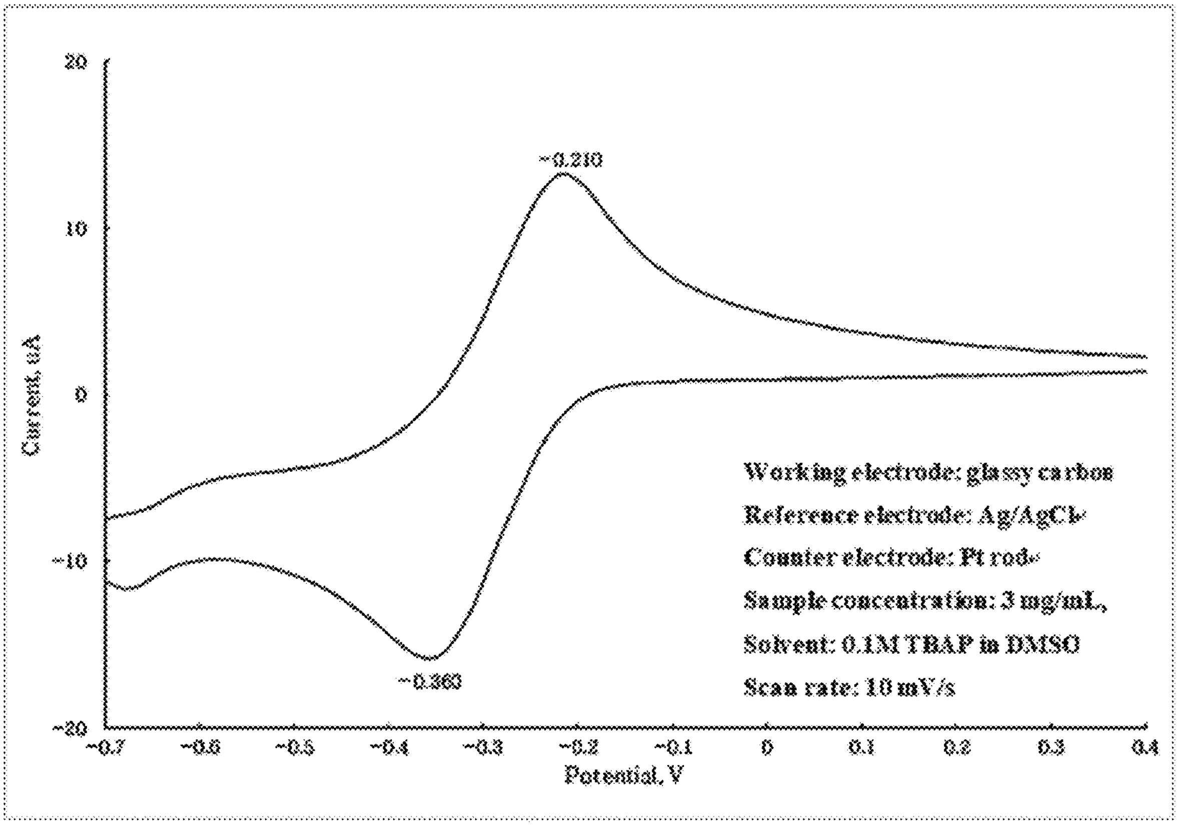

【FIG. 8】
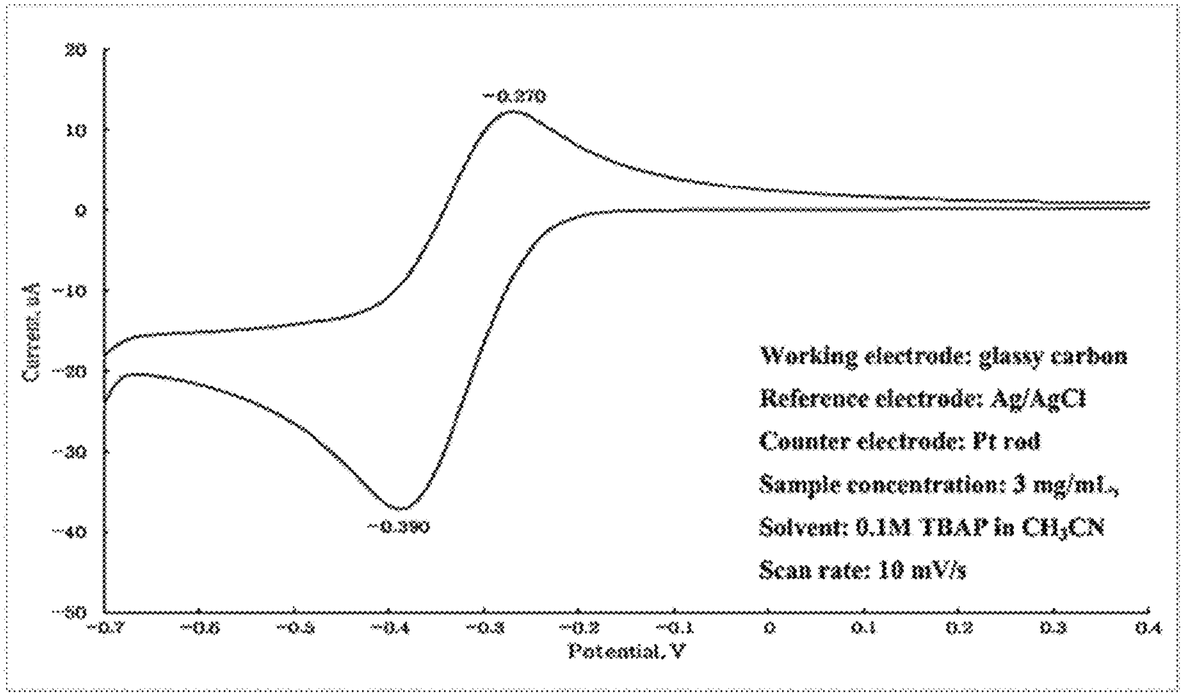

【FIG. 9】
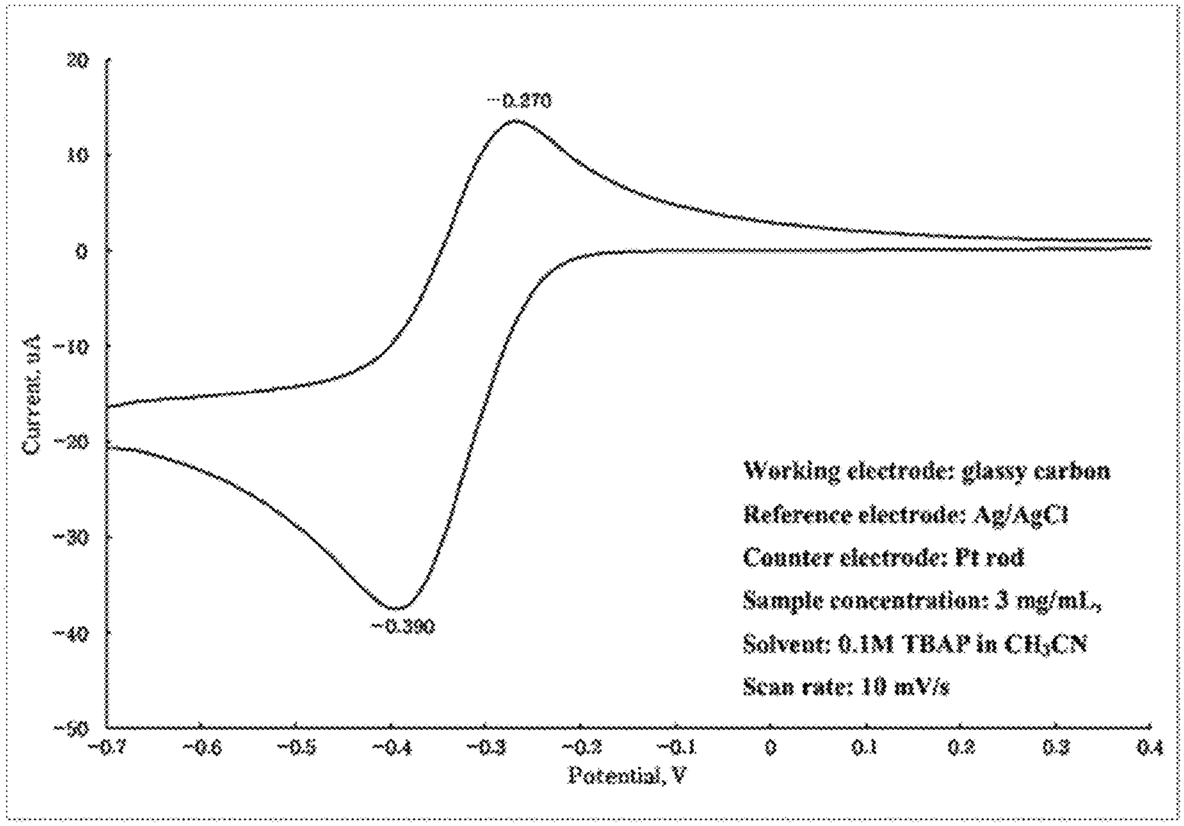

【FIG. 10】
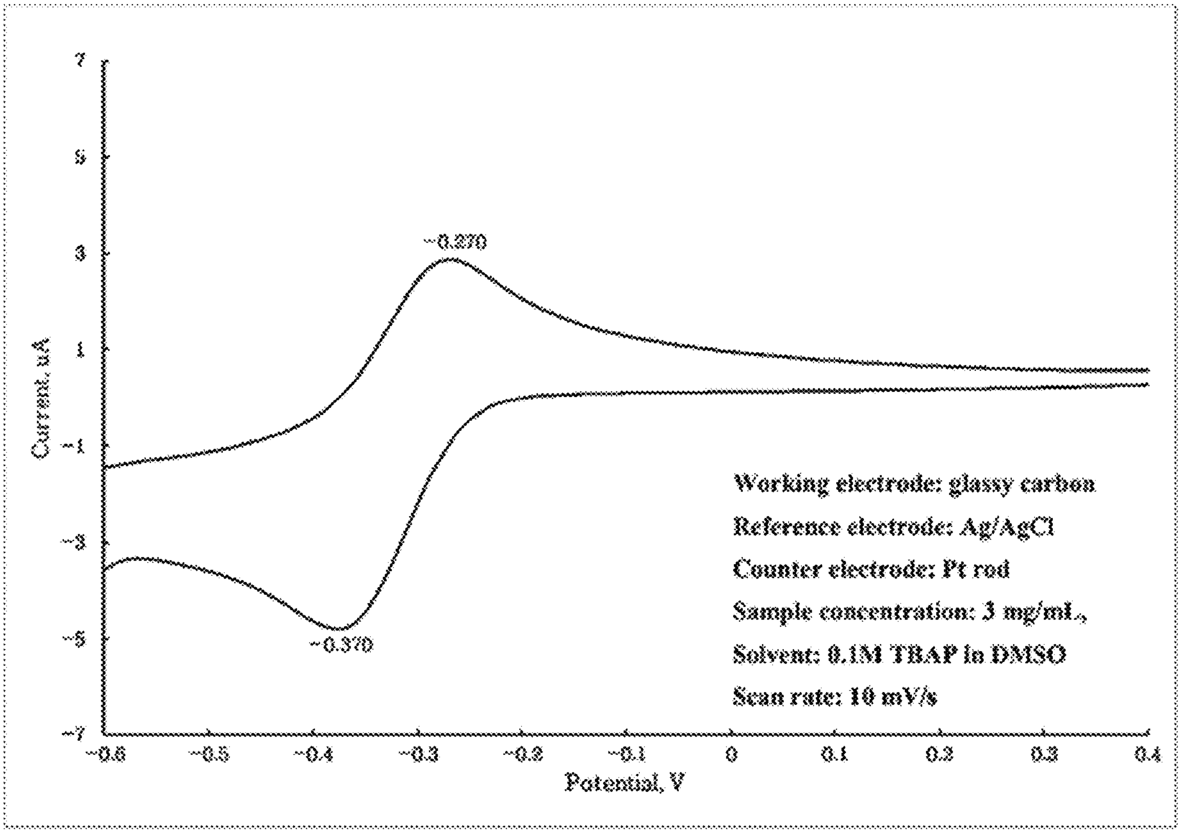

【FIG. 11】
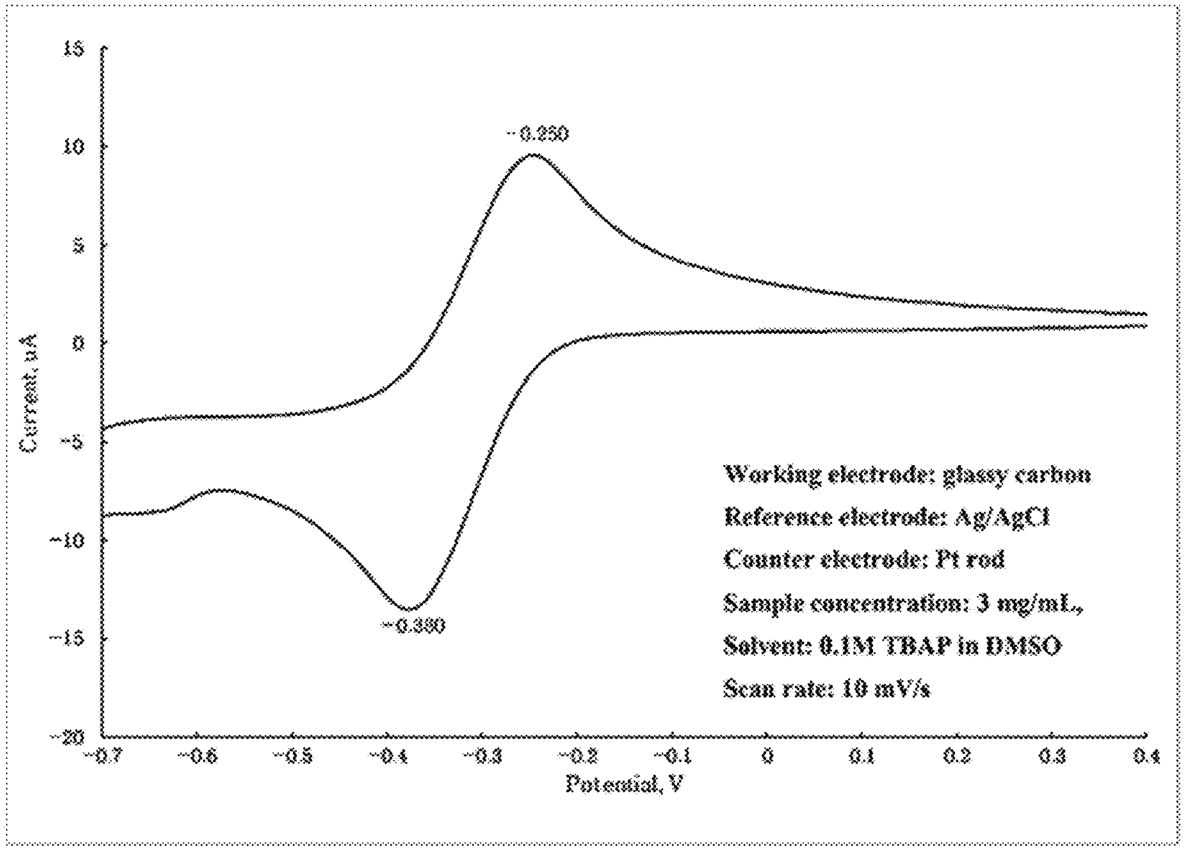

【FIG. 12】
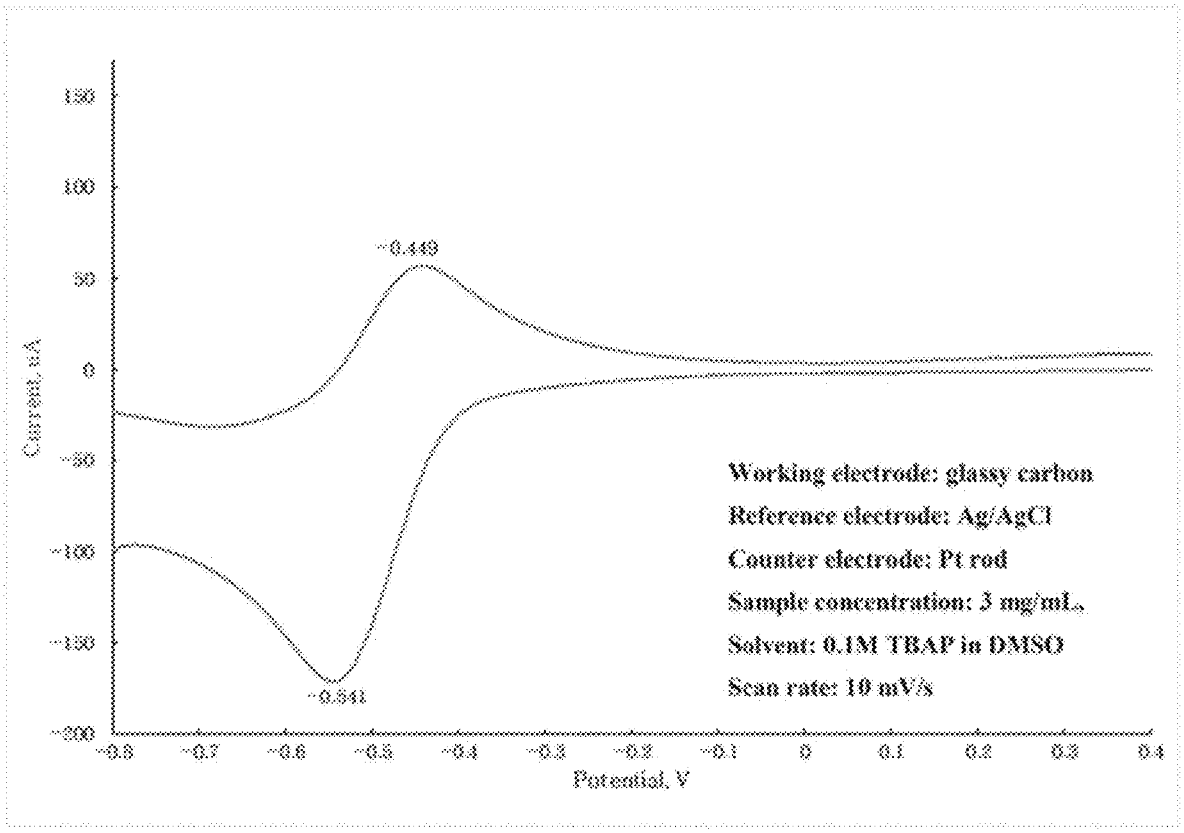

【FIG. 13】
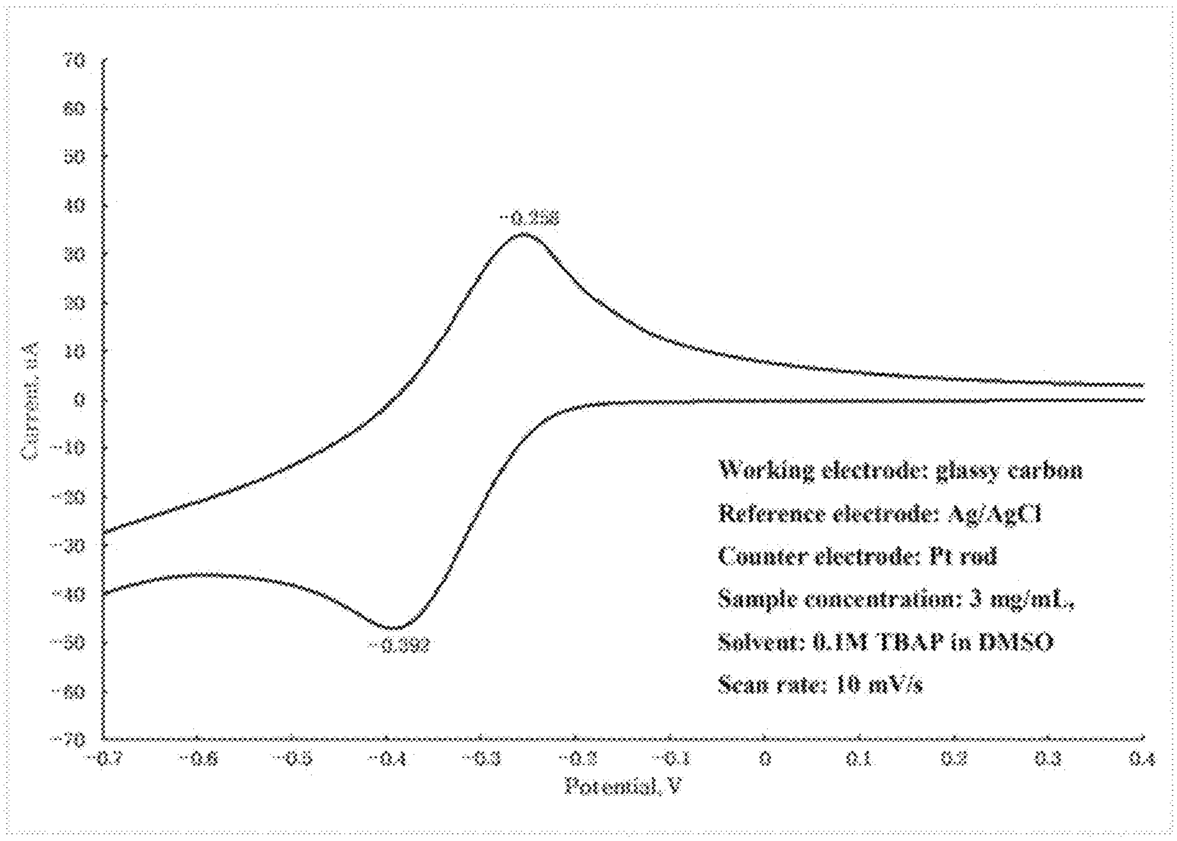

【FIG. 14】
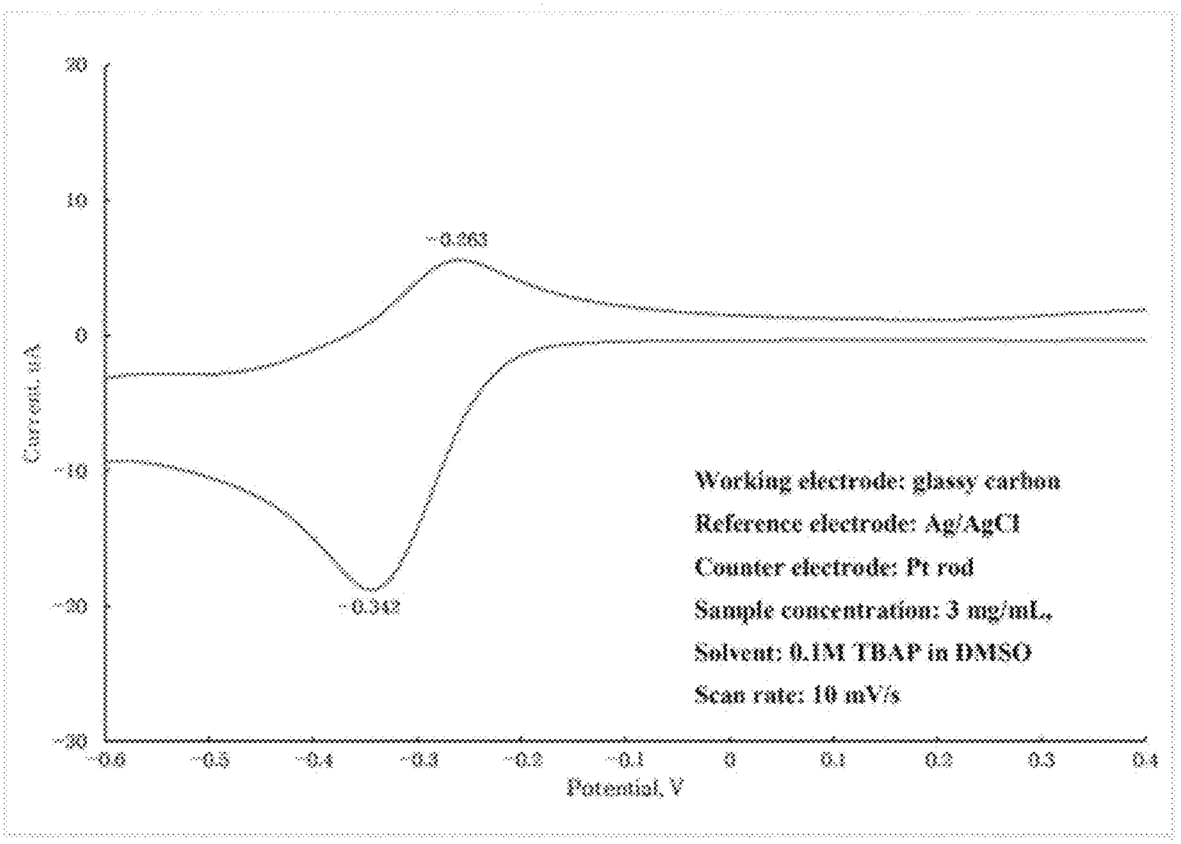

【FIG. 15】
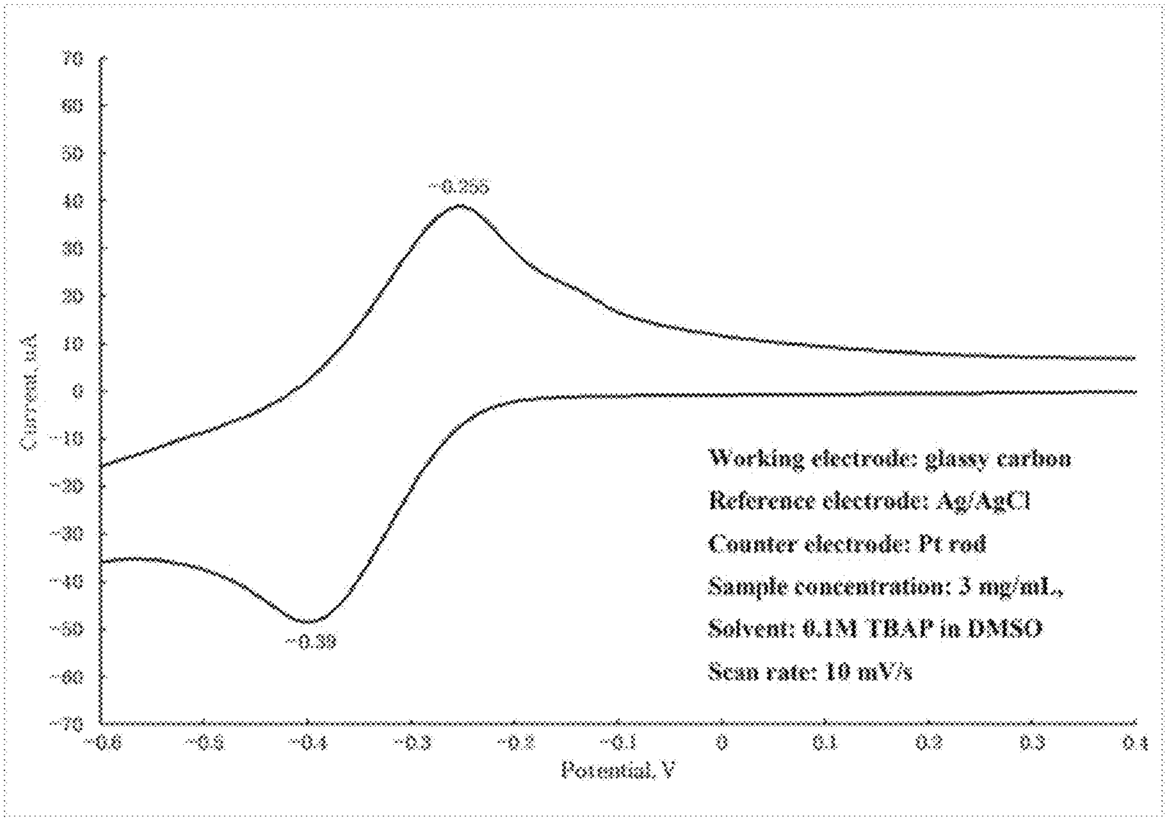

【FIG. 16】
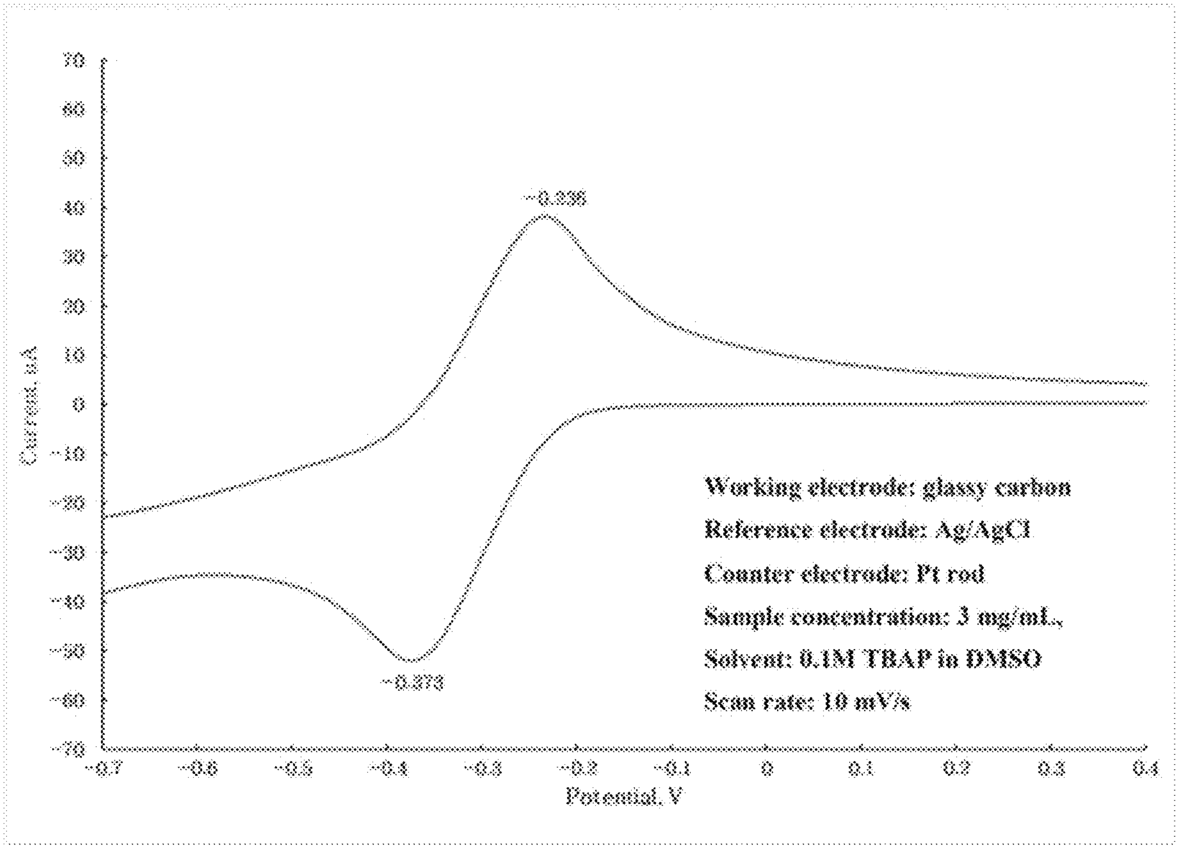

【FIG. 17】
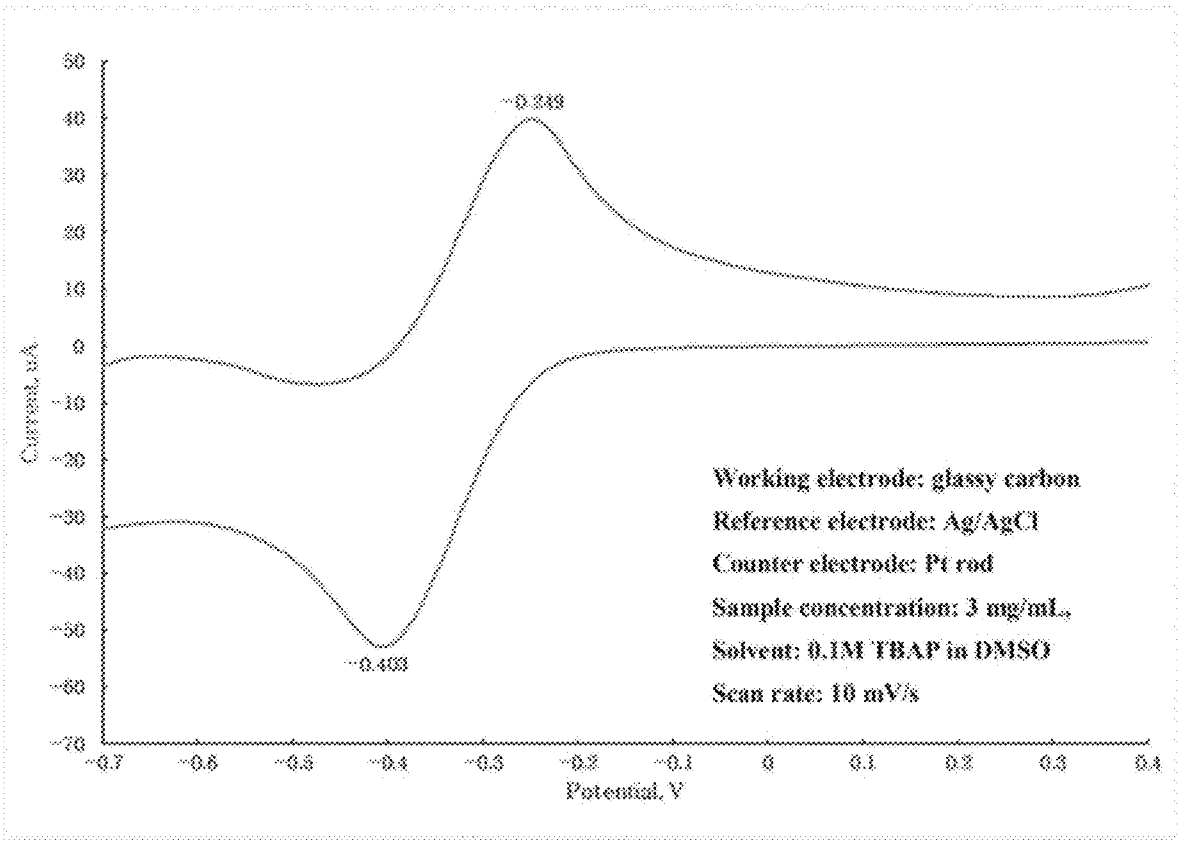

【FIG. 18】
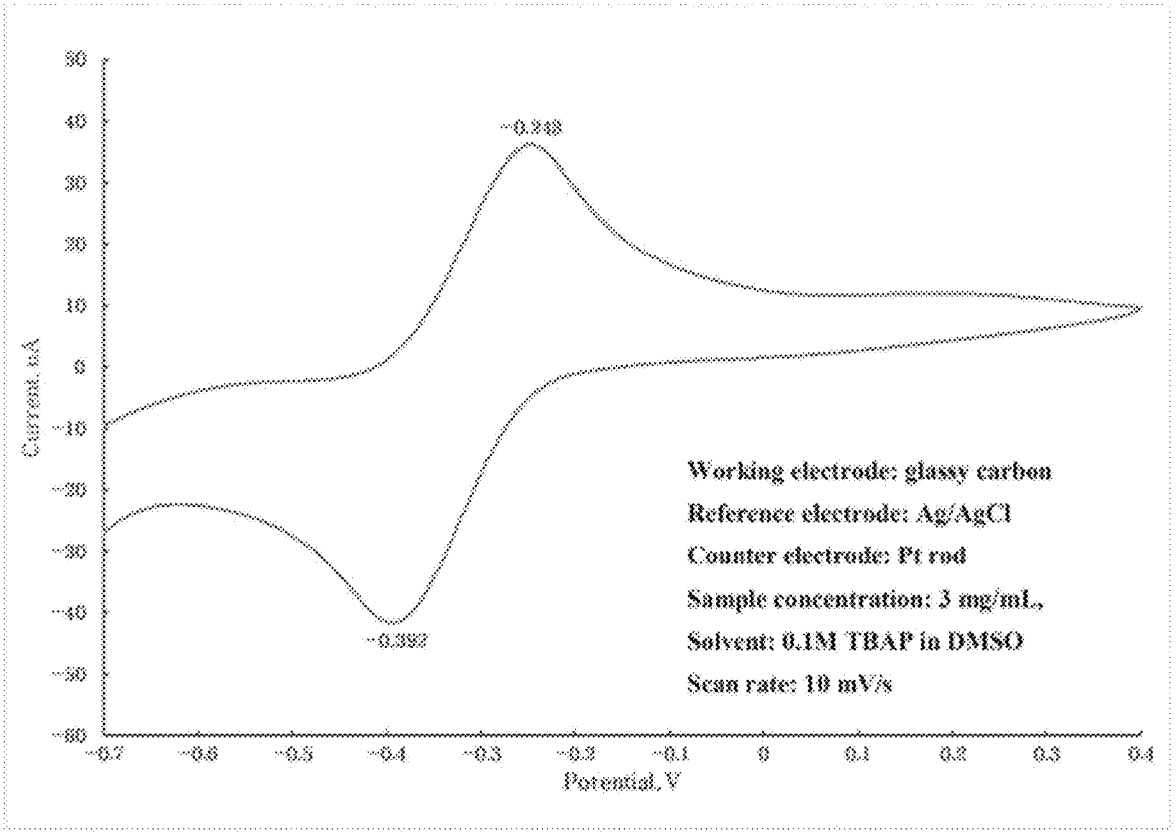

ORGANIC ELECTRON TRANSFER MEDIATOR AND DEVICE COMPRISING SAME

TECHNICAL FIELD

The present invention relates to a novel organic electron-transfer mediator and an electrochemical biosensor comprising the same.

BACKGROUND ART

The operation principle of a glucose sensor is as FIG. 1. Specifically, glucose is oxidized by glucose oxidase to gluconic acid, and a reduced intermediate that receives electrons transfers electrons to an electrode. As a result, the flow of electrons generated by the reaction between blood glucose and enzyme is converted into an electrical signal, so that the blood glucose concentration can be known.

A representative glucose dehydrogenase used in a blood glucose measurement strip is glucose dehydrogenase-flavin adenine dinucleotide (FAD-GDH). An electron-transfer mediator capable of helping movement of electrons between FAD-GDH and an electrode is required, and $Fe(CN)_6^{-3}$ is known as an appropriate compound because it is easily soluble in water, is inexpensive and has high sensitivity. However, due to low affinity of the active site, the rate constant ($k_2=k_{cat}/k_M$) of FAD-GDH and $Fe(CN)^3$ is as low as about $1\times10^3$ $M^{-1}s^{-1}$, so there is a limitation in that the reactivity between the two is not good.

On the other hand, an osmium-based complex having a high rate constant is used as an electron-transfer mediator. When a ligand of the complex is modified, it can be adjusted to have an appropriate electrochemical potential, so it is very useful in terms of usability, but as the osmium metal is very expensive, it is not suitable for use in a disposable blood glucose measurement strip. Therefore, research on organic compounds as inexpensive and sustainable alternatives is in progress. Although the characteristics of various organic electron-transfer mediators including a naphthoquinone/phenanthrenequinone derivative, there is still a need for development of organic-based materials that can be used as such electron-transfer mediator.

DISCLOSURE

Technical Problem

Under these circumstances, the present inventors have paid attention to oxidation reduction reaction of a phenothiazine organic electron transfer mediator. When the oxidation reduction reaction occurs in the corresponding phenothiazine organic electron transfer mediator as Reaction formula 1 below, the oxidation reduction potential is known as −0.1 V compared to the Ag/AgCl reference electrode when measured in an aqueous solution (See International Patent Publication No. WO 2008/036516, See U.S. Pat. No. 5,520,786).

An important factor that the glucose sensor has poor accuracy in the hypoglycemic section (low response current section) is that there is a relatively high background current in this section. This background current occurs because there is a pathway for electrons from the surrounding environment in addition to the electrons from the enzyme. Therefore, in order to minimize this background current, the path through which the electron-transfer mediator receives electrons from the surrounding environment must be blocked, and for this purpose, it is optimal that the range of the standard reduction potential of the electron-transfer mediator has a value between about −0.2~0.1 V compared to the Ag/AgCl reference electrode when measured in an aqueous solution. When measured in an organic solvent ($CH_3CN$, DMSO, etc.), it may exhibit a value between −0.4~0.1 V compared to the Ag/AgCl reference electrode.

[Reaction Formula 1]

Oxidation reduction reaction of phenothiazine organic electron transfer mediator

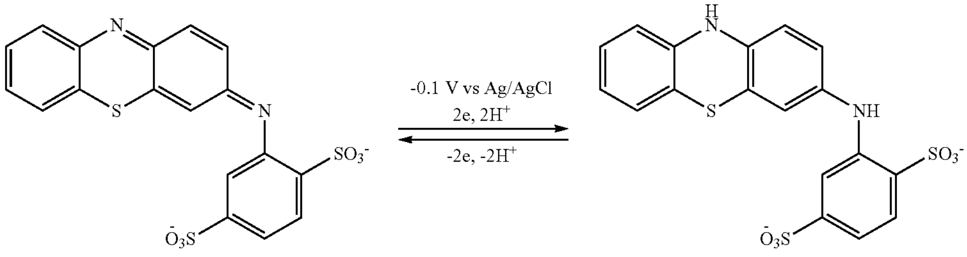

oxidized form reduced form

On the other hand, the oxidation reduction potential of a flavin [or isoalloxazine]derivative such as Reaction formula 2 is known as −0.46 V compared to the Ag/AgCl reference electrode. This compound has a similar oxidation reduction potential to FAD, a derivative of FAD, well known as an oxidation reduction coenzyme, but it does not show an optimal oxidation reduction potential as an electron-transfer mediator for a glucose sensor.

[Reaction Formula 2]

Structure of riboflavin and flavin adenosine dinucleotide (FAD) and oxidation reduction reaction of derivatives thereof (isoalloxazine)

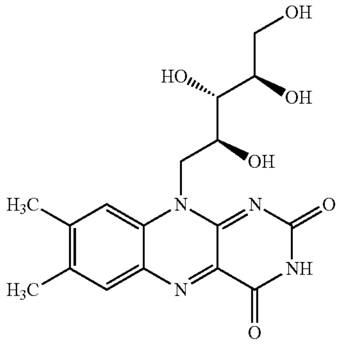

riboflavin
(vitamin $B_2$)

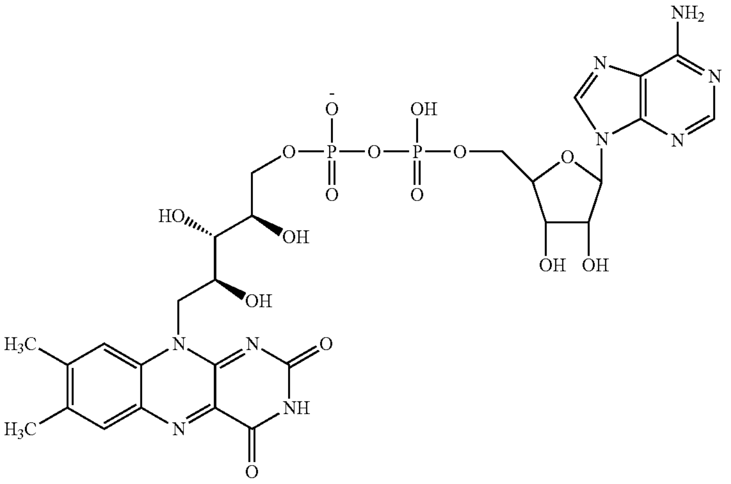

flavin adenosine dinucleotide (FAD)

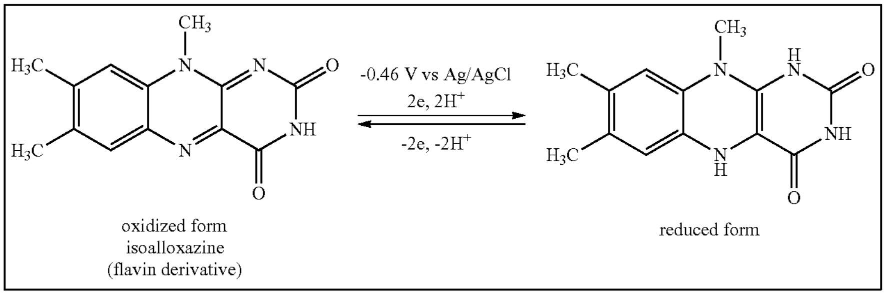

oxidized form
isoalloxazine
(flavin derivative)

reduced form

Considering the oxidation reduction potential of the reported FAD-FDAH$_2$ derivatives, it can be seen that the potential of the derivatives having an electron withdrawing substituent is shifted in a more positive direction (Reference *J. Am. Chem. Soc.* 1998, 120, 2251-2255) [Reaction formula 3]. According to this document, when electron withdrawing groups at positions 7 and 8 of the flavin framework, F, Cl, CN and the like are substituted, the oxidation reduction potential shifts in a more positive direction. However, when it is measured in an aqueous solution in the flavin derivatives described in this document, there is no compound having an optimal oxidation reduction potential (−0.2~0.1V) of a glucose electron-transfer mediator. It can be expected to have a desired oxidation reduction potential value only when it has a CN group at least at the 7$^{th}$ and 8$^{th}$ positions or a substituent with a stronger electron withdrawing group property than this is introduced.

[Reaction Formula 3]

Reduction potential (V) of flavin derivatives (100 mM, pH 7.4 HEPES vs Ag/AgCl) (Reference: *J. Am. Chem. Soc.* 1998, 120, 2251-2255)

Reduction Potentials (E$^{o\prime}$ vs Ag/AgCl) of Some Flavin Derivatives

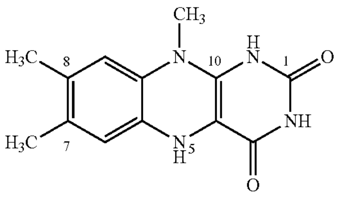

-0.456 V

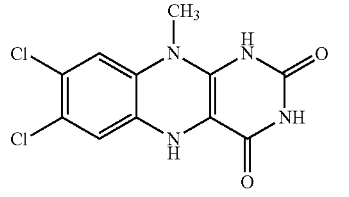

-0.338 V

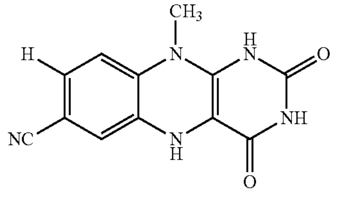

-0.321 V

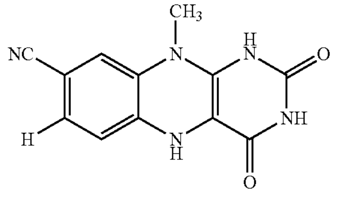

-0.283 V

Hasford, J. J.; Rizzo, C. J. *J. Am. Chem. Soc.* 1998, 120, 2251-2255.

Therefore, it has been confirmed that an organic-based electron-transfer mediator having a target oxidation reduction potential spec and having an oxidation reduction potential capable of minimizing a background current in the hypoglycemic section of the glucose sensor, when an appropriate electron withdrawing substituent is introduced at positions 7 and 8, considering that the appropriate oxidation reduction potential for electron transfer in a glucose sensor is between −0.2~0.1 V in an aqueous solution, thereby completing the present invention.

Technical Solution

Accordingly, an object of the present invention is to provide a novel organic electron-transfer mediator which exhibits an oxidation-reduction potential value optimized to a glucose sensor and gives performance of a device such as an electrochemical biosensor and a method for preparing the same.

Another object of the present invention is to provide a device, preferably, an electrochemical biosensor, comprising the novel organic electron-transfer mediator.

Advantageous Effects

When the organic electron-transfer mediator according to the present invention is used for a device such as an electrochemical biosensor, by showing an excellent oxidation-reduction potential spec, the performance of the electrochemical biosensor can be improved.

BRIEF DESCRIPTION OF THE DRAWINGS

FIG. 1 is a diagram schematically showing the principle of a glucose sensor.

FIG. 2 is a graph showing the result of measuring cyclic voltammetry using the organic electron-transfer mediator according to the present invention, 3-(7,8-dicyano-2,4-dioxo-3,4-dihydrobenzo[g]pteridin-10(2H)-yl)propane-1-sulfonic acid [Chemical formula 2] 10-(2-hydroxyethyl)-2,4-dioxo-2,3,4,10-tetrahydrobenzo[g]pteridine-7,8-dicarbonitrile [Chemical formula 16].

FIGS. 3*a* and 3*b* are graphs showing the result of measuring cyclic voltammetry according to pH using the organic electron-transfer mediator according to the present invention [Chemical formula 2].

FIGS. 4*a*-4*f* are graphs showing the result of the stability test by pH using the organic electron-transfer mediator according to the present invention [Chemical formula 2]. The stability result at FIG. 4*a*: pH 4, FIG. 4*b*: pH 5, FIG. 4*c*: pH 6, FIG. 4*d*: pH 7, FIG. 4*e*: pH 8 and FIG. 4*f*: pH 9 is shown.

FIGS. 5*a*-5*c* are figures showing cyclic voltammetry (CV) measured in several kinds of buffer solutions of 3 kinds of the organic electron-transfer mediators according to the present invention, which are the cyclic voltammetry measured in 0.1 M PBS in $H_2O$, 0.1M TBAP in $CH_3CN$, 0.1M TBAP in DMSO of 5a: Chemical formula 2, 5b: Chemical formula 14 and 5c: Chemical formula 15, and the oxidation reduction potential value and $E_{1/2}$ at that time.

FIG. 6 is cyclic voltammetry measured using water as a solvent for an electron-transfer mediator to which a polymer matrix of Chemical formula 25 is connected.

FIG. 7 shows cyclic voltammetry of the organic electron-transfer mediator according to Chemical formula 3.

FIG. 8 shows cyclic voltammetry of the organic electron-transfer mediator according to Chemical formula 4.

FIG. 9 shows cyclic voltammetry of the organic electron-transfer mediator according to Chemical formula 5.

FIG. 10 shows cyclic voltammetry of the organic electron-transfer mediator according to Chemical formula 6.

FIG. 11 shows cyclic voltammetry of the organic electron-transfer mediator according to Chemical formula 7.

FIG. 12 shows cyclic voltammetry of the organic electron-transfer mediator according to Chemical formula 8.

FIG. 13 shows cyclic voltammetry of the organic electron-transfer mediator according to Chemical formula 9.

FIG. 14 shows cyclic voltammetry of the organic electron-transfer mediator according to Chemical formula 10.

FIG. 15 shows cyclic voltammetry of the organic electron-transfer mediator according to Chemical formula 11.

FIG. 16 shows cyclic voltammetry of the organic electron-transfer mediator according to Chemical formula 12.

FIG. 17 shows cyclic voltammetry of the organic electron-transfer mediator according to Chemical formula 13.

FIG. 18 shows cyclic voltammetry of the organic electron-transfer mediator according to Chemical formula 14.

BEST MODE

Hereinafter, the present invention will be described in detail.

All technical terms used in the present invention, unless otherwise defined, have the meanings commonly understood by those skilled in the art of the present invention. In addition, although a preferable method or sample is described in the present description, but similar or equivalent ones are also included in the scope of the present invention. Furthermore, the numerical values described in the present description are considered to include the meaning of "about" even if not specified. The contents of all publications incorporated in the present description by reference are incorporated by reference in their entirety.

The definition of the residues used in the present invention will be described in detail. If otherwise specified, it follows the definition, and unless otherwise specified, each residue has the following definition, and is used in the same meaning as commonly understood by those skilled in the art.

In the present invention, the example of "halo" or "halogen" includes fluoro, chloro, bromo and iodo.

In the present invention, "alkyl" means an aliphatic hydrocarbon radical, and includes all linear, branched or cyclic (cycloalkyl) hydrocarbon radicals.

In the present invention, "alkoxy" represents a —O-alkyl or alkyl-O-group, and herein, the alkyl group is same as defined above. For example, it includes methoxy, ethoxy, n-propoxy, n-butoxy, and t-butoxy, but not limited thereto.

In the present invention, the term "hydroxy" or "hydroxyl" alone or combined with other term means —OH.

In the present invention, "cyano" represents —CN; and "amino" represents —$NH_2$; and "nitro" represents —$NO_2$.

In the present invention, "aryl" refers to a monovalent aromatic hydrocarbon having for example, 6 to 30 carbon atoms (C6-C30) induced by removing one hydrogen atom in one carbon atom in a parent aromatic ring system. The aryl may include a bicyclic radical comprising an aromatic ring fused with a saturated, partially unsaturated ring.

In the present invention, "heteroaryl" means a monovalent or divalent substituent derived from a monoheterocyclic or polyheterocyclic aromatic hydrocarbon containing 1 or more, preferably, 1 to 3 heteroatoms selected from N, O and S. Unless otherwise defined, heteroaryl means heteroaryl having 1 to 10 carbon cyclic rings, preferably, heteroaryl having 3 to 7 carbon cyclic rings, more preferably, heteroaryl having 3 to 5 carbon cyclic rings.

In the present invention, "substitution" may be, unless otherwise specified in the present invention, that at least one hydrogen atom is one kind to 3 kinds selected from the group consisting of a halogen atom (for example, F, Cl, Br, or I), a cyano group, a hydroxy group, a thiol group, a nitro group, an amino group, an imino group, an azido group, an amidino group, a hydrazino group, a hydrazono group, an oxo group, a carbonyl group, a carbamyl group, an ester group, an ether group, a carboxyl group or its salt, a sulfonate group or its salt, a phosphate or its salt, an alkyl group having 1-6 carbon atoms, a haloalkyl group having 1-6 carbon atoms, an alkenyl group having 2-6 carbon atoms, a haloalkenyl group having 2-6 carbon atoms, an alkynyl group having 2-6 carbon atoms, a haloalkynyl group having 2-6 carbon atoms, an alkoxy group having 1-6 carbon atoms, a haloalkoxy group having 1-6 carbon atoms, an alkylthio group having 1-6 carbon atoms, a heterocycloalkyl group having 1-9 carbon cyclic rings, a heterocycloalkyl group having 1-9 carbon cyclic rings, an aryl group having 6-10 carbon atoms, an aryloxy group having 6-10 carbon atoms, an arylthiol group having 6-10 carbon atoms, a heteroalkyl group having 1-9 carbon cyclic rings, a heteroaryloxy group having 1-9 carbon cyclic rings, and a heteroarylthio group having a carbon cyclic ring having 1 to 9 carbon atoms.

As one aspect, the present invention relates to a novel organic-based electron-transfer mediator represented by the structure of Chemical formula 1 below:

[Chemical formula 1]

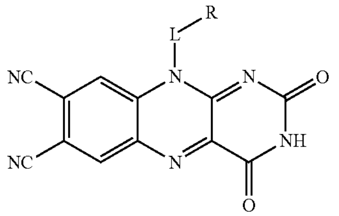

in the formula, R is —H, —F, —Cl, —Br, —I, —$NO_2$, —CN, —$CO_2H$, —$SO_3H$, —$NHNH_2$, —SH, —OH, —$NR_1R_2$, an unsubstituted or substituted alkyl group having 1 to 6 carbon atoms, an unsubstituted or substituted alkenyl group having 1 to 6 carbon atoms, or an unsubstituted or substituted aryl group having 6 to 10 carbon atoms, and the Ri and $R_2$ may be each independently H, alkyl having 1 to 3 carbon atoms, or —$COOR_3$, and the $R_3$ may be alkyl having 1 to 6 carbon atoms. Preferably, the $R_1$ and $R_2$ may be each independently H or Boc(t-butoxycarbonyl).

L (linker) may be one or more selected from the group consisting of a bond, a substituted or unsubstituted alkyl group having 1 to 20 carbon atoms, a substituted or unsubstituted alkenyl group having 1 to 20 carbon atoms, a substituted or unsubstituted ethylene oxide group having 2 to 50 carbon atoms, a substituted or unsubstituted ethylene amine group having 2 to 50 carbon atoms, a substituted or unsubstituted alkoxy group having 1 to 30 carbon atoms, a substituted or unsubstituted aryl or aryloxy group having 6 to 30 carbon atoms, or a substituted or unsubstituted heteroaryl group or heteroaryloxy group having 5 to 30 carbon atoms.

Preferably, the unsubstituted alkyl group having 1-20 carbon atoms in the L may be one or more kinds selected from the group consisting of a methyl group, an ethyl group, a propyl group, an isopropyl group, an n-butyl group, a sec-butyl group, a t-butyl group, a pentyl group, a hexyl group, a cyclohexyl group, a heptyl group, an octyl group and a decane group, but not limited thereto.

In addition, the substituted or unsubstituted ethylene oxide group having 2 to 50 carbon atoms may be one or more kinds selected from the group consisting of ethylene oxide groups in which the number of n in $(—OCH_2CH_2-)_n$ is 1-20, but not limited thereto.

The substituted or unsubstituted ethylene amine group having 2 to 50 carbo atoms may be one or more kinds selected from the group consisting of ethylene amine groups in which the number of n in $(—NHCH_2CH_2—)_n$ is 1-20, but not limited thereto.

The substituted or unsubstituted alkoxy group having 1 to 30 carbon atoms may be one selected from the group consisting of methoxy, ethoxy, propoxy, isopropoxy, butoxy, tert-butoxy, pentanoxy, hexanoxy, heptanoxy, octanoxy, decanoxy, alkyl-decanoxy (2-hexyl-1-decanoxy, 6-ethyl-3-decanoxy, etc.), dodecanoxy, alkyl-dodecanoxy, undecanoxy, alkyl-undecanoxy, allyloxy, cycloalkyloxy and cyclohexyloxy, but not limited thereto, and the alkyl of the alkyl-decanoxy, alkyl-dodecanoxy and alkyl-undecanoxy may be alkyl having 1 to 10 carbon atoms, alkyl having 1 to 8 carbon atoms or alkyl having 1 to 6 carbon atoms, but not limited thereto.

The substituted or unsubstituted aryl or aryloxy having 6 to 30 carbo atoms may be one selected from the group consisting of a phenyl group, a benzyl group, a tolyl group, a naphthalene group, a phenanthrene group, an alkyl phenyl group and a phenyloxy group, a benzyloxy group, a tolyloxy group, a naphthalene oxy group, a phenanthrene oxy group, and an alkoxyphenyl group, but not limited thereto.

The substituted or unsubstituted heteroaryl group or heteroaryloxy group having 5 to 20 carbon atoms may be one selected from the group consisting of monocyclics such as furyl, thiophenyl, pyrrolyl, imidazolyl, pyrazolyl, thiazolyl, thiadiazolyl, isothiazolyl, isooxazolyl, oxazolyl, oxadiazolyl, triazinyl, tetrazinyl, trazolyl, tetrazolyl, furazanyl, pyridyl, pyrazinyl, pyrimidinyl, pyridazinyl, and the like, and polycyclics such as heteroaryl, benzofuranyl, benzothiophenyl, isobenzofuranyl, benzoimidazolyl, benzothiazolyl, benzoisothiazolyl, benzoixoazolyl, benzooxazolyl, isoindolyl, indolyl, indazolyl, benzothiadiazolyl, quinolyl, isoquinolyl, quinoxalinyl, carbazolyl, phenanthridinyl and benzodioxolyl, but not limited thereto.

Specifically, the R may be —H, —F, —Cl, —Br, —I, $NO_2$, CN, $—CO_2H$, $—SO_3H$, $—NHNH_2$, —SH, —OH, $—NR_1R_2$, an unsubstituted or substituted alkyl group having 1 to 3 carbon atoms, an unsubstituted or substituted alkenyl group having 1 to 3 carbon atoms, or a phenyl group.

Specifically, the $R_1$ and $R_2$ may be each independently H or Boc (t-butoxycarbonyl).

Specifically, when the R is an alkyl group having 1 to 6 carbon atoms or an aryl group having 6 to 10 carbon atoms, they may be substituted to one or more, preferably, 1 to 3, more preferably, 1 or 2, selected from the group consisting of —OH, an alkyl group having 1 to 3 carbon atoms and an alkoxy group having 1 to 3 carbon atoms.

Specifically, the L may be one or more kinds selected from the group consisting of a bond, a substituted or unsubstituted alkylene having 1 to 8 carbon atoms, a substituted or unsubstituted alkenyl group having 1 to 6 carbon atoms, a substituted or unsubstituted ethylene oxide group having 2 to 6 carbon atoms, a substituted or unsubstituted ethylene amine group having 2 to 6 carbon atoms, a substituted or unsubstituted alkoxy group having 1 to 6 carbon atoms, a substituted or unsubstituted aryl or aryloxy group having 6 to 10 carbon atoms, or a substituted or unsubstituted heteroaryl group or heteroaryloxy group having 5 to 12 carbon atoms. Specifically, an alkylene having 1 to 8 carbon atoms, an alkenyl group having 1 to 6 carbon atoms, an ethylene oxide group having 2 to 6 carbon atoms, an ethylene amine group having 2 to 6 carbon atoms, an alkoxy group having 1 to 6 carbon atoms, an aryl group or aryloxy group having 6 to 10 carbon atoms, or a heteroaryl group or heteroaryloxy group of the L may be substituted to one or one or more, specifically, 1 to 3, or 1 or 2 substituents selected from the group consisting of halo, hydroxy, cyano, amino, alkyl having 1-4 carbon atoms, alkenylene having 2-4 carbon atoms and alkoxy groups having 1-4 carbon atoms.

As one preferable aspect, the -L-R may be one selected from the following structures, but not limited thereto.

H, $—CH_2CH_2CH_2SO_3H$,

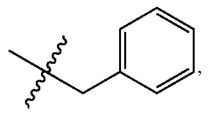 [SMILES: *Cc1ccccc1]

$—CH_2CH_2CH_2CH_2CH_2—NH(Boc)$, $—CH_2CH_2CH_2CH_2CH_2CH_2—NH(Boc)$, $—CH_2CH_2—OH$, $—CH_2CH_2—Cl$, $—CH_2CH_2CH_2CH_2CH_2—OH$, $—CH_3$ $OCH_3$ $CH_2CH_2OCH_2CH_2—OH$,

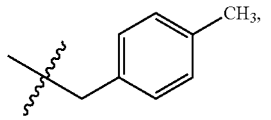

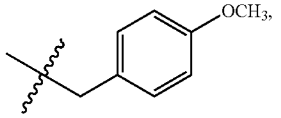

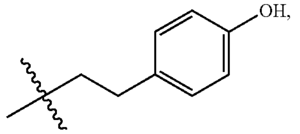

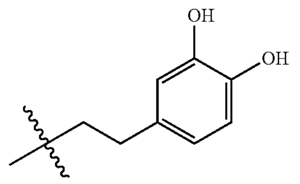

and $—CH_2—CH=CH_2$.

Preferably, the novel organic-based electron-transfer mediator represented by the structure of Chemical formula 1 may be compounds represented by the structure of any one chemical formula of the following Chemical formulas 2 to 16.

-continued
[Chemical formula 2]
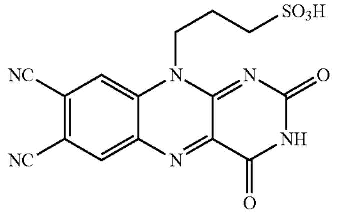
[Chemical formula 3]
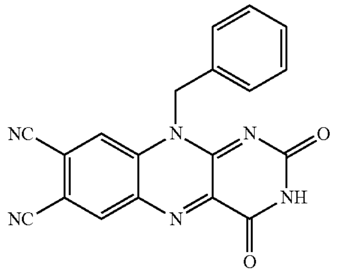
[Chemical formula 4]
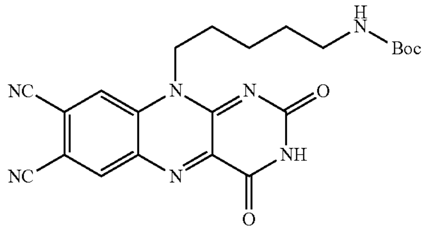
[Chemical formula 5]
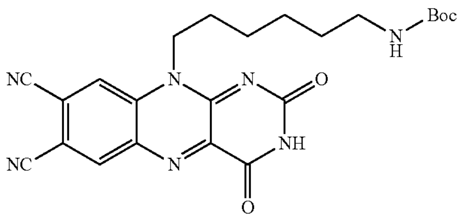
[Chemical formula 6]
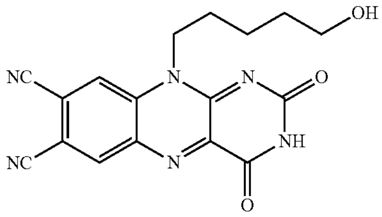
[Chemical formula 7]
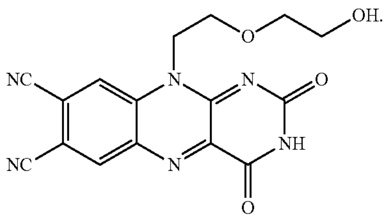
[Chemical formula 8]
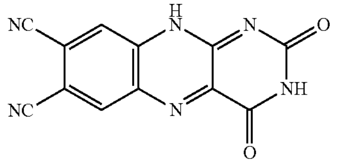
[Chemical formula 9]
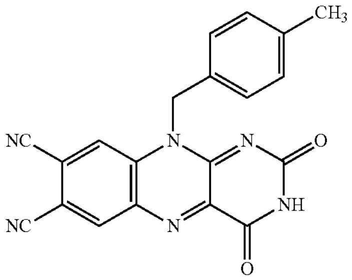
[Chemical formula 10]
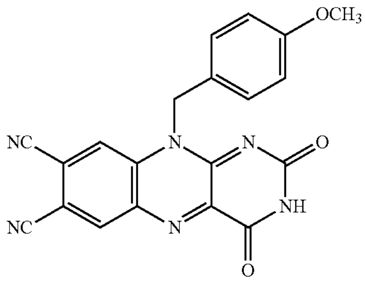
[Chemical formula 11]
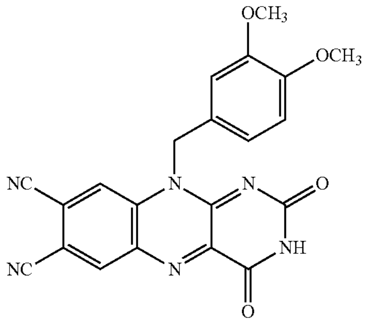
[Chemical formula 12]
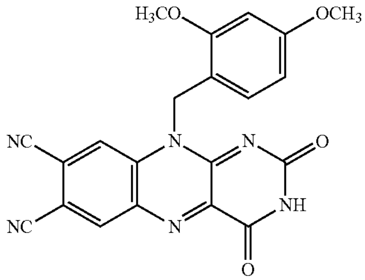
[Chemical formula 13]
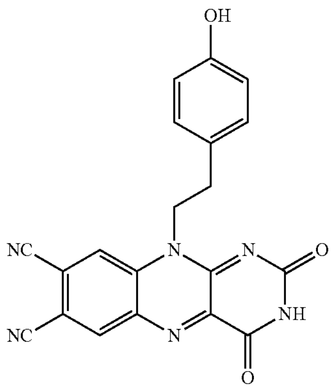

-continued

[Chemical formula 14]

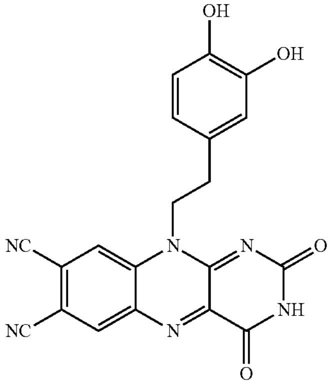

[Chemical formula 15]

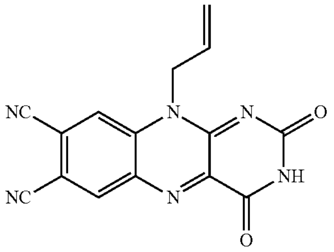

[Chemical formula 16]

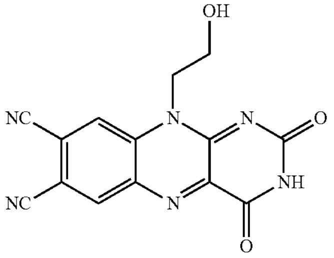

[Chemical formula 17]

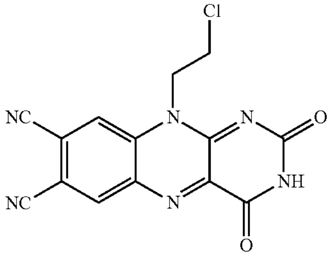

As other aspect, the present invention provides a method for preparation of the organic-based electron-transfer mediator of Chemical formula 1.

As one specific aspect, the method for preparation of the compound of Chemical formula 2 in the organic-based electron-transfer mediator of Chemical formula 1 according to the present invention may comprise the following steps:

i) reacting the compound of Chemical formula 18 with 1,3-propanesultone to obtain the compound of Chemical formula 19 below; and ii) reacting the compound of Chemical formula 19 obtained in the i) with alloxan monohydrate and boric acid to obtain the compound of Chemical formula 2 below.

[Chemical formula 18]

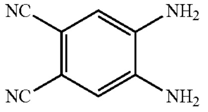

[Chemical formula 19]

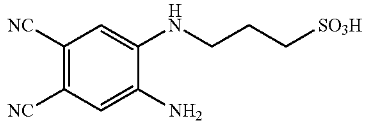

The method for preparation may be represented by Reaction formula 4 below.

[Reaction Formula 4]

Synthesis Method of Flavin Derivative (2)

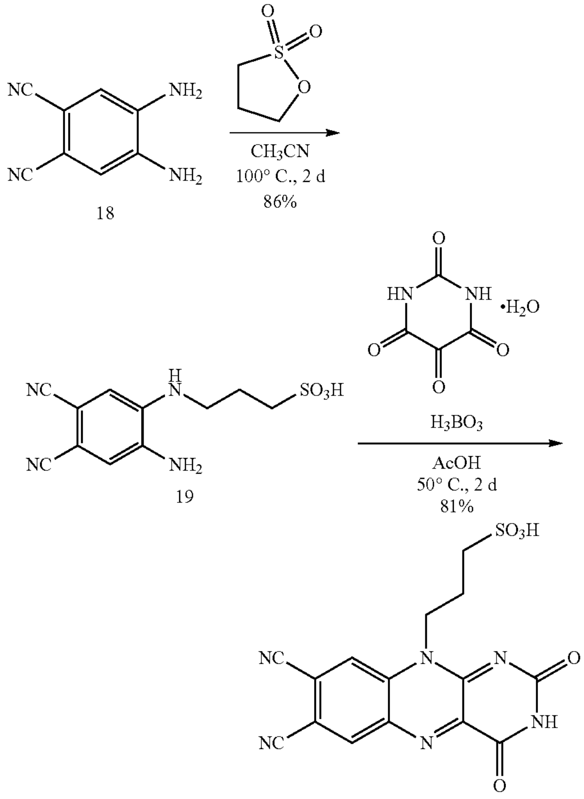

2

During the reaction of the i), in order to make it easier to separate the starting material and the resulting material, acetonitrile may be added to conduct the reaction. In addition, the amount of 1,3-propanesultone used may be 1.0 to 2.0 equivalents, preferably, 1.1 to 1.2 equivalents, compared to the compound of Chemical formula 18. The reaction temperature may be 50 to 120° C., 70 to 110° C. or 90 to 105° C., but not limited thereto, and it may be appropriately adjusted according to the reaction condition. The reaction time may be 2 days to 4 days.

In the ii), acetic acid may be added to conduct the reaction. In addition, the amount of alloxan monohydrate used may be 1.0 to 1.5 equivalents, preferably, 1.0 to 1.2 equivalents compared to the compound of Chemical formula 20, and the amount of boric acid used may be 0.5 to 2.0 equivalents, preferably, 1.0 to 1.2 equivalents, compared to the compound of Chemical formula 18. The reaction temperature may be 30 to 80° C., 40 to 70° C. or 50 to 60° C., but not limited thereto, and may be appropriately adjusted according to the reaction condition. The reaction time may be 2 hours or more, 4 hours or more, or 1 day or more, 2 days to 3 days.

As one specific aspect, the method for preparation of the organic-based electron-transfer mediator of Chemical formula 1 according to the present invention may comprise the following steps:

i) reacting 1,2-dibromo-4,5-difluorobenzene of Chemical formula 20 below with polymethylhydrosiloxane, and then reacting with Zn(CN)2 under tris(dibenzylideneacetone)dipalladium(0) {Pd2(dba)3} and 1,1'-bis(diphenylphosphino)ferrocene (DPPF) to obtain the compound of Chemical formula 20 below;

ii) reacting the compound of Chemical formula 21 obtained in the i) with ammonia water to obtain the compound of Chemical formula 22;

iii) reacting the compound of Chemical formula 22 obtained in the ii) with the compound of Chemical formula 23 to obtain the compound of Chemical formula 24; and iv) reacting the compound of Chemical formula 24 obtained in the iii) with alloxan monohydrate and boric acid to obtain the compound of Chemical formula 1.

[Chemical formula 20]

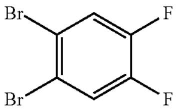

[Chemical formula 21]

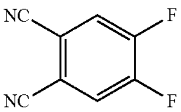

[Chemical formula 22]

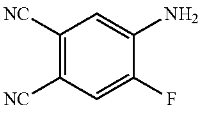

[Chemical formula 23]

$H_2N—L—R$

[Chemical formula 24]

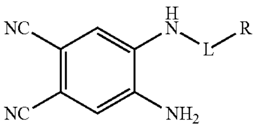

This method for preparation may be represented by Reaction formula 5 below.

[Reaction Formula 5]

Diamine structure using nucleophilic aromatic substitution reaction and flavin derivative synthesis method

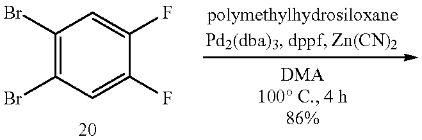

20

-continued

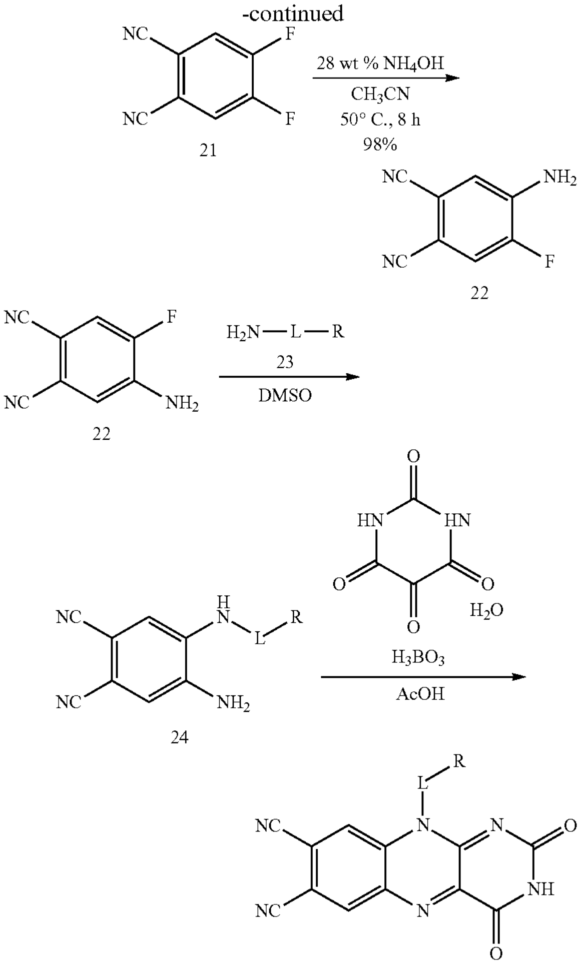

21, 22, 22, 24

1

This method for preparation synthesizes a derivative capable of introducing for water-soluble and polymer chains through the change of the amine structure using nucleophile aromatic substitution reaction between 4-amino-5-fluorophthalonitrile and chain amine, and by this method, as 1,2-dibromo-4,5-difluorobenzene of Chemical formula 20 is used instead of the expensive compound of Chemical formula 18 (4,5-diaminophthalonitrile), it has an advantage of having economical and high added value, and at the same time, synthesizing flavin derivatives having various terminal groups in the structure of the connection part.

The organic-based electron-transfer mediator according to the present invention plays a role of transferring electrons obtained as oxidoreductase is reduced (glucose oxidation), and it may be used in an oxidation-reduction polymer form connected to a polymer matrix corresponding to a polymer backbone such as one or more kinds selected from the group consisting of poly(vinylpyridine) (PVP) or poly(vinylimidazole) (PVI) and poly allyl glycidyl ether (PAGE).

Therefore, one additional aspect of the present invention, relates to an oxidation-reduction polymer comprising the organic-based electron-transfer mediator and a polymer backbone.

In one example, the oxidation-reduction polymer may comprise a linker structure connecting the polymer backbone and organic-based electron-transfer mediator.

In one example, the oxidation-reduction polymer may be represented by the structure of Chemical formula 25 below.

[Chemical formula 25]

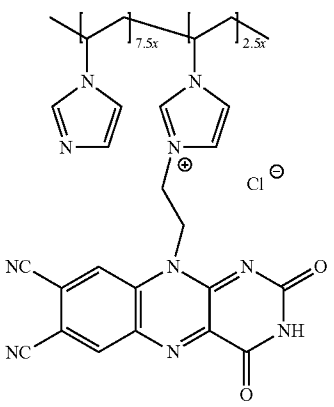

(In the formula, x may be 5 to 30)

In one example, the oxidation-reduction polymer of Chemical formula 25 may be prepared by the schematized method for preparation by Reaction formula 6 below.

[Reaction formula 6]

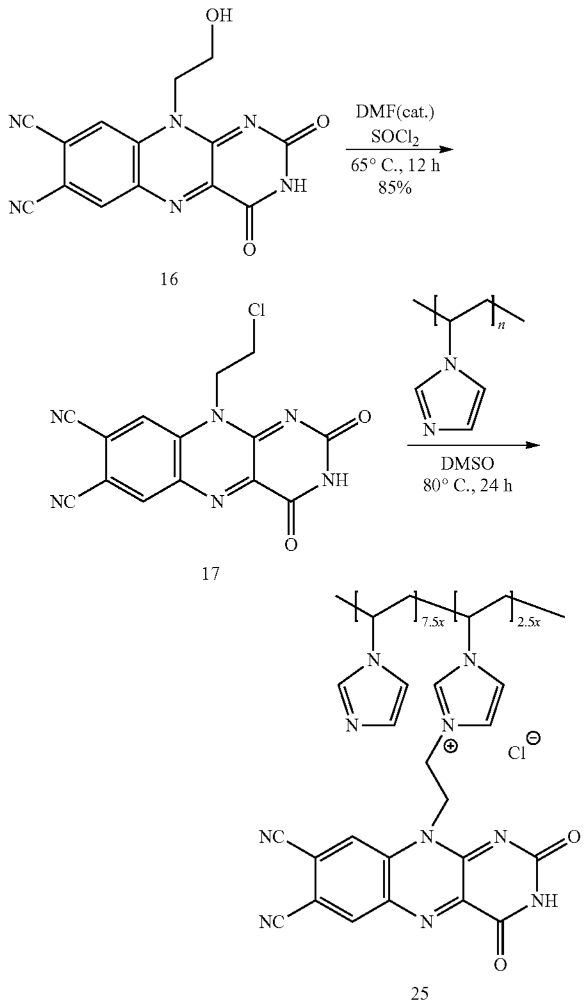

16

17

25

Specifically, the method for preparation uses a halogenation reaction of an alcohol using dimethylformamide of 10-(2-hydroxyethyl)-2,4-dioxo-2,3,4,10-tetrahydrobenzo[g]pteridine-7,8-dicarbonitrile represented by Chemical formula 16 as a catalyst of the reaction, as a method for introduction using reactivity between an electron-transfer mediator having a leaving group at the end and a nucleophile polymer. After that, after extracting an electron carrier having a good leaving group, chloride at the end using ethyl acetate and water, 10-(2-chloroethyl)-2,4-dioxo-2,3,4,10-tetrahydrobenzo[g]pteridine-7,8-dicarbonitrile represented by Chemical formula 17 through a precipitation method using dichloromethane can be synthesized. Then, after dissolving the synthesized substance of Chemical formula 17 in dimethylsulfoxide with polyvinylimidazole and heating at 80° C. for 24 hours, the compound of Chemical formula 25 can be finally obtained by a method for precipitating in ethyl acetate and dichloromethane.

As such, the oxidation-reduction polymer according to the present invention, is useful for various devices, in particular, an insertable continuous blood glucose measurement system.

In addition, one additional aspect of the present invention relates to a sensing layer for an electrochemical biosensor comprising an enzyme capable of conducting oxidation and reduction for a liquid biological sample and the organic-based electron-transfer mediator.

Oxidoreductase is a generic term for enzymes that catalyze an oxidation reduction reaction in a living body. In the present invention, it means an enzyme which is reduced by reacting with a target material to be measured, for example, a target material to be measured in case of a biosensor. The reduced enzyme reacts with an electron-transfer mediator as such, and the target material is quantified by measuring a signal such as a change in current generated at this time. The oxidoreductase usable in the present invention may be one or more kinds selected from the group consisting of various kinds of dehydrogenase, oxidase, esterase, and the like, and depending on the oxidation reduction or detection target material, an enzyme having the target material among the enzymes belonging to the enzyme group as a substrate may be selected and used.

More specifically, the oxidoreductase may be one or more kinds selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, bilirubin oxidase, and the like.

On the other hand, the oxidoreductase may comprise a cofactor playing a role of storing hydrogen stolen by the oxidoreductase from a target material to be measured (for example, target substance) together, and for example, it may be one or more kinds selected from the group consisting of flavin adenine dinucleotide (FAD), nicotinamide adenine dinucleotide (NAD), pyrroloquinoline quinone (PQQ), and the like.

For example, when a blood glucose concentration is to be measured, glucose dehydrogenase (GDH) as the oxidoreductase may be used, and the glucose dehydrogenase may be flavin adenine dinucleotide-glucose dehydrogenase (FAD-GDH) comprising FAD as a cofactor, and/or nicotinamide adenine dinucleotide-glucose dehydrogenase comprising FAD-GDH as a cofactor.

In a specific example, the usable oxidoreductase may be one or more kinds selected from the group consisting of FAD-GDH (for example, EC 1.1.99.10, etc.), NAD-GDH (for example, EC 1.1.1.47, etc.), PQQ-GDH (for example, EC1.1.5.2, etc.), glutamate dehydrogenase (for example, EC 1.4.1.2, etc.), glucose oxidase (for example, EC 1.1.3.4, etc.), cholesterol oxidase (for example, EC 1.1.3.6, etc.), cholesterol esterase (for example, EC 3.1.1.13, etc.), lactate oxidase (for example, EC 1.1.3.2, etc.), ascorbic acid oxidase (for example, EC 1.10.3.3, etc.), alcohol oxidase (for example, EC 1.1.3.13, etc.), alcohol dehydrogenase (for example, EC 1.1.1.1, etc.), bilirubin oxidase (for example, EC 1.3.3.5, etc.), and the like.

Most preferably, the oxidoreductase is glucose dehydrogenase capable of maintaining the activity of 70% or more in a 37° C. buffer solution for 1 week.

The sensing layer according to the present invention may contain 20 to 700 parts by weight, for example, 60 to 700 parts by weight or 30 to 340 parts by weight of the oxidation-reduction polymer based on 100 parts by weight of the oxidoreductase. The content of the oxidation-reduction polymer may be appropriately adjusted according to the activity of the oxidoreductase.

Furthermore, the sensing layer according to the present invention may further comprise a carbon nanotube for an increase of the membrane performance. Specifically, the carbon nanotube may further increase the performance of the sensing layer as the electron-transfer rate is increased when using a transition metal complex, particularly, osmium.

In addition, the sensing layer according to the present invention may further comprise a crosslinking agent.

On the other hand, the sensing layer according to the present invention may further comprise one or more kinds of additives selected from the group consisting of a surfactant, a water-soluble polymer, a tertiary ammonium salt, a fatty acid, a thickener, and the like, for a role of a dispersing agent for dissolving a reagent, an adhesive for preparing a reagent, a stabilizer for long-term storage.

The surfactant may play a role to distribute the composition evenly over the electrode and aliquot it in a unique thickness when aliquoting the composition. As the surfactant, one or more kinds selected from the group consisting of Triton X-100, sodium dodecyl sulfate, perfluorooctane sulfonate, sodium stearate and the like may be used. The reagent composition according to the present invention may contain the surfactant in an amount of 3 to 25 parts by weight, for example, 10 to 25 parts by weight, based on 100 parts by weight of the oxidoreductase, in order to make a reagent to appropriately perform a role of distributing the reagent evenly on the electrode and aliquoting the reagent in a unique thickness, when the reagent is aliquoted. For example, when using oxidoreductase with the activity of 700 U/mg, it may contain 10 to 25 parts by weight of the surfactant based on 100 parts by weight of the oxidoreductase, and when the activity of the oxidoreductase is higher than this, the content of the surfactant may be adjusted lower than this.

The water-soluble polymer may perform a role of helping stabilization and dispersing of an enzyme as a polymer support of the reagent composition. As the water-soluble polymer, one or more kinds selected from the group consisting of polyvinyl pyrrolidone (PVP), polyvinyl alcohol (PVA), polyperfluoro sulfonate, hydroxyethyl cellulose (HEC), hydroxypropyl cellulose (HPC), carboxy methyl cellulose (CMC), cellulose acetate, polyamide, and the like may be used. The reagent composition according to the present invention may contain the water-soluble polymer in an amount of 10 to 70 parts by weight, for example, 30 to 70 parts by weight based on 100 parts by weight of the oxidoreductase, in order to sufficiently and appropriately exhibiting a role of helping stabilization and dispersing of oxidoreductase. For example, when using oxidoreductase with the activity of 700 U/mg, it may contain 30 to 70 parts by weight of the water-soluble polymer based on 100 parts by weight of the oxidoreductase, and when the activity of the oxidoreductase is higher than this, the content of the water-soluble polymer may be adjusted lower than this.

The water-soluble polymer may have a weight average molecular weight of about 2,500 g/mol to 3,000,000 g/mol, for example, about 5,000 g/mol to 1,000,000 g/mol, in order to effectively perform a role of helping stabilization and dispersing of the support and enzyme.

The thickener plays a role of hardly attaching a reagent on an electrode. As the thickener, one or more kinds selected from the group consisting of natrosol, diethylaminoethyl-dextran hydrochloride (DEAE-Dextran hydrochloride), and the like may be used. The electrochemical sensor according to the present invention may contain the thickener in an amount of 10 to 90 parts by weight, for example, 30 to 90 parts by weight, based on 100 parts by weight of the oxidoreductase, in order to make the oxidation-reduction polymer according to the present invention is hardly attached on an electrode. For example, when using oxidoreductase with the activity of 700 U/mg, it may contain 30 to 90 parts by weight of the thickener based on 100 parts by weight of the oxidoreductase, and when the activity of the oxidoreductase is higher than this, the content of the thickener may be adjusted lower than this.

As other aspect, the present invention may be a device, preferably, an insertable device, comprising this organic electron-transfer mediator. In addition, preferably, the device may be an electrochemical biosensor, and more preferably, it may be an electrochemical glucose (blood glucose) sensor.

Specifically, the type of the electrochemical biosensor is not limited, but preferably, it may be a continuous blood glucose monitoring sensor.

As the composition of this continuous blood glucose monitoring sensor, the present invention, may comprise for example, a n electrode, an insulator, a substrate, a sensing layer comprising the oxidation-reduction polymer and oxidoreductase, a diffusion layer, a protection layer, and the like. The electrode may comprise two kinds of electrodes such as a working electrode and a counter electrode, and may comprise 3 kinds of a working electrode, a counter electrode, and a reference electrode. In one embodiment, the biosensor according to the present invention may be an electrochemical biosensor prepared by applying a reagent composition comprising an oxidation-reduction polymer comprising the organic-based electron-transfer mediator of Chemical formula 1 and an enzyme capable of conducting oxidation reduction for a liquid biological sample on a substrate having at least two, preferably, two or three electrodes, and drying. For example, a planar electrochemical biosensor characterized in that a working electrode and a counter electrode are equipped on opposite sides of a substrate each other, and a sensing layer comprising an oxidation-reduction polymer having the organic-based electron-transfer mediator according to the present invention is laminated on the working electrode, and an insulator, a diffusion layer and a protection layer are laminated in order on both sides of the substrate equipped with the working electrode and counter electrode, in the electrochemical biosensor.

As a specific aspect, the substrate may be made of one or more kinds of materials selected from the group consisting of PET (polyethylene terephthalate), PC (polycarbonate) and PI (polyimide).

In addition, as the working electrode, a carbon, gold, platinum, silver or silver/silver chloride electrode may be used.

Furthermore, in case of an electrochemical biosensor having 2 electrodes, a counter electrode also plays a role of a reference electrode, and therefore, as a counter electrode, a gold, platinum, silver or silver/silver chloride electrode may be used, and in case of an electrochemical biosensor of 3 electrodes also comprising a reference electrode, as a reference electrode, a gold, platinum, silver or silver/silver chloride electrode may be used, and a counter electrode, a carbon electrode may be used.

As the diffusion layer, Nafion, cellulose acetate or silicone rubber may be used, and as the protection layer, silicone rubber, polyurethane, polyurethane-based copolymer, or the like may be used, but not limited thereto.

As a non-limiting example, as a counter electrode also plays a role of a reference electrode in case of 2 electrodes, silver chloride or silver may be used, and in case of 3 electrodes, as a reference electrode, silver chloride or silver may be used, and as a counter electrode, a carbon electrode may be used.

A specific example of the present invention illustrates a biosensor for measuring glucose as an applicable example of an electrochemical biosensor, but it may be applied for a biosensor for quantifying various materials such as cholesterol, lactate, creatinine, hydrogen peroxide, alcohol, amino acid and glutamate, by differing the kind of the enzyme comprised in the reagent composition of the present invention.

MODE FOR INVENTION

Hereinafter, the present invention will be described in more detail by the following examples. However, the following examples are intended to illustrate the present invention only, but the contents of the present invention are not limited by the following examples.

EXAMPLE

Preparative Example 1: Synthesis of 3-[(2-amino-4,5-dicyano)phenylamino]propane-1-sulfonic acid [Chemical formula 19]

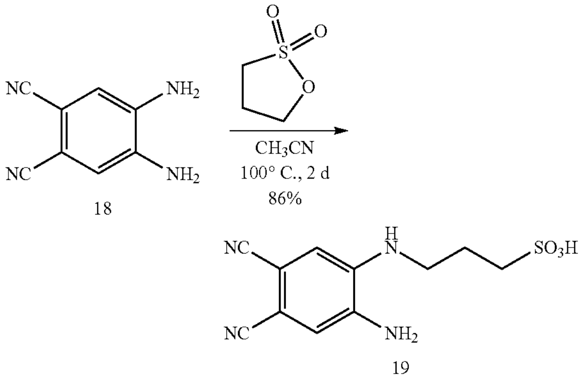

18
19

In a glass culture tube having a magnetic stirrer, 4,5-diaminophthalonitrile [Chemical formula 18] (0.5 g, 3.16 mmol) and 1,3-propanesultone (463.3 mg, 3.79 mmol), and acetonitrile (5.0 mL) were added at a room temperature. The reaction mixture was stirred at 100° C. for 2 days. After cooling to the room temperature, the precipitated solid was filtered. The filtered solid was dissolved in methanol again and undissolved impurities were removed, and then the solvent was removed using a rotary evaporative condenser to obtain a light brown solid product; 0.768 g (86%)

$^1$H NMR (400 MHz, DMSO): δ 6.85 (s, 1H), 6.81 (s, 1H), 3.22 (t, 2H), 2.57 (t, 2H), 1.89 (m, 2H).

$^{13}$C NMR (400 MHz, DMSO): δ 138.26, 138.63, 118.11, 117.98, 114.50, 111.23, 102.01, 101.10, 49.23, 42.03, 24.14.

FT-IR (KBr pellet): 3323(m), 3062(m), 2940(m), 2618 (m), 2228(m), 1626(s), 1519(w), 1492(w), 1379(w), 1957 (m), 1198(s), 1172(s), 1149(s), 1044(s), 729(w) $cm^{-1}$

Preparative Example 2: 3-(7,8-dicyano-2,4-dioxo-3,4-dihydrobenzo[g]pteridin-10(2H)-yl)propane-1-sulfonic acid) [Chemical formula 2]

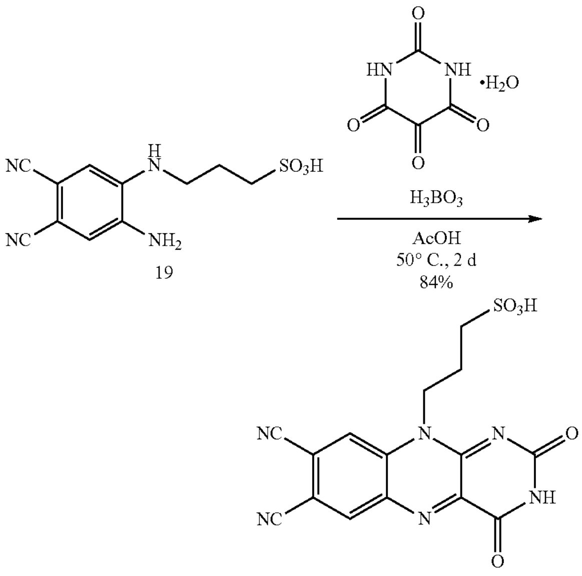

19
2

In a 100 ml round bottom flask, 3-[(2-amino-4,5-dicyano)phenylamino]propane-1-sulfonic acid (19) (1.5 g, 5.35 mmol), alloxan monohydrate (0.942 g, 5.885 mmol) and boric acid (0.363 g, 5.885 mmol) were added and acetate (15 ml) was added. Under the nitrogen atmosphere, the reaction mixture was stirred at 50° C. for 2 days, and the produced yellow solid was filtered. The filtered solid was dissolved in acetonitrile and undissolved impurities were filtered to obtain a yellow solid; 1.73 g (84%)

$^1$H NMR (400 MHz, DMSO): δ 11.67 (s, 1H), 8.96 (s, 1H), 8.92 (s, 1H), 3.61 (t, 2H), 2.65 (t, 2H), 2.00 (m, 2H).

$^{13}$C NMR (100 MHz, DMSO): δ 159.08, 155.55, 151.20, 142.83, 137.50, 135.72, 135.65, 123.48, 117.74, 115.50, 115.39, 109.94, 47.84, 44.07, 22.71

FT-IR (KBr pellet): 3430(m), 3055(m), 2239(w), 1722 (m), 1680(m), 1589(m), 1551(s), 1525(m), 1404(m), 1175 (m), 1043(m) $cm^{-1}$ Preparative Example 3: 4,5-difluorophthalonitrile [Chemical formula 21]

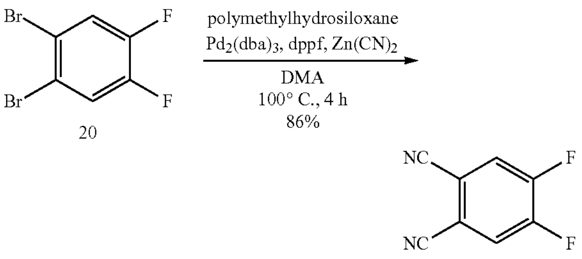

20

21

In a 50 mL glass culture tube having a magnetic stirrer, 1,2-dibromo-4,5-difluorobenzene (2.0 g, 7.40 mmol) was dissolved in dimethylacetamide 5.0 mL. At a room temperature, polyhydromethylsiloxane was added, and then at the temperature, $Pd_2(dba)_3$ (144 mg, 0.158 mmol) and dppf (120 mg, 0.216 mmol) were added. After adding $Zn(CN)_2$ (1.87 g, 14.8 mmol), the reactants on the wall side were washed with 5.0 mL dimethylacetamide. The reaction mixture was stirred at 100° C. for 4 hours, and then was cooled to a room temperature. After diluting the reaction mixture with dichloromethane and then filtering solid precipitates, it was extracted using water and dichloromethane. The organic layer was collected and washed with saturated NaCl aqueous solution, and then anhydrous Na—$_2SO_4$ was added and the remaining water was removed. The drying agent was filtered with a glass filter, and the solvent was removed at maximum using a rotary evaporative condenser. After purifying using column chromatography using a developing solution having the composition of Hexane:EtOAc=4:1 (Rf=0.34), it was recrystallized with hexane to obtain a white solid; 1.04 g (86%)

$^1$H NMR (400 MHz, $CDCl_3$): δ. 7.69 (t, 2H, J=8.0 Hz)

$^{13}$C NMR (100 MHz, $CDCl_3$): δ. 154.30 (d), 151.66 (d), 123.83-123.35 (sextet), 113.71 (t)

$^{19}$F NMR (375 MHz, $CDCl_3$): δ. 123.45

Preparative Example 4: 4-amino-5-fluorophthalonitrile [Chemical formula 22]

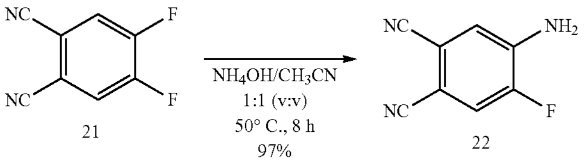 [SMILES: N#Cc1cc(F)c(F)cc1C#N ; N#Cc1cc(N)c(F)cc1C#N]

21

22

In a 50 mL glass culture tube having a magnetic stirrer, 4,5-difluorobenzene (1.0 g, 6.09 mmol) was dissolved in acetonitrile (3.0 mL), and then 28 wt % ammonia water (3.0 mL) was added and stirred at a room temperature. It was stirred at 50° C. for 8 hours, and whether the reaction is completed was confirmed by thin film chromatography ($Rf_{starting\ material}$=0.66, $Rf_{resulting\ material}$=0.34) using a developing solution of Hex:EA=1:1. After diluting by adding water to the reaction mixture, it was extracted using ethyl acetate three times. The organic layer was collected and washed with saturated NaCl aqueous solution, and then anhydrous $Na_2SO_4$ was added to remove the remaining water. The drying agent was filtered with a glass filter and the solvent was removed using a rotary evaporative condenser to obtain a white solid; 0.95 g (97%)

$^1$H NMR (400 MHz, DMSO): δ 7.86 (d, J=11.2, 1H), 7.23 (d, J=8.0, 1H), 6.83 (s, 2H)

$^{13}$C NMR (100 MHz, DMSO): δ 150.59, 142.27, 142.27, 120.55, 119.51, 116.47, 115.95, 112.16, 98.68

$^{19}$F NMR (375 MHz, DMSO): δ −125.32

FT-IR (KBr pellet): 3562(m), 3425(m), 3342(m), 3230 (m), 3060(m), 2229(m), 1654(m), 1605(m), 1658(m), 1439 (m), 1362(m), 1258(m), 1232(m) 894(m)

Anal. Calcd for $C_8H_4FN_3$: C, 59.63; H, 2.50; F, 11.79; N, 26.08. Found: C, 59.59; H, 2.61; N, 26.10.

Preparative Example 5: 4-amino-5-benzylaminophthalonitrile (3a)

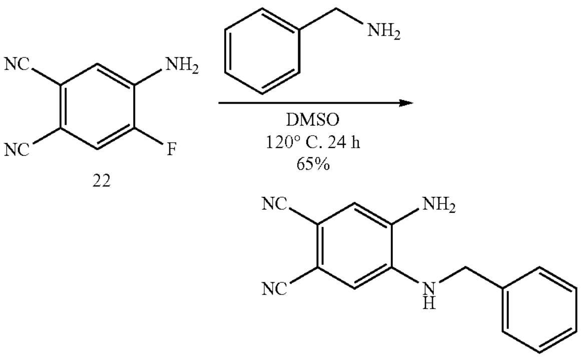

22

3a

In a 10 mL glass culture tube having a magnetic stirrer, 4-amino-5-fluorophthalonitrile (22) (200 mg, 1.24 mmol) was dissolved in dimethylsulfoxide 1.0 ml, and then purified benzylamine (0.136 mL, 1.24 mmol, 1.0 equiv.) was added using distillation under reduced pressure. The reaction mixture was stirred at 120° C. for 24 hours under the nitrogen atmosphere. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $MgSO_4$, and then the drying agent was filtered with a glass filter and the solvent was removed using a rotary evaporative condenser at maximum. After purifying by column chromatography using a developing solution having the composition of Hexane:EtOAc=1:1 (Rf=0.30), it was recrystallized with toluene to obtain a light yellow solid; 210 mg (68%)

$^1$H NMR (400 MHz, DMSO): δ 7.35 (m, 4H), 7.27 (m, 1), 6.90 (s, 1H), 6.77 (s, 1H), 6.46 (t, 1H, J=5.4 Hz), 6.09 (s, 2H), 4.44 (d, J=5.4 Hz, 2H).

$^{13}$C NMR (400 MHz, DMSO): δ 140.16, 138.84, 138.58, 128.94, 127.78, 127.580, 118.45, 118.20, 115.16, 112.34, 102.20, 101.98, 46.39

Preparative Example 6: 10-benzyl-7,8-dicyanoisoalloxazine [Chemical formula 3]

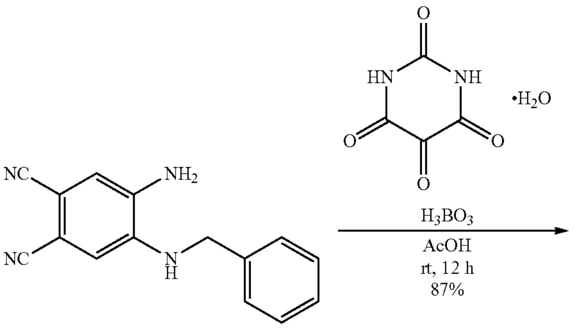

3a

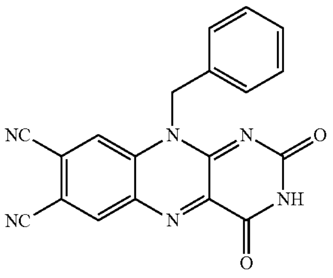

3

In a 10 ml round bottom flask, 4-amino-5-benzylaminophthalonitrile (3a) (100 mg, 0.403 mmol), alloxan monohydrate (70.9 mg, 0.443 mmol 1.1 equiv.) and boric acid (28 mg, 0.451 mmol 1.12 equiv.) were added and acetate (6 ml) was added. The reaction mixture was stirred at a room temperature for 2 hours and the produced yellow solid was filtered. The filtered solid was washed with water and ethyl ether, and hexane to obtain a yellow solid; 124 mg (87%)

$^1$H NMR (400 MHz, DMSO): δ 11.73 (s, 1H), 8.93 (s, 1H), 8.44 (s, 1H), 7.31 (m, 5H), 5.83 (s, 2H).

$^{13}$C NMR (100 MHz, DMSO): δ 159.43, 155.84, 152.02, 143.87, 137.84, 136.03, 135.89 134.28, 129.07, 128.12, 127.34, 123.41, 117.93, 115.77, 115.60, 110.73, 47.69.

Preparative Example 7: tert-butyl (5-((2-amino-4,5-dicyanophenyl)amino)pentyl)carbamate (4a)

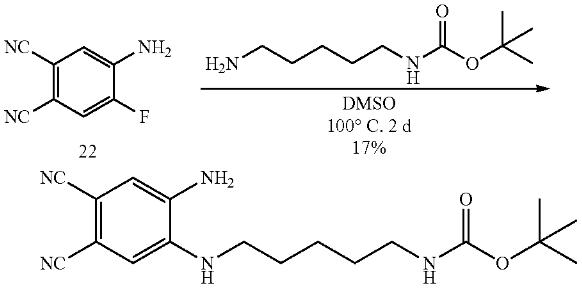

4a

In a 10 mL glass culture tube having a magnetic stirrer, 4-amino-5-fluorophthalonitrile (22) (100 mg, 0.620 mmol) was dissolved in dimethylsulfoxide 1.0 ml, and then N-1, 5-diaminopentane (125 mg, 0.620 mmol, 1.0 equiv.) was added. The reaction mixture was stirred at 100° C. for 48 hours under the nitrogen atmosphere. The reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $MgSO_4$, and then the drying agent was filtered with a glass filter and the solvent was removed using a rotary evaporative condenser at maximum. After purifying by column chromatography using a developing solution having the composition of Hexane: EtOAc=1:1 (Rf=0.11), a transparent foam solid was obtained; 37 mg (17%)

$^1$H NMR (400 MHz, $CDCl_3$): δ 6.90 (s, 1H), 6.74 (s, 1H), 4.69 (s, 1H), 4.25 (s, 1H), 4.22 (s, 2H), 3.15 (dd, J=11.8, 6.2 Hz, 4H), 1.79-1.64 (m, 2H), 1.62-1.47 (m, 4H), 1.45 (d, J=12.4 Hz, 9H).

$^{13}$C NMR (100 MHz, $CDCl_3$): δ 156.43, 140.33, 137.649, 117.61, 117.34, 117.288, 112.99, 106.61, 103.54, 79.38, 43.47, 39.91, 30.00, 28.42, 28.22, 24.02

Preparative Example 8: tert-butyl (5-(7,8-dicyano-2, 4-dioxo-3,4-dihydrobenzo[g]pteridin-10(2H)-yl) pentyl)carbamate [Chemical formula 4]

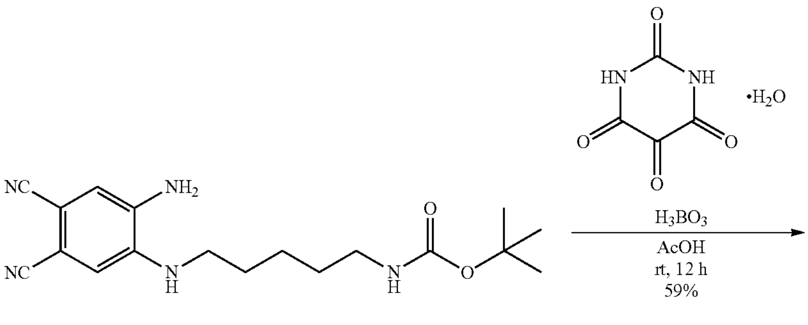

4a

-continued

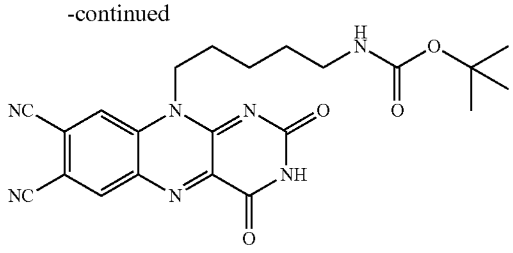

4

In a 10 ml round bottom flask, to tert-butyl-N-[5-(2-Amino-4,5-dicyanophenylamino)-pentyl]carbamate (37 mg, 0.11 mmol) dissolved in acetate (1 mL), alloxan monohydrate (19.4 mg, 0.121 mmol 1.1 equiv.) and boric acid (7.5 mg, 0.121 mmol 1.1 equiv.) were dissolved in acetate (2 ml) and added. The reaction mixture was stirred at a room temperature for 12 hours, and the temperature was lowered to 0° C., and then the produced yellow solid was filtered. The filtered solid was washed with water and 0° C. ethyl ether to obtain a yellow solid; 29 mg (59%)

$^1$H NMR (400 MHz, DMSO): δ 11.67 (s, 1H), 8.93 (s, 1H), 8.79 (s, 11H), 6.80 (t, 1H, J=2.0 Hz), 4.49 (t, 2H), 2.928 (d, 2H, J=5.6 Hz), 1.671 (s, 2H), 1.368 (m, 4H) ESI-MS 450.250

Preparative Example 9: tert-butyl (6-((2-amino-4,5-dicyanophenyl)amino)hexyl)carbamate (5a)

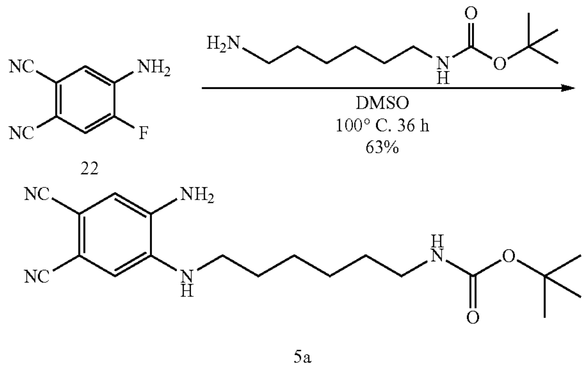

22

5a

In a 10 mL glass culture tube having a magnetic stirrer, 4-amino-5-fluorophthalonitrile (22) (100 mg, 0.62 mmol) was dissolved in dimethylsulfoxide 1.0 ml, and then N-1,6-diaminohexane (160.9 mg, 0.744 mmol, 1.2 equiv.) was added. The reaction mixture was stirred at 100° C. for 36 hours. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $MgSO_4$, and then the drying agent was filtered with a glass filter and the solvent was removed using a rotary evaporative condenser at maximum. After purifying by column chromatography using a developing solution having the composition of Hexane:EtOAc=1:2 (Rf=0.50) to obtain a transparent foam solid; 140 mg (63%)

$^1$H NMR (400 MHz, $CDCl_3$): δ 6.74 (s, 1H), 6.71 (s, 1H), 4.68 (s, 1H), 4.49 (s, 1H), 4.36 (s, 2H), 3.14 (s, 4H), 1.66 (t, 2H, J=6 Hz), 1.49-1.34 (m, 15H)

$^{13}$C NMR (100 MHz, $CDCl_3$): δ 156.455, 140.048, 137.895, 117.549, 117.504, 117.273, 112.633, 106.087, 103.056, 79.358, 42.813, 39.566, 29.906, 28.424, 28.223, 25.639, 25.400

Preparative Example 10: tert-butyl (6-(7,8-dicyano-2,4-dioxo-3,4-dihydrobenzo[g]pteridin-10(2H)-yl)hexyl)carbamate [Chemical formula 5]

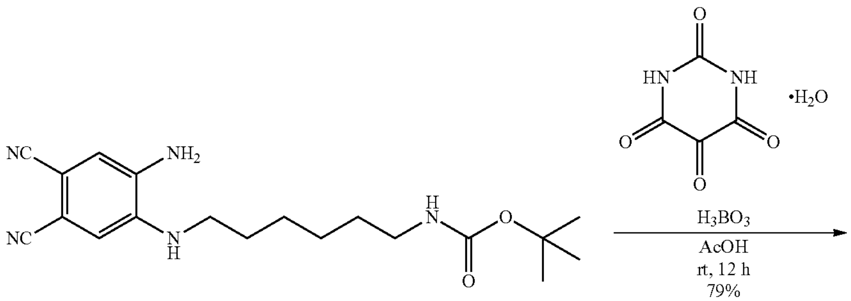

5a

-continued

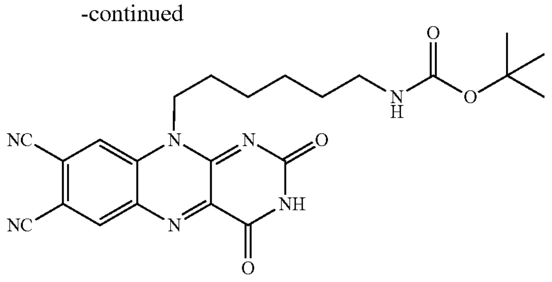

5

In a 10 ml round bottom flask, to tert-butyl (6-((2-amino-4,5-dicyanophenyl)amino)hexyl)carbamate (5a) (100 mg, 0.280 mmol) dissolved in acetate (1 mL), alloxan monohydrate (49.3 mg, 0.308 mmol 1.1 equiv.) and boric acid (19.4 mg, 0.314 mmol 1.12 equiv.) were dissolved in acetate (3 ml) and added. The reaction mixture was stirred at a room temperature for 12 hours, and the temperature was lowered to 0° C., and then the produced yellow solid was filtered. The filtered solid was washed with water and 0° C. ethyl ether, hexane to obtain a yellow solid; 102 mg (79%)

$^1$H NMR (400 MHz, DMSO): δ. 11.68 (s, 1H), 8.93 (s, 1H), 8.78 (s, 1H), 7.78 (t, 1H, J=5.2 Hz), 4.50 (s, 2H), 2.89 (dd, 2H, J=12.7, 6.5 Hz), 1.67 (br, 2H) 1.51-1.18 (m, 15H)

$^{13}$C NMR (100 MHz, DMSO): δ. 159.41, 156.00, 155.87, 151.45, 143.23, 137.90, 135.93, 135.88, 123.73, 118.06, 115.92, 115.71, 110.25, 77.742, 45.05, 29.84 28.71, 26.78, 26.55, 26.10, 21.51

Preparative Example 11:
4-amino-5-(5-hydroxypentyl)phthalonitrile (6a)

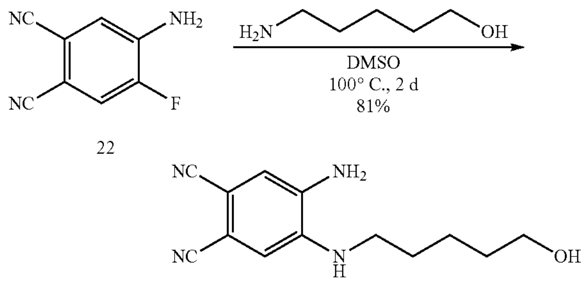

22

6a

In a 10 mL glass culture tube having a magnetic stirrer, 4-amino-5-fluorophthalonitrile (22) (500 mg, 3.10 mmol) was dissolved in dimethylsulfoxide 5.0 ml, and then 5-amino-pentan-1-ol (0.405 mL, 3.72 mmol, 1.2 equiv.) was added. The reaction mixture was stirred at 100° C. for 48 hours. The cooled reaction mixture was diluted using ethyl acetate at a room temperature and the organic layer was washed with water to remove dimethylsulfoxide. The collected organic layer was washed with saturated NaCl aqueous solution, and the remaining water was removed with anhydrous $MgSO_4$, and then the drying agent was filtered with a glass filter and the solvent was removed using a rotary evaporative condenser at maximum. After dissolving the solid mixture in a small amount of permethyl alcohol, hexane was added little by little, and the precipitated solid was filtered and dried under reduced pressure to obtain an ivory solid; 612 mg (81%)

$^1$H NMR (400 MHz, DMSO): δ 6.84 (s, 1H) 6.79 (s, 1H), 5.98 (s, 2H) 5.70 (t, J=4.8 Hz, 1H) 4.37 (t, J=5.2 Hz, 1H), 3.38 (dd, 2H, J=11.5, 6.2 Hz), 3.10 (dd, J=12.2, 6.8 Hz, 2H), 1.47-1.32 (m, 4H)

$^{13}$C NMR (100 MHz, DMSO): δ. 139.76, 138.97, 131.11, 118.55, 114.71, 111.57, 102.29, 101.54, 61.09, 43.24, 32.59, 28.40, 23.66

Anal. Calcd for $C_{13}H_{16}N_4O$: C, 63.91; H, 6.60; N, 22.93; 0, 6.55. Found: C, 63.94; H, 22.97; N, 22.97.

Preparative Example 12: 10-(5-hydroxypentyl)-2,4-dioxo-2,3,4,10-tetrahydrobenzo[g]pteridine-7,8-dicarbonitrile [Chemical formula 6]

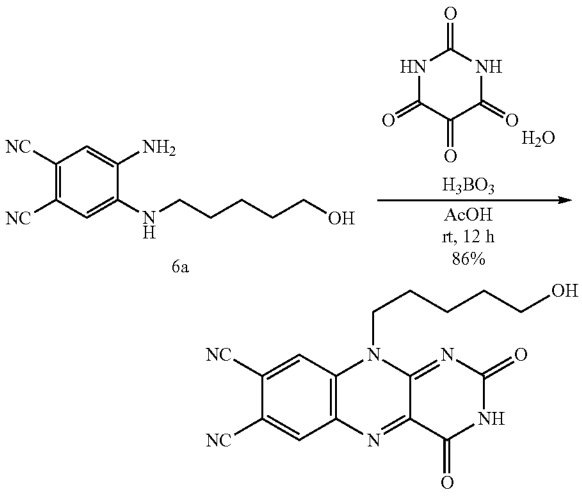

6a

6

In a 10 ml round bottom flask, to 4-amino-5-(5-hydroxypentyl)phthalonitrile (6a) (100 mg, 0.409 mmol) dissolved in acetate (1 mL), alloxan monohydrate (66.8 mg, 0.417 mmol 1.02 equiv.) and boric acid (25.8 mg, 0.417 mmol 1.02 equiv.) were added as a suspending solution. The reaction mixture was stirred at a room temperature for 12 hours and the precipitated yellow solid was filtered. The filtered solid was washed with ethyl ether, chloroform and hexane to obtain a yellow solid; 123 mg (86%)

$^1$H NMR (400 MHz, DMSO): δ 11.67 (s, 1H), 8.91 (s, 1H), 8.78 (s, 1H), 4.49 (br, 2H), 4.43 (t, 1H, J=5.0 Hz), 3.40 (s, 2H), 1.66 (s, 2H), 1.46 (s, 4H)

$^{13}$C NMR (100 MHz, DMSO): δ. 159.40, 155.87, 151.39, 143.17, 137.88, 135.86, 123.77, 118.05, 115.91, 115.69, 110.26, 60.97, 40.49, 45.17, 32.65, 26.66, 23.11.

Preparative Example 13: 4-amino-5-[2-(2-hydroxy-ethoxy)-ethyl]-phthalonitrile (7a)

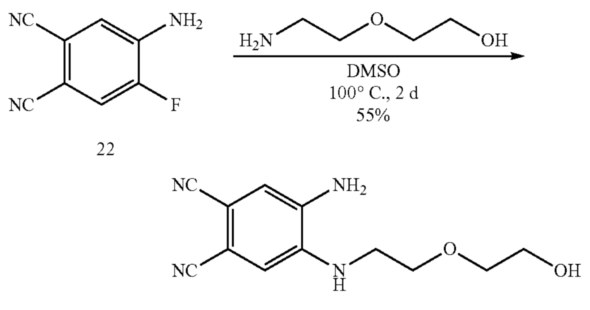

22

7a

In a 10 mL glass culture tube having a magnetic stirrer, 4-amino-5-fluorophthalonitrile (22) (100 mg, mmol) was dissolved in dimethylsulfoxide 1.0 ml, and then 2-(2-aminoethoxy)ethanol (0.075 ml, 0.744 mmol, 1.2 equiv.) was added. The reaction mixture was stirred at 100° C. for 48 hours. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $MgSO_4$, and then the drying agent was filtered with a glass filter and the solvent was removed using a rotary evaporative condenser at maximum. The solid mixture was dissolved in ethyl acetate, and then dichloromethane and hexane were added to filter the precipitated solid and dry it under reduced pressure, to obtain an ivory solid; 84 mg (55%)

$^1$H NMR (400 MHz, DMSO): δ. 6.90 (s, 1H), 6.88 (s, 1H), 6.03 (s, 2H), 5.81 (t, 1H, J=4.8 Hz), 4.65 (br, 1H), 3.61 (t, 2H, J=5.2 Hz), 3.52 (m, 2H), 3.46 (t, 2H, J=4.8 Hz), 3.34 (m, 2H)

$^{13}$C NMR (100 MHz, DMSO): δ. 139.94, 138.88, 118.51, 118.31, 114.99, 111.95, 102.24, 101.89, 72.64, 68.77, 60.63, 43.13

Preparative Example 14: 10-(2-(2-hydroxyethoxy)ethyl)-2,4-dioxo-2,3,4,10-tetrahydrobenzo[g]pteridine-7,8-dicarbonitrile [Chemical formula 7]

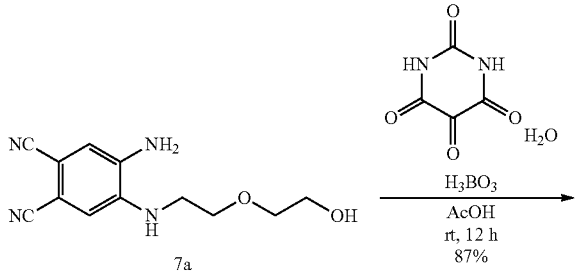

7a

-continued

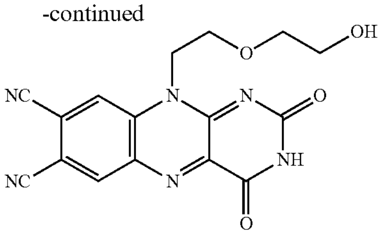

7

In a 10 ml round bottom flask, to 4-amino-5-[2-(2-hydroxyethoxy)-ethyl]-phthalonitrile (7a) (50 mg, 0.203 mmol) dissolved in acetate (1 mL), alloxan monohydrate (33.15 mg, 0.207 mmol 1.02 equiv.) and boric acid (12.8 mg, 0.207 mmol 1.02 equiv.) were added in acetate (2 mL) as a suspending solution. The reaction mixture was stirred at a room temperature for 12 hours and the precipitated yellow solid was filtered. The filtered solid was washed with ethyl ether, chloroform and hexane to obtain a yellow solid; 62 mg (87%)

$^1$H NMR (400 MHz, DMSO): δ. 11.70 (s, 1H), 8.90 (s, 1H), 8.81 (s, 1H), 6.55 (s, 2H), 4.78 (s, 2H), 4.52 (t, 1H, J=5.0 Hz), 3.82 (t, 2H, J=5.0 Hz), 3.38 (s, 2H)

$^{13}$C NMR (100 MHz, DMSO): δ. 159.40, 155.75, 151.59, 143.23, 137.59, 136.78, 135.67, 125.14, 117.32, 115.92, 115.71, 110.05, 72.96, 67.15, 60.53, 45.33

Preparative Example 15: 2,4-dioxo-2,3,4,10-tetrahydrobenzo[g]pteridine-7,8-dicarbonitrile [Chemical formula 8]

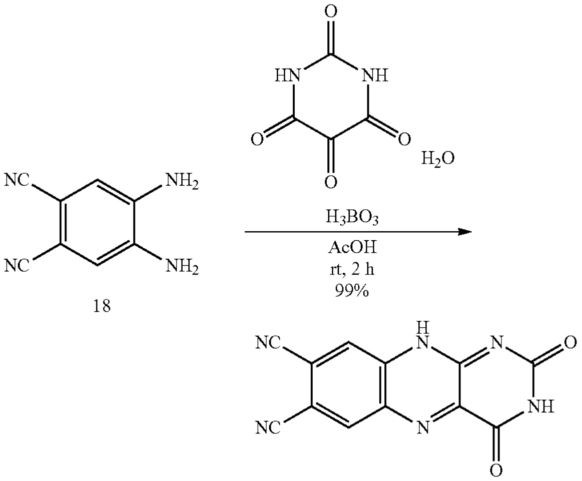

18

8

In a 10 ml round bottom flask, to 1,2-diamino-7,8-phthalonitrile (18) (100 mg, 0.632 mmol) dissolved in acetate (2 mL), alloxan monohydrate (121.5 mg, 0.759 mmol 1.2 equiv.) and boric acid (46.9 mg, 0.759 mmol 1.2 equiv.) were added in acetate (2 ml) as a suspending solution. The reaction mixture was stirred at a room temperature for 2 hours and the precipitated solid was filtered. The filtered solid was washed with ethyl ether, dichloromethane and hexane to obtain an ivory solid; 165 mg (99%)

$^1$H NMR (400 MHz, DMSO): δ. 12.42 (s, 1H), 11.97 (s, 1H), 9.05 (s, 1H), 8.73 (s, 1H) $^{13}$C NMR (100 MHz,

DMSO): δ. 159.70, 150.02, 149.43, 143.83, 139.24, 137.98, 136.10, 135.02, 115.76, 115.74, 115.65, 111.05.

Preparative Example 16: 4-amino-5-(4-methylbenzylamino]-phthalonitrile (9a)

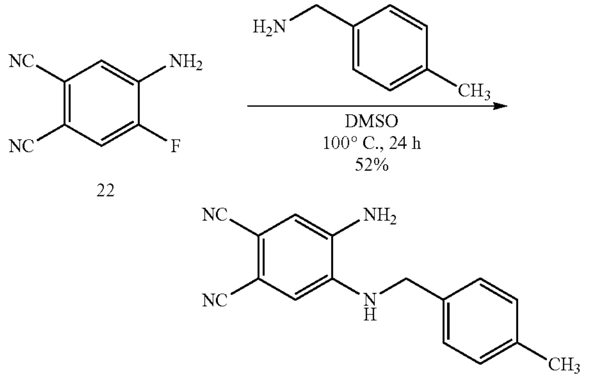

22

9a

In a 10 mL glass culture tube having a magnetic stirrer, 4-amino-5-fluorophthalonitrile (22) (100 mg, mmol) was dissolved in dimethylsulfoxide 0.5 ml, and then 4-methylbenzylamine (112.69 mg, 0.930 mmol, 1.5 equiv.) was added. The reaction mixture was stirred at 100° C. for 24 hours. The cooled reaction mixture was diluted using ethyl acetate at a room temperature and the organic layer was washed with water to remove dimethylsulfoxide. The collected organic layer was washed with saturated NaCl aqueous solution, and the remaining water was removed with anhydrous $Na_2SO_4$, and then the drying agent was filtered with a glass filter and the solvent was removed using a rotary evaporative condenser at maximum. To the solid mixture, dichloromethane was added to filter the precipitated solid, and dry it under reduced pressure, to obtain an ivory solid; 85 mg (52%)

$^1$H NMR (400 MHz, DMSO): δ 7.23 (d, J=7.7 Hz, 2H), 7.15 (d, J=7.6 Hz, 2H), 6.89 (s, 1H), 6.74 (s, 1N), 6.39 (d, J=5.7 Hz, 111), 6.06 (s, 2H), 4.38 (d, J=5.5 Hz, 2H), 2.28 (s, 4H).

$^{13}$C NMR (100 MHz, DMSO): δ 140.12, 138.54, 136.63, 135.70, 129.47, 127.71, 118.45, 118.19, 115.05, 112.29, 102.06, 101.91, 46.11, 21.11.

Preparative Example 17: 10-(4-methylbenzyl)-2,4-dioxo-2,3,4,10-tetrahydrobenzo[g]pteridine-7,8-dicarbonitrile [Chemical formula 9]

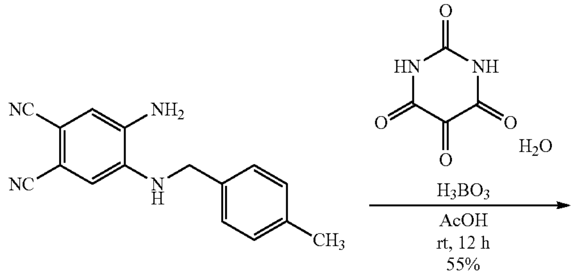

9a

-continued

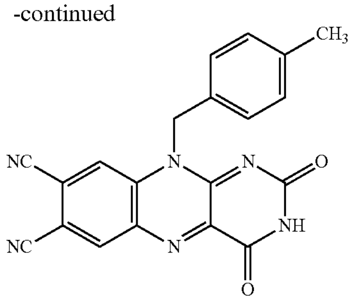

9

In a 10 ml round bottom flask, to 4-amino-5-(4-methylbenzylamino]-phthalonitrile (9a) (30 mg, 0.114 mmol) dissolved in acetate (2 mL), alloxan monohydrate (21.97 mg, 0.137 mmol 1.2 equiv.) and boric acid (8.47 mg, 0.137 mmol 1.2 equiv.) were added om acetate (2 ml) as a suspending solution. The reaction mixture was stirred at a room temperature for 12 hours and the precipitated yellow solid was filtered. The filtered solid was washed by ethyl ether, dichloromethane and hexane to obtain a yellow solid; 23 mg (55%)

$^1$H NMR (400 MHz, DMSO): δ 11.69 (s, 1H), 8.92 (s, 111), 8.39 (s, 1H), 7.22 (d, J=7.8 Hz, 2H), 7.10 (d, J=7.5 Hz, 2H), 5.77 (s, 2H), 2.23 (s, 4H).

$^{13}$C NMR (100 MHz, DMSO): δ 159.09, 155.51, 151.65, 143.52, 137.43, 137.02, 135.60, 135.39, 130.92, 129.24, 126.98, 123.06, 117.47, 115.42, 115.23, 110.31, 47.02, 20.72.

Preparative Example 18: 4-amino-5-(4-methoxybenzylamino)-phthalonitrile (10a)

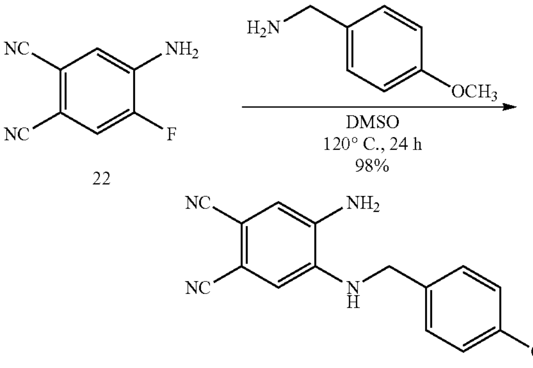

22

10a

In a 50 mL glass culture tube having a magnetic stirrer, 4-amino-5-fluorophthalonitrile (22) (1.6 g, 9.93 mmol) was dissolved in dimethylsulfoxide 8.0 mL, and then 4-methoxybenzylamine (1.632 g, 1.55 mL, 11.915 mmol, 1.2 equiv.) was added. The reaction mixture was stirred at 120 C for 24 hours. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $Na_2SO_4$, and then the drying agent was filtered with a glass filter and the solvent was removed using a rotary evaporative condenser at maximum. To the solid mixture, a small amount of dichloromethane was added and the precipitates were filtered and dried under reduced pressure, to obtain an ivory solid; 2.71 g (98%)

$^1$H NMR (400 MHz, DMSO): δ 7.28 (d, J=8.1 Hz, 2H), 6.95-6.90 (m, 2H), 6.89 (s, 1H), 6.78 (s, 1H), 6.37 (t, J=5.6 Hz, 1H), 6.07 (s, 2H), 4.35 (d, J=5.4 Hz, 2H), 3.73 (s, 3H).

13C NMR (100 MHz, DMSO): δ 158.85, 140.11, 138.53, 130.52, 129.12, 118.47, 118.21, 115.03, 114.30, 112.29, 102.03, 101.93, 55.47, 45.86.

Preparative Example 19: 10-(4-methoxybenzyl)-2,4-dioxo-2,3,4,10-tetrahydrobenzo[g]pteridine-7,8-dicarbonitrile [Chemical formula 10]

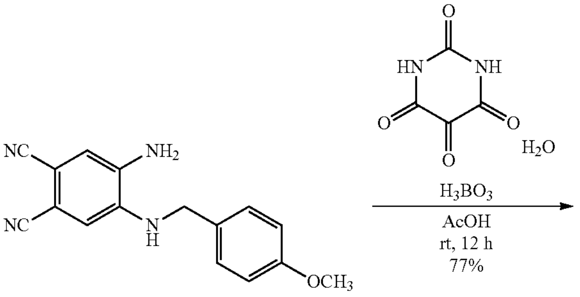

10a

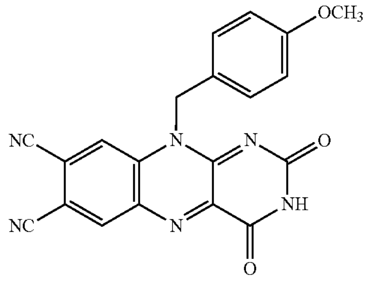

10

In a 10 ml round bottom flask, to 4-amino-5-(4-methoxybenzylamino)-phthalonitrile (10a) (30 mg, 0.108 mmol) dissolved in acetate (2 mL), alloxan monohydrate (20.7 mg, 0.129 mmol 1.2 equiv.) and boric acid (7.99 mg, 0.129 mmol, 1.2 equiv.) were added in acetate (2 ml) as a suspending solution. The reaction mixture was stirred at a room temperature for 12 hours and the precipitated orange solid was filtered. The filtered solid was washed with dichloromethane and n-hexane to obtain an orange yellow; 32 mg (77%)

$^1$H NMR (400 MHz, DMSO): δ 11.74 (s, 1H), 8.95 (s, 1H), 8.47 (s, 1H), 7.33 (d, 2H), 6.89 (d, 2H), 5.85 (br, 2H), 3.72 (s, 3H).

$^{13}$C NMR (100 MHz, DMSO): δ 172.50, 159.46, 159.19, 155.89, 152.02, 143.88, 137.81, 135.98, 135.74, 128.97, 126.16, 123.43, 117.83, 115.81, 115.61, 114.43, 110.66, 55.51, 47.07, 21.49.

Preparative Example 20: 4-amino-5-(3,4-dimethoxybenzylamino)-phthalonitrile (11a)

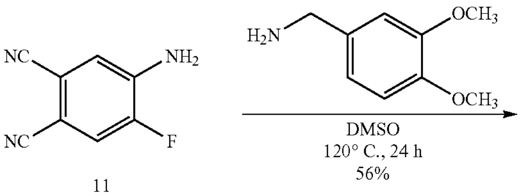

11

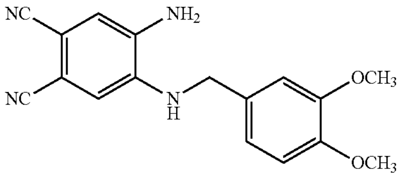

11a

In a 10 mL glass culture tube having a magnetic stirrer, 4-amino-5-fluorophthalonitrile(4) (200 mg, 1.24 mmol) was dissolved in dimethylsulfoxide 1.0 ml, and then 3,4-dimethoxybenzylamine (249 mg, 0.222 ml, 1.49 mmol, 1.2 equiv.) was added. The reaction mixture was stirred at 120° C. for 24 hours. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $Na_2SO_4$, and then the drying agent was filtered with a glass filter and the solvent was removed using a rotary evaporative condenser at maximum. To the solid mixture, dichloromethane was added to filter the precipitated solid and dry it under reduced pressure, to obtain an ivory solid; 213 mg (56%)

$^1$H NMR (400 MHz, DMSO): δ 6.99 (d, J=2.1 Hz, 1H), 6.92 (d, J=8.3 Hz, 1H), 6.89 (d, J=1.2 Hz, 1H), 6.86 (d, J=8.3 Hz, 1H), 6.80 (s, 1H), 6.35 (t, J=5.5 Hz, 1H), 6.08 (s, 2H), 4.34 (d, J=5.3 Hz, 2H), 3.74 (s, 3H), 3.73 (s, 3H).

$^{13}$C NMR (100 MHz, DMSO): δ 148.80, 148.02, 139.76, 138.25, 130.62, 119.52, 118.12, 117.86, 114.72, 112.02, 111.76, 111.53, 101.72, 101.60, 55.56, 55.50, 45.95.

Preparative Example 21: 10-(3,4-dimethoxybenzyl)-2,4-dioxo-2,3,4,10-tetrahydrobenzo[g]pteridine-7,8-dicarbonitrile [Chemical formula 11]

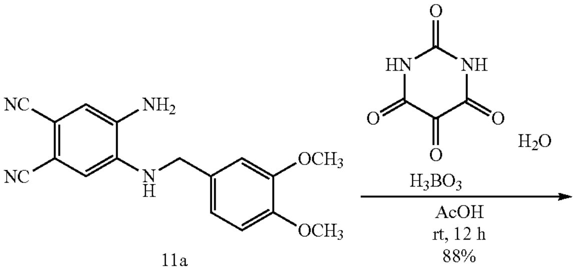

11a

-continued

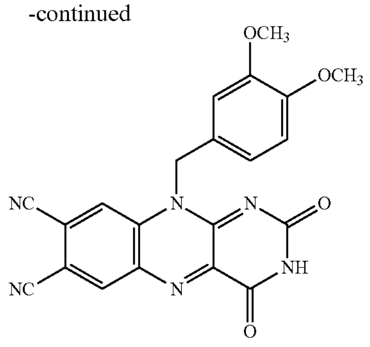

11

In a 10 ml round bottom flask, to 4-amino-5-(3,4-dimethoxybenzylamino)-phthalonitrile (11a) (100 mg, 0.324 mmol) dissolved in acetate (2 mL), alloxan monohydrate (57.1 mg, 0.357 mmol 1.1 equiv.) and boric acid (22.1 mg, 0.357 mmol 1.1 equiv.) were added in acetate (2 ml) as a suspending solution. The reaction mixture was stirred at a room temperature for 12 hours and the precipitated mustard solid was filtered. The filtered solid was washed with dichloromethane and hexane to obtain a mustard solid; 118 mg (88%)

$^{1}H$ NMR (400 MHz, DMSO) δ 11.75 (s, 1H), 8.94 (s, 1H), 8.48 (s, 1H), 7.09 (s, 1H), 6.84 (s, 1H), 5.92-5.56 (m, 2H), 3.72 (s, 3H), 3.70 (s, 3H).

$^{13}C$ NMR (100 MHz, DMSO) δ 159.15, 155.53, 151.65, 148.85, 148.47, 143.54, 137.46, 135.63, 135.49, 126.18, 123.14, 119.28, 115.47, 115.27, 111.74, 111.53, 110.30, 55.70, 55.54, 47.06

Preparative Example 22: 4-amino-5-(2,4-dimethoxybenzylamino)-phthalonitrile (12a)

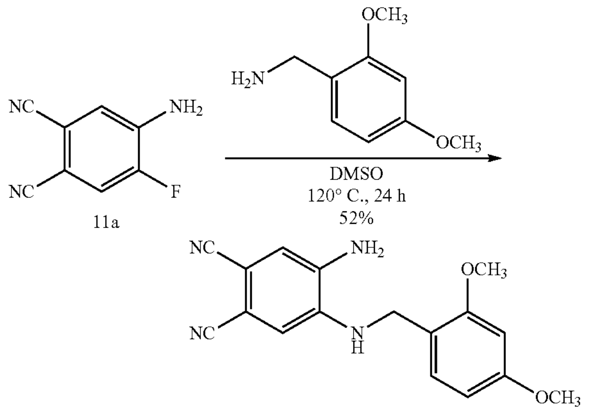

12a

In a 10 mL glass culture tube having a magnetic stirrer, 4-amino-5-fluorophthalonitrile (22) (200 mg, 1.24 mmol) was dissolved in dimethylsulfoxide 1.0 ml, and then 2,4-dimethoxybenzylamine (249 mg, 0.222 ml, 1.49 mmol, 1.2 equiv.) was added. The reaction mixture was stirred at 120° C. for 24 hours. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $Na_2SO_4$, and then the drying agent was filtered with a glass filter and the solvent was removed using a rotary evaporative condenser at maximum. To the solid mixture, dichloromethane was added to filter the precipitated solid and dry it under reduced pressure, to obtain an ivory solid; 198 mg (52%)

$^{1}H$ NMR (400 MHz, DMSO): δ 7.07 (d, J=8.3 Hz, 1H), 6.84 (d, J=0.9 Hz, 1H), 6.70 (s, 1H), 6.56 (d, J=2.4 Hz, 1H), 6.46 (dd, J=8.3, 2.4 Hz, 1H), 6.12 (t, J=5.4 Hz, 1H), 6.04 (s, 2H), 4.22 (d, J=5.3 Hz, 2H), 3.79 (s, 3H), 3.71 (s, 3H).

$^{13}C$ NMR (100 MHz, DMSO) δ 160.46, 158.54, 139.99, 138.70, 129.82, 118.50, 118.27, 117.94, 114.91, 111.99, 105.01, 101.98, 101.85, 98.84, 55.88, 55.63, 41.40.

Preparative Example 23: 10-(2,4-dimethoxybenzyl)-2,4-dioxo-2,3,4,10-tetrahydrobenzo[g]pteridine-7,8-dicarbonitrile [Chemical formula 12]

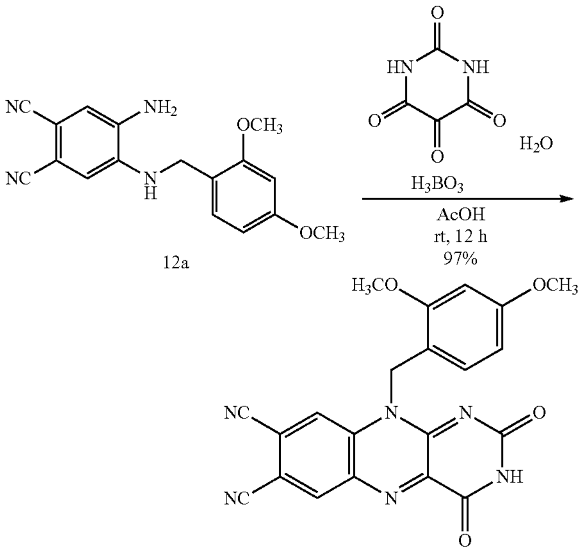

12

In a 10 ml round bottom flask, to 4-amino-5-(2,4-dimethoxybenzylamino)-phthalonitrile (12a) (50 mg, 0.162 mmol) dissolved in acetate (1 mL), alloxan monohydrate (28.6 mg, 0.178 mmol 1.1 equiv.) and boric acid (11.0 mg, 0.178 mmol 1.1 equiv.) were added in acetate (1 ml) as a suspending solution. The reaction mixture was stirred at a room temperature for 12 hours and the precipitated orange solid was filtered. The filtered solid was washed with dichloromethane and hexane to obtain an orange solid; 68 mg (97%)

$^{1}H$ NMR (400 MHz, DMSO): δ 11.67 (s, 1H), 8.92 (s, 1H), 8.34 (s, 1H), 6.75 (d, J=8.8 Hz, 1H), 6.63 (d, J=2.0 Hz, 1H), 6.30 (dd, J=8.8, 2.0 Hz, 1H), 5.56 (s, 2H), 3.87 (s, 3H), 3.68 (s, 3H)

$^{13}C$ NMR (100 MHz, DMSO) δ 160.34, 159.00, 157.54, 155.39, 151.54, 143.32, 137.38, 135.64, 135.51, 127.94, 123.44, 117.35, 115.41, 115.22, 113.37, 110.09, 104.78, 98.46, 55.70, 55.31.

Preparative Example 24: 4-amino-5-[2-(4-hydroxyphenyl)ethylamino]-phthalonitrile (13a)

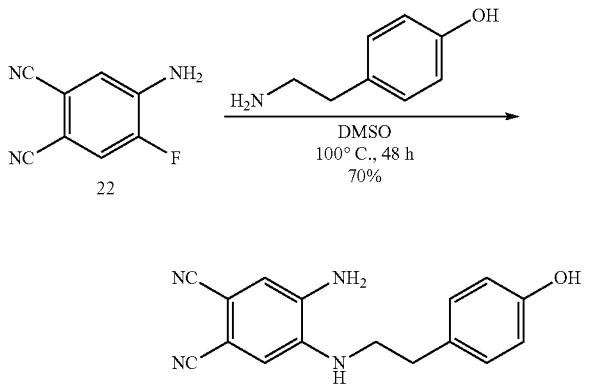

22

13a

In a 10 mL glass culture tube having a magnetic stirrer, 4-amino-5-fluorophthalonitrile (22) (100 mg, 0.620 mmol) was dissolved in dimethylsulfoxide 1.0 ml, and then 4-(2-aminoethyl)phenol (102 mg, 0.744 mmol, 1.2 equiv.) was added. The reaction mixture was stirred at 100° C. for 48 hours. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $Na_2SO_4$, and then the drying agent was filtered with a glass filter and the solvent was removed using a rotary evaporative condenser at maximum. To the solid mixture, dichloromethane was added to filter the undissolved solid and dry it under reduced pressure, to obtain a solid; 121 mg (70%)

$^1$H NMR (400 MHz, DMSO): δ 9.19 (s, 1H), 7.04 (d, J=8.5 Hz, 2H), 6.84 (d, J=2.6 Hz, 2H), 6.65 (d, J=8.5 Hz, 2H), 5.96 (s, 2H), 5.80 (t, J=5.6 Hz, 1H), 3.29 (t, J=7.6 Hz, 2H) 2.74 (t, J=7.6 Hz, 2H).

$^{13}$C NMR (100 MHz, DMSO): δ 156.15, 139.79, 138.75, 130.06, 129.73, 118.49, 118.35, 115.48, 114.85, 111.88, 102.31, 101.72, 45.01, 33.80.

Preparative Example 25: 10-[2-(4-hydroxyphenyl)ethyl]-2,4-dioxo-2,3,4,10-tetrahydrobenzo[g]pteridine-7,8-dicarbonitrile [Chemical formula 13]

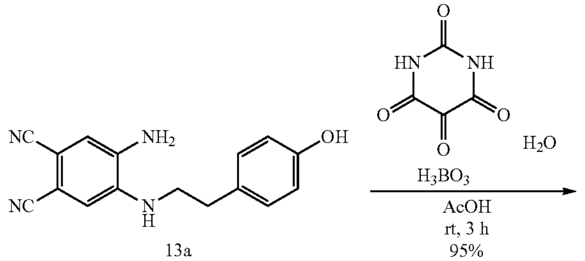

13a

-continued

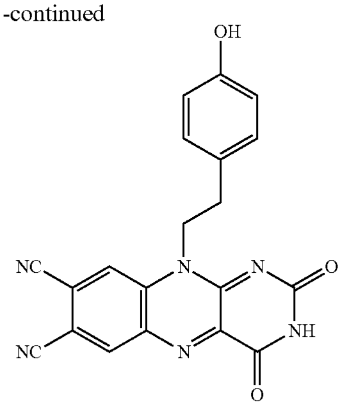

13

In a 10 ml round bottom flask, to 4-amino-5-[2-(4-hydroxyphenyl)ethylamino]-phthalonitrile (13a) (100 mg, 0.359 mmol) dissolved in acetate (2 mL), alloxan monohydrate (63.3 mg, 0.395 mmol 1.1 equiv.) and boric acid (24.4 mg, 0.395 mmol 1.1 equiv.) were added in acetate (2 ml) as a suspending solution. The reaction mixture was stirred at a room temperature for 3 hours and the precipitated orange solid was filtered. The filtered solid was washed with dichloromethane and hexane to obtain an orange solid; 131 mg (95%)

$^1$H NMR (400 MHz, DMSO): δ 11.72 (s, 1H), 9.30 (s, 1H), 8.89 (s, 1H), 8.46 (s, 1H), 7.10 (d, J=8.2 Hz, 1H), 6.63 (d, J=8.2 Hz, 1H), 4.72 (t, J=7.3 Hz, 2H), 2.90 (t, J=7.4 Hz, 2H).

$^{13}$C NMR (100 MHz, DMSO) δ 159.47, 156.69, 155.87, 151.24, 143.25, 137.66, 135.94, 135.48, 130.67, 127.78, 123.94, 117.30, 115.63, 115.45, 109.75, 46.31, 31.36.

Preparative Example 26: 4-amino-5-[2-(3,4-dihydroxyphenyl)ethylamino]-phthalonitrile (14a)

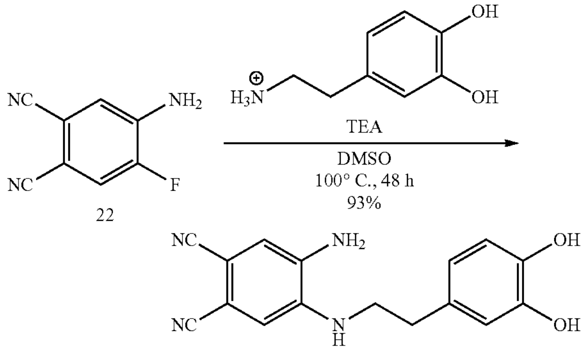

22

14a

In a 10 mL glass culture tube having a magnetic stirrer, 4-amino-5-fluorophthalonitrile (22) (200 mg, 1.24 mmol) was dissolved in dimethylsulfoxide 2.0 ml, and then dopamine hydrochloride (470.3 mg, 2.48 mmol, 2.0 equiv.) was added. Triethylamine (376.4 mg, 0.519 mL, 3.72 mmol, 3.0 equiv.) was slowly added dropwise at a room temperature. The reaction mixture was stirred at 100° C. for 48 hours. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $Na_2SO^-_4$, and then the drying agent was filtered with a glass filter and the solvent was removed using a rotary evaporative condenser at maximum. To the solid mixture, using methanol and diethylether, the solid precipitated by recrystallization was filtered and dried under reduced pressure, to obtain a brick red solid; 340 mg (93%)

$^1H$ NMR (400 MHz, DMSO): δ 8.74 (br, 2H), 6.87 (s, 2H), 6.76-6.60 (m, 2H), 6.52 (d, J=7.9 Hz, 1H), 5.99 (s, 2H), 5.82 (t, J=4.8 Hz, 1H), 2.71 (t, J=7.5 Hz, 2H).

$^{13}C$ NMR (100 MHz, DMSO): δ 145.47, 144.01, 140.11, 138.87, 130.51, 119.72, 118.59, 118.44, 116.67, 116.00, 114.63, 111.50, 101.97, 101.48, 45.10, 34.01.

Preparative Example 27: 10-[2-(4-hydroxyphenyl) ethyl]-2,4-dioxo-2,3,4,10-tetrahydrobenzo[g]pteridine-7,8-dicarbonitrile [Chemical formula 14]

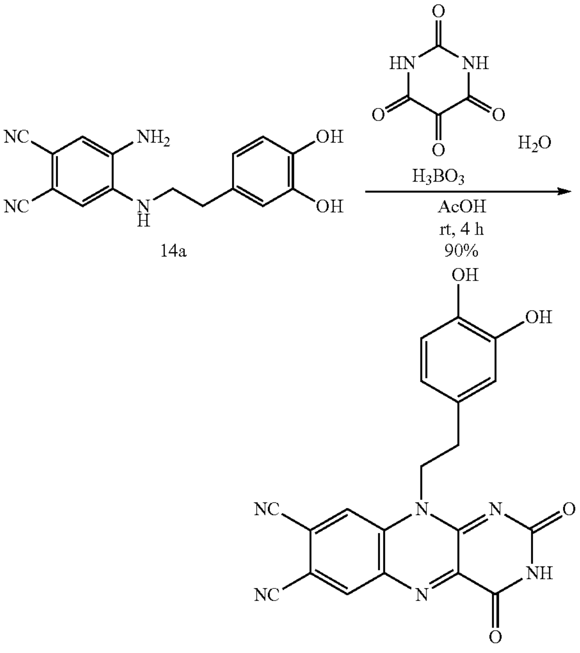

14a

14

To a 10 ml round bottom flask, to 4-amino-5-[2-(3,4-dihydroxyphenyl)ethylamino]-phthalonitrile (14a) (400 mg, 1.359 mmol) dissolved in acetate (10.0 mL), alloxan monohydrate (261.2 mg, 1.631 mmol 1.2 equiv.) and boric acid (100.8 mg, 1.631 mmol 1.2 equiv.) were added in acetate (10 ml) as a suspending solution. The reaction mixture was stirred at a room temperature for 4 hours and the precipitated solid was filtered. The filtered solid was washed with ethylether, chloroform and hexane to obtain a black brown solid; 492 mg (90%)

$^1H$ NMR (400 MHz, DMSO): δ. 11.69 (s, 1H), 8.86 (s, 1H), 8.81 (s, 1H), 8.73 (s, 1H), 8.47 (s, 1H), 6.66 (s, 1H), 6.57 (q, J=8.3 Hz, 2H), 4.66 (t, J=7.6 Hz, 2H), 2.79 (t, J=7.4 Hz, 2H).

$^{13}C$ NMR (100 MHz, DMSO): δ 159.47, 155.88, 151.26, 145.62, 144.55, 143.21, 137.69, 135.90, 135.56, 128.49, 123.93, 120.35, 117.39, 116.95, 115.77, 115.66, 109.86, 46.30, 31.57.

Preparative Example 28: 4-allylamino-5-amino-phthalonitrile (15a)

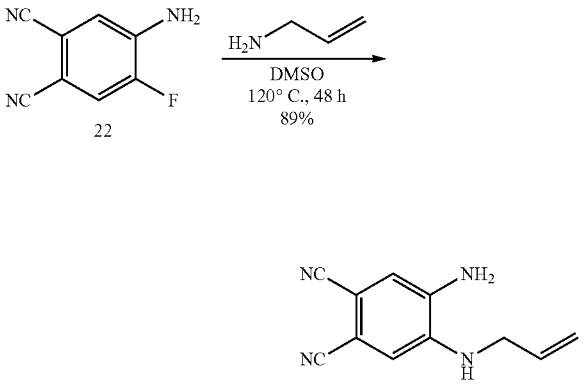

22

15a

In a 10 mL glass culture tube having a magnetic stirrer, 4-amino-5-fluorophthalonitrile (22) (200 mg, 1.24 mmol) was dissolved in dimethylsulfoxide 1.0 ml, and then allylamine (84.96 mg, 0.112 mL, 1.49 mmol, 1.2 equiv.) was added. The reaction mixture was stirred at 120° C. for 48 hours. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $Na_2SO_4$, and then the drying agent was filtered with a glass filter and the solvent was removed using a rotary evaporative condenser at maximum. To the solid mixture, a small amount of dichloromethane was added to filter the precipitated solid and dry it under reduced pressure, to obtain an ivory solid; 221 mg (89%)

$^1H$ NMR (400 MHz, DMSO): δ 6.89 (s, 1H), 6.77 (s, 1H), 6.08 (t, J=5.6 Hz, 1H), 6.02 (s, 2H), 5.88 (ddt, J=17.2, 10.2, 5.1 Hz, 1H), 5.20 (dq, J=17.4, 1.9 Hz, 1H), 5.15 (dt, J=10.3, 1.7 Hz, 1H), 3.86 (td, J=5.3, 2.6 Hz, 2H).

$^{13}C$ NMR (100 MHz, DMSO): δ 139.98, 138.58, 134.98, 118.51, 118.27, 116.58, 115.03, 112.32, 102.04, 101.96, 45.21.

Preparative Example 29: 10-allyl-2,4-dioxo-2,3,4,10-tetrahydrobenzo[g]pteridine-7,8-dicarbonitrile [Chemical formula 15]

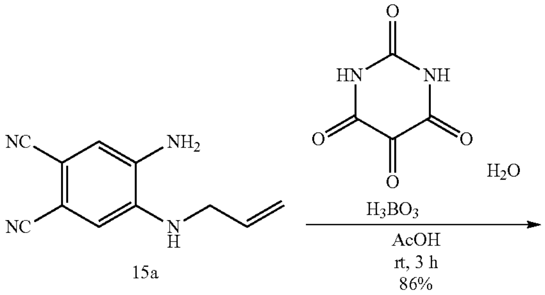

15a

-continued

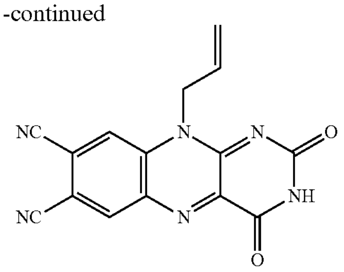

15

In a 25 ml round bottom flask, to 4-allylamino-5-aminophthalonitrile (15a) (200 mg, 1.01 mmol) dissolved in acetate (4 mL), alloxan monohydrate (177.7 mg, 1.11 mmol 1.10 equiv.) and boric acid (69.9 mg, 1.13 mmol 1.12 equiv.) were added in acetate (4 ml) as a suspending solution. The reaction mixture was stirred at a room temperature for 3 hours and the precipitated yellow solid was filtered. The filtered solid was washed with ethylether and hexane to obtain a yellow solid; 261 mg (86%)

$^1$H NMR (400 MHz, DMSO): δ 11.72 (s, 1H), 8.95 (s, 1H), 8.55 (s, 1H), 5.96 (ddd, J=17.3, 10.2, 4.9 Hz, 111), 5.22 (d, J=11.1 Hz, 1H), 5.18 (d, J=17.3 Hz, 1H).

$^{13}$C NMR (100 MHz, DMSO): δ 159.04, 155.47, 151.16, 143.17, 137.46, 135.55, 135.38, 129.83, 123.45, 118.02, 117.51, 115.49, 110.12, 46.46.

Preparative Example 30: 4-amino-5-(2-hydroxyethyl)phthalonitrile (16a)

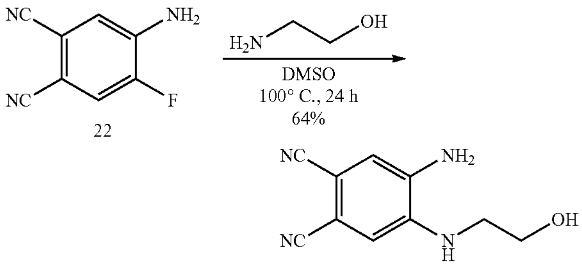

22

16a

In a 10 mL glass culture tube having a magnetic stirrer, 4-amino-5-fluorophthalonitrile (22) (200 mg, 1.24 mmol) was dissolved in dimethylsulfoxide 1.0 ml, and then ethanolamine (90.4 mg, 0.089 mL, 1.48 mmol, 1.2 equiv.) was added. The reaction mixture was stirred at 100° C. for 24 hours. The cooled reaction mixture was diluted using ethyl acetate at a room temperature, and the organic layer was washed with water to remove dimethylsulfoxide. The collected organic layer was washed with saturated NaCl aqueous solution, and the remaining water was removed with anhydrous $Na_2SO_4$, and then the drying agent was filtered with a glass filter and the solvent was removed using a rotary evaporative condenser at maximum. To the solid mixture, dichloromethane was added to filter the precipitated solid and dry it under reduced pressure, to obtain an ivory solid; 161 mg (64%)

$^1$H NMR (400 MHz, DMSO): δ 6.87 (s, 2H), 6.00 (s, 2H), 5.81 (t, J=5.4 Hz, 1H), 4.80 (t, J=5.5 Hz, 111), 3.58 (q, J=5.6 Hz, 2H), 3.24 (q, J=5.6 Hz, 2H).

$^{13}$C NMR (100 MHz, DMSO) δ 160.46, 158.54, 139.99, 138.70, 129.82, 118.50, 118.27, 117.94, 114.91, 111.99, 105.01, 101.98, 101.85, 98.84, 55.88, 55.63, 41.40.

Preparative Example 31: 10-(2-hydroxyethyl)-2,4-dioxo-2,3,4,10-tetrahydrobenzo[g]pteridine-7,8-dicarbonitrile [Chemical formula 16]

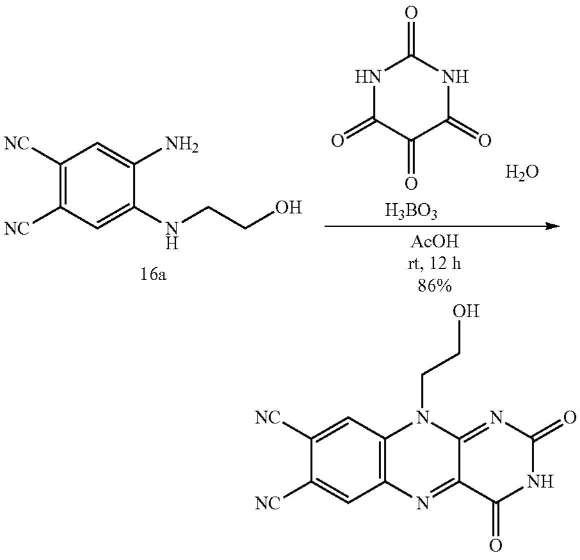

16a

16

In a 10 ml round bottom flask, to 4-amino-5-(2-hydroxyethyl)phthalonitrile (16a) (400 mg, 1.978 mmol) dissolved in acetate (5 mL), alloxan monohydrate (380.24 mg, 2.373 mmol 1.2 equiv.) and boric acid (146.8 mg, 2.373 mmol 1.2 equiv.) were added in acetate (10 ml) as a suspending solution. The reaction mixture was stirred at a room temperature for 12 hours and the precipitated yellow solid was filtered. The filtered solid was washed with ethylether, chloroform and hexane to obtain a yellow solid; 528 mg (86%)

$^1$H NMR (400 MHz, DMSO): δ 11.71 (s, 1H), 8.92 (s, 1H), 8.82 (s, 1H), 4.94 (t, J=5.9 Hz, 1H), 4.69 (t, J=5.6 Hz, 2H), 3.81 (q, J=5.7 Hz, 2H).

$^{13}$C NMR (100 MHz, DMSO): δ 159.37, 155.74, 151.62, 143.12, 137.70, 137.02, 135.73, 125.01, 117.36, 115.93, 115.67, 109.98, 57.91, 47.43.

Preparative Example 32: 10-(2-chloroethyl)-2,4-dioxo-2,3,4,10-tetrahydrobenzo[g]pteridine-7,8-dicarbonitrile [Chemical formula 17]

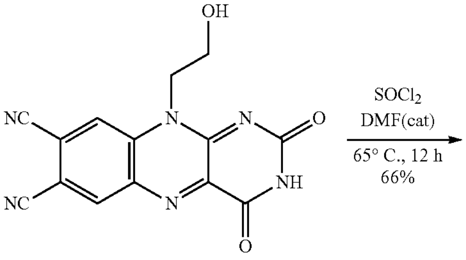

16

-continued

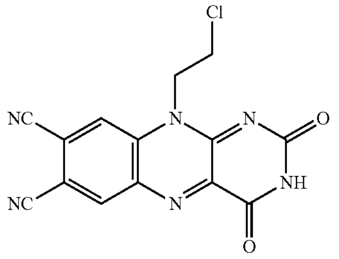

17

In a 10 ml round bottom flask, 10-(2-hydroxyethyl)-2,4-dioxo-2,3,4,10-tetrahydrobenzo[g]pteridine-7,8-dicarbonitrile (16) (300 mg, 0.973 mmol) was added in a solid state, and under the nitrogen atmosphere, $SOCl_2$ (5.0 mL) was added as a reactant and a solvent. After adding DMF (20 μl) at a room temperature, a reflux condenser was installed, and the reaction mixture was stirred at 65° C. for 12 hours. The cooled reaction mixture was poured in a beaker having ice at a room temperature to complete the reaction. The ice water layer was extracted using ethyl acetate three times and the collected organic layer was washed with saturated NaCl aqueous solution. The remaining water was removed with anhydrous $Na_2SO_4$, and then the drying agent was filtered with a glass filter and the solvent was removed using a rotary evaporative condenser at maximum. To the solid mixture, dichloromethane was added to filter the precipitated solid and dry it under reduced pressure, and DMF and impurities were removed to obtain a mustard solid; 210 mg (66%)

$^1H$ NMR (400 MHz, DMSO): δ 12.40 (s, 1H), 9.09 (s, 1H), 8.84 (s, 1H), 4.50 (t, J=7.1 Hz, 2H), 3.82 (d, J=14.2 Hz, 2H).

$^{13}C$ NMR (100 MHz, DMSO): δ 158.66, 149.75, 148.60, 142.87, 138.76, 137.78, 136.16, 135.42, 116.05, 115.64z, 115.48, 111.77, 42.48.

Preparative Example 33: Polyvinylimidazole having 10-ethyl-2,4-dioxo-2,3,4,10-tetrahydrobenzo[g]pteridine-7,8-dicarbonitrile [Chemical formula 25]

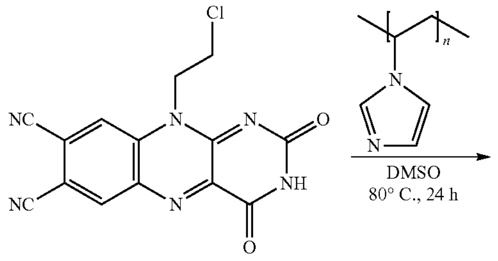

17

-continued

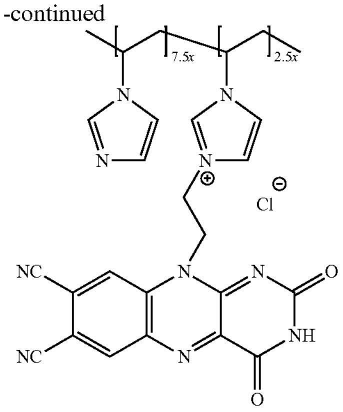

25

In a 10 mL glass culture tube having a magnetic stirrer, 10-(2-chloroethyl)-2,4-dioxo-2,3,4,10-tetrahydrobenzo[g]pteridine-7,8-dicarbonitrile (17) (20 mg, 0.0612 mmol) and polyvinylimidazole (24 mg, 0.245 mmol) were added in a solid state, and they were dissolved at a room temperature under the nitrogen atmosphere by adding dimethylsulfoxide 1.0 mL. The reaction mixture was stirred at 80° C. for 24 hours. After confirming whether the reaction was completed by nuclear magnetic resonance analysis, the reaction mixture was cooled at a room temperature. The reaction mixture sufficiently cooled was slowly added dropwise in ethyl acetate coldly cooled to 0° C. and the solvent and the remaining starting material were removed. The produced precipitates were washed with dichloromethane again, and then were dried under reduced pressure to obtain a light brown solid polymer.; weight recovery rate 32 mg

[Result and Consideration]

Example 1: Synthesis

The organic-based electron-transfer mediator according to the present invention was synthesized according to Reaction formula 4 or Reaction formula 5 below.

[Reaction Formula 4]

Synthesis Method of Flavin Derivative (2)

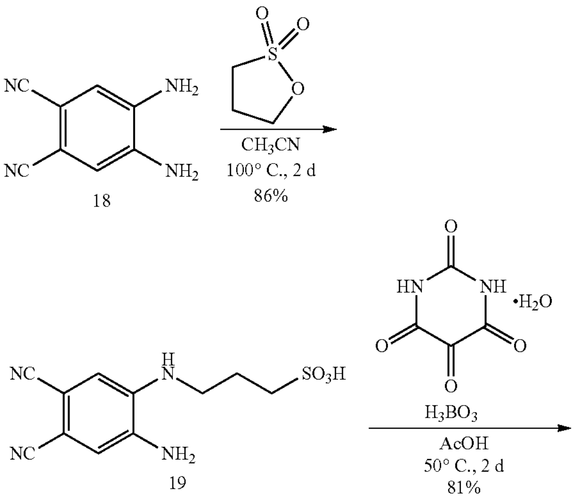

-continued

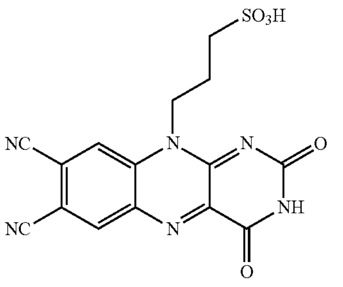

2

Commercially purchased 4,5-diaminophthalonitrile (18) and 1,3-propanesulfone were reacted at 100° C. for 2 days to obtain 3-[(2-amino-4,5-dicyano)phenylamino]propane-1-sulfonic acid (19) as a brown solid. After that, alloxan monohydrate and boric acid were heated using acetate as a solvent at 50° C. for 2 days to obtain a yellow solid, 3-(7,8-dicyanoisoalloxazinyl)-1-propanesulfonic acid (2) in 81% yield. Many by-products were produced in this reaction, and when materials undissolved in an acetonitrile solvent were separated, the product could be obtained relatively cleanly.

In addition, by using 1,2-dibromo-4,5-difluorobenzene (20) instead of 4,5-diaminophthalonitrile (18), which is an expensive starting material, a new method for synthesizing a flavin derivative having high added value and having various terminal groups in the structure of the connecting part was found. [Reaction formula 5]represents a new method for synthesizing a derivative capable of introduction for a water-soluble polymer chain through a change in the amine structure using a nucleophile aromatic substitution reaction between 4-amino-5-fluorophthalonitrile (22) and chain amine.

[Reaction Formula 5]

Diamine structure using nucleophile aromatic substitution reaction and flavin derivative synthesis method

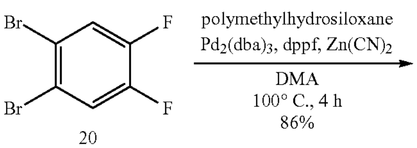

20

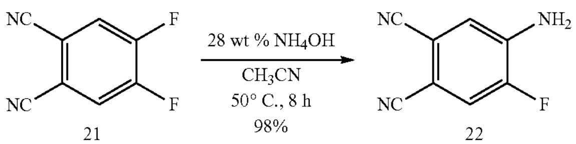

21 22

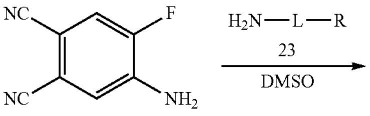

22

-continued

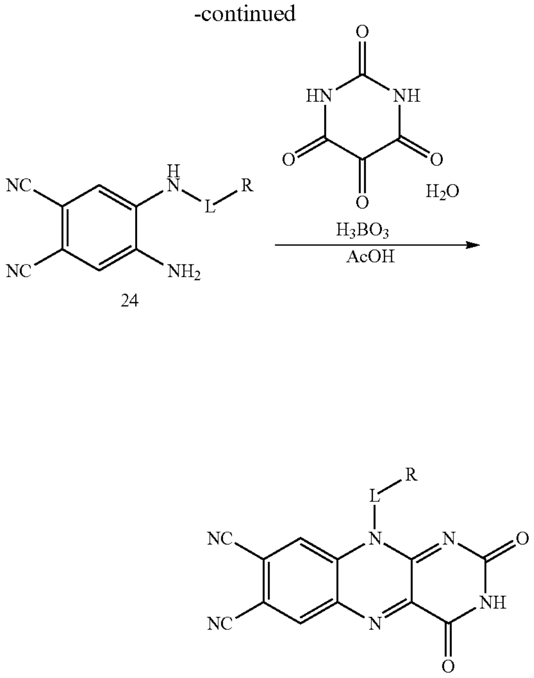

24

1

Example 2: Confirmation of Electrochemical Properties of the Organic-Based Electron-Transfer Mediator According to the Present Invention Using Cyclic Voltammetry Method The synthesis yield and oxidation reduction potential ($E_{1/2}$) value of various flavin or isoalloxazine derivatives synthesized using the synthesis method as above were confirmed. The measurement of the oxidation reduction potential was performed by the method as below.

Experimental Method

The organic-based electron-transfer mediator of 15 mg was dissolved in 0.1 M phosphate-buffered saline (PBS) or 0.1 M tetrabutylammonium perchlorate acetonitrile solution, or 0.1 M tetrabutyl ammonium perchlorate dimethylsulfoxide 5 mL according to each solubility. A working electrode, a reference electrode and a counter electrode were connected, and an electrical signal change according to the change in voltage was measured.

Experimental Materials/Condition

Working electrode: Free carbon electrode (dia: 3.0 mm)

Reference electrode: Ag/AgCl electrode Counter electrode: Platinum rod

Test Parameters

Equipment: EmStat (PalmSens Co.), CHI1040C (CH Instruments Co.)

Technique: cyclic voltammetry

Potential range: −1.0~1.0 V

Scan rate: 10 mV/s

The oxidation reduction potential and synthesis yield measured according to the method were shown in the following Tables 1 and 2.

TABLE 1

Synthesis yield and oxidation reduction potential (E½) of synthesized flavin or isoalloxazine derivatives

| Isoalloxazine derivative | state and yield | $E_{1/2}$ (vs Ag/AgCl) | Conditions |
|---|---|---|---|
| 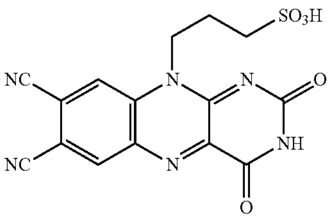 [SMILES: N#Cc1cc2nc3c(=O)[nH]c(=O)nc-3n(CCCS(=O)(=O)O)c2cc1C#N] | yellow solid 81% | −0.172 V<br>−0.315 V<br>0.061 V | 0.1M PBS in $H_2O$<br>0.1M TBAP in $CH_3CN$<br>0.1M TBAP in DMSO |
| 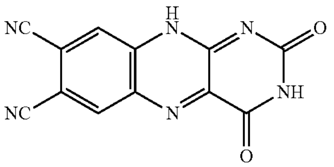 [SMILES: N#Cc1cc2nc3c(=O)[nH]c(=O)nc-3[nH]c2cc1C#N] | ivory solid 73% | −0.494 V | 0.1M TBAP in DMSO |
| 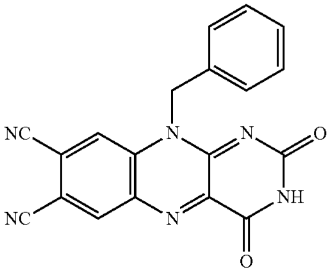 [SMILES: N#Cc1cc2nc3c(=O)[nH]c(=O)nc-3n(Cc3ccccc3)c2cc1C#N] | yellow solid 87% | −0.285 V | 0.1M TBAP in DMSO |
| 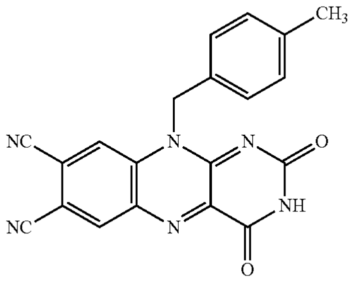 [SMILES: Cc1ccc(Cn2c3nc(=O)[nH]c(=O)c-3nc3cc(C#N)c(C#N)cc32)cc1] | yellow solid 55% | −0.296 V | 0.1M TBAP in DMSO |
| 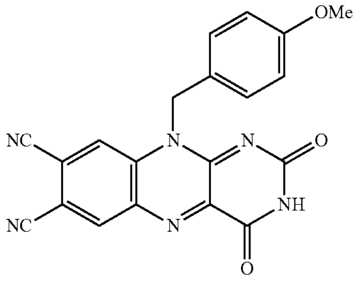 [SMILES: COc1ccc(Cn2c3nc(=O)[nH]c(=O)c-3nc3cc(C#N)c(C#N)cc32)cc1] | orange solid 77% | −0.298 V | 0.1M TBAP in DMSO |

TABLE 2

Synthesis yield and oxidation reduction potential (E½) of synthesized flavin or isoalloxazine derivatives

| Isoalloxazine derivative | state and yield | $E_{1/2}$ (vs Ag/AgCl) | Conditions |
|---|---|---|---|
| 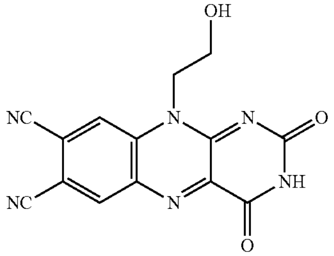 [SMILES: N#Cc1cc2nc3c(=O)[nH]c(=O)nc-3n(CCO)c2cc1C#N] | yellow solid 86% | −0.153 V<br>−0.319 V<br>−0.315 V | 0.1M PBS in $H_2O$<br>0.1M TBAP in $CH_3CN$<br>0.1M TBAP in DMSO |
| 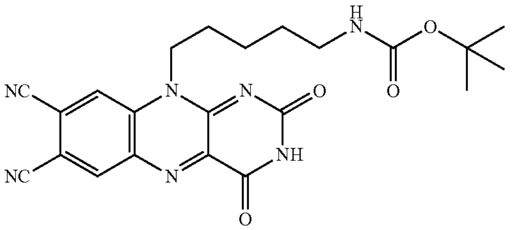 [SMILES: CC(C)(C)OC(=O)NCCCCCn1c2nc(=O)[nH]c(=O)c-2nc2cc(C#N)c(C#N)cc21] | yellow solid 59% | −0.330 V | 0.1M TBAP in $CH_3CN$ |
| 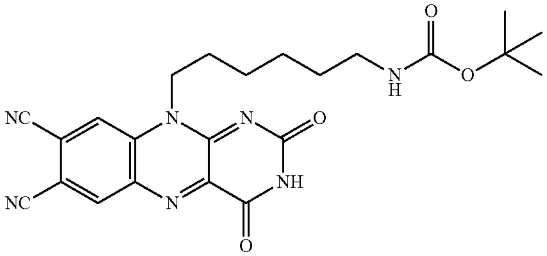 [SMILES: CC(C)(C)OC(=O)NCCCCCCn1c2nc(=O)[nH]c(=O)c-2nc2cc(C#N)c(C#N)cc21] | yellow solid 79% | −0.330 V | 0.1M TBAP in $CH_3CN$ |
| 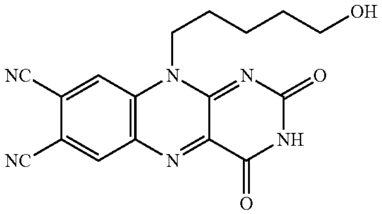 [SMILES: N#Cc1cc2nc3c(=O)[nH]c(=O)nc-3n(CCCCCO)c2cc1C#N] | yellow solid 86% | −0.325 V | 0.1M TBAP in DMSO |
| 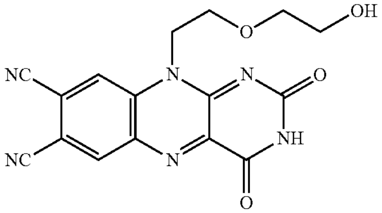 [SMILES: N#Cc1cc2nc3c(=O)[nH]c(=O)nc-3n(CCOCCO)c2cc1C#N] | yellow solid 87% | −0.315 V | 0.1M TBAP in DMSO |

([a] $E_{1/2}$ value was determined as the average of the oxidized peak and reduced peak in cyclic voltammograms (CV). CV was measured using Ag/AgCl as a reference electrode, a carbon glass electrode as a working electrode, and a Pt electrode as a counter electrode)

Among them, the electrochemical properties of the materials whose CV result met the target in an aqueous solution, 3-(7,8-dicyano-2,4-dioxo-3,4-dihydrobenzo[g]pteridin-10(2H)-yl)propane-1-sulfonate [Chemical formula 2] and 10-(2-hydroxyethyl)-2,4-dioxo-2,3,4,10-tetrahydrobenzo[g]pteridine-7,8-dicarbonitrile [Chemical formula 15], were investigated by cyclic voltammetry. The result measured by using glassy carbon (dia. 3 mm) as a working electrode, Ag/AgCl (vycor type) as a reference electrode, and Pt rod as a counter electrode was obtained. A solution at a concentration of 2 mg/mL was made using water as a solvent and was used for measurement, and pH was adjusted with 0.1M PBS buffer. The CV measurement result was as FIG. 2.

In case of [Chemical formula 2], at pH 7.0, $E_{ox}$ was −0.139 V, $E_{red}$ was −0.229 V, and Chemical formula 15 has $E_{ox}$ was −0.120 V, $E_{red}$ was −0.216 V, and showed a reversible graph and therefore an expected oxidation reduction potential spec was satisfied. When the CV was measured for each pH, it could be confirmed that the oxidation potential value changed more significantly compared to the reduction potential towards acidic condition (FIG. 3*a*, FIG. 3*b*). In addition, in order to investigate stability by pH, when the CV was measured after one day of the solution of each pH condition, it could be found that the current value decreased under the basic condition (FIG. 4*a*-4*f*). From this result, it could be seen that the compound was modified in a basic environment and therefore, it could not participate in the existing oxidation reduction reaction.

The tendency of the change in the oxidation reduction potential value for the solvent of 3-(7,8-dicyano-2,4-dioxo-3,4-dihydrobenzo[g]pteridin-10(2H)-yl)propane-1-sulfonate [Chemical formula 2] and 10-allyl-2,4-dioxo-2,3,4,10-tetrahydrobenzo[g]pteridine-7,8-dicarbonitrile [Chemical formula 15], 10-(2-hydroxyethyl)-2,4-dioxo-2,3,4,10-tetrahydrobenzo[g]pteridine-7,8-dicarbonitrile [Chemical formula 16] was to be compared. The cyclic voltammetry (CV) of 3 kinds of organic electron-transfer mediators measured in several buffer solutions. They are figures showing the cyclic voltammetry and oxidation reduction potential value and $E_{12}$ at that time measured in 0.1 M PBS in $H_2O$, 0.1M TBAP in $CH_3CN$, 0.1M TBAP in DMSO of 5a: Chemical formula 2, 5b: Chemical formula 14, 5c: Chemical formula 15. The structure with the largest change in the oxidation reduction potential value according to the measurement solvent among measured three materials is 3-(7,8-dicyano-2,4-dioxo-3,4-dihydrobenzo[g]pteridin-10(2H)-yl)propane-1-sulfonate [Chemical formula 2]. In the cyclic voltammetry measured in 0.1 M TBAP in DMSO solution, it could be seen that the half-wave potential ($E_{1/2}$) was 0.061 V and shifted a lot to the right. This is tendency different from other flavin-based organic electron-transfer mediators synthesized in the corresponding study. Unlike in water or acetonitrile buffer solution, the color of the solution gradually changes to dark red, so it is thought that it is changed to a different structure under DMSO. FIG. 5*b* is cyclic voltammetry of 10-allyl-2,4-dioxo-2,3,4,10-tetrahydrobenzo[g]pteridine-7,8-dicarbonitrile [Chemical formula 15] depending on the solvent. Since there was a difference in solubility depending one the solvent, the current strength was smaller as the solubility was lower, and the amount of current increased as the solubility in the corresponding solvent was better. It can be confirmed that the solubility in water is very low, and the current magnitude is small in 0.1 M PBS aqueous buffer. It could be confirmed that a remarkable feature here was that the half-wave potential ($E_{1/2}$) in water of the corresponding structure was −0.196 V compared to the Ag/AgCl reference electrode, and it had an oxidation reduction potential suitable for a target blood glucose meter. However, there is a limitation in its use that water solubility is very low. In addition, it was confirmed that there was almost no difference in oxidation reduction potential values in $CH_3CN$ and DMSO using the same electrolyte. When looking at the electrochemical properties of the 10-(2-hydroxyethyl)-2,4-dioxo-2,3,4,10-tetrahydrobenzo[g]pteridine-7,8-dicarbonitrile [Chemical formula 16] derivative, it can be seen that the corresponding material has very low solubility in acetonitrile on the contrary, and the current value in 0.1 M TBAP in $CH_3CN$ buffer solution is very small. On the other hand, it could be confirmed that the solubility in water was prominent and the half-wave potential ($E_{1/2}$) measured in 0.1 M PBS in $H_2O$ buffer solution was −0.154 V, which was included in the desired potential range, thereby confirming that it had electrochemical properties applicable for a blood glucose measurement sensor. Furthermore, it could be confirmed that the difference of the oxidation reduction potential values between acetonitrile and dimethylsulfoxide was very low with a similar tendency to the preceding [Chemical formula 15]. In addition, the difference of the oxidation reduction potential values between water and organic solvent is about 120-150 mV, following a similar trend. Therefore, through the result of CV analysis of [Chemical formula 15] and [Chemical formula 16], it can be inferred that the remaining isoalloxazine derivatives measuring only cyclic voltammetry in acetonitrile and dimethylsulfoxide because of low solubility in water may have electrochemical properties comprised in the desired oxidation reduction potential value range, if the solubility in water is ensured.

Example 3: Confirmation of Electrochemical Properties Using Cyclic Voltammetry in Case of Fixing the Organic-Based Electron-Transfer Mediator According to the Present Invention in Polymer Matrix In order to confirm the applicability of the organic-based electron-transfer mediator according to the present invention in a continuous blood glucose measurement system by fixing an electron carrier in a polymer matrix, an experiment was performed according to the following method.

As the introduction method using the reactivity of the electron carrier having a leaving group at the end and a nucleophile polymer, a halogenation reaction of an alcohol using dimethylformamide of 10-(2-hydroxyethyl)-2,4-dioxo-2,3,4,10-tetrahydrobenzo[g]pteridine-7,8-dicarbonitrile [Chemical formula 16] as a catalyst of the reaction was used. Accordingly, the electron carrier having a good leaving group, chloride at the end was extracted by using ethyl acetate and water, and then 10-(2-chloroethyl)-2,4-dioxo-2,3,4,10-tetrahydrobenzo[g]pteridine-7,8-dicarbonitrile [Chemical formula 17] could be synthesized in 85% yield through precipitation using dichloromethane. FIG. 6 summarizes synthesis of the organic-based electron-transfer mediator having a good leaving group and polymer introduction using it. Then, after dissolving the material of [Chemical formula 17] in polyvinylimidazole and dimethylsulfoxide and heating it to 80° C. for 24 hours, by precipitation in ethyl acetate and dichloromethane, the polymer [Chemical formula 25] could be obtained as a brown solid.

[Reaction formula 6]

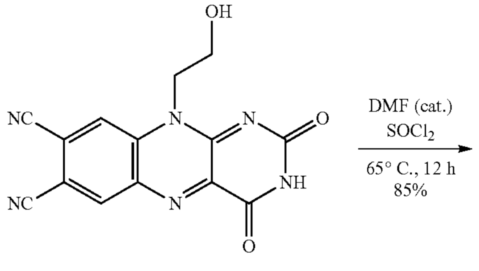

16

-continued

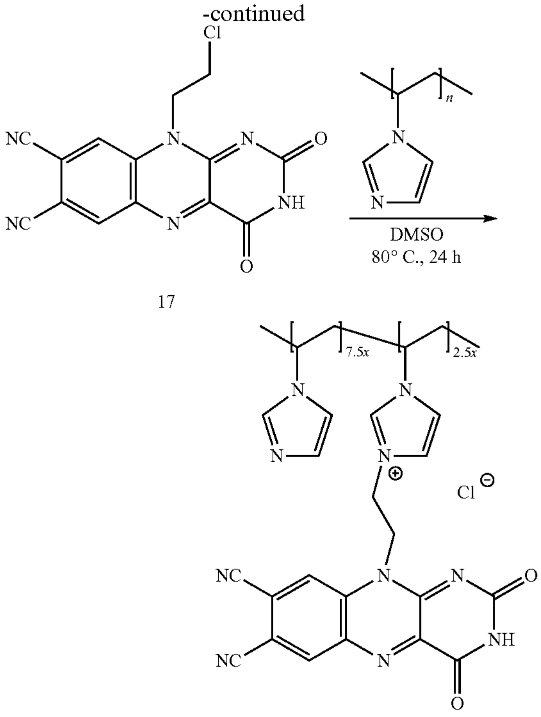

17

25

[Reaction formula 25]

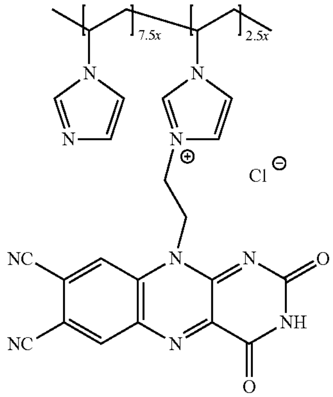

Since the compound of Chemical formula 25 has a relatively low solubility of the polymer in water, there is a limit to using a buffer solution due to the salting out effect, and therefore, the cyclic voltammetry was measured by using water as a solvent. The result was shown in FIG. 6. As could be confirmed in FIG. 6, after introduced into the polymer, the oxidation potential ($E_{ox}$) was −0.108 V, and the reduction potential ($E_{red}$) was −0.238 V, and the half-wave potential ($E_{1/2}$) was 0.173 V. Therefore, it could be expected that even after introduction of the polymer, the oxidation reduction potential value is included in the target oxidation reduction potential range, and introduction into a continuous blood glucose system could be possible.

The invention claimed is:

1. An organic electron-transfer mediator having the structure of Chemical formula 1 below:

[Chemical formula 1]

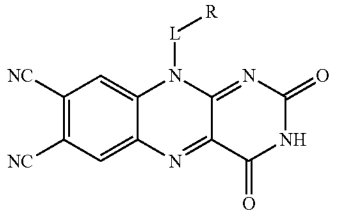

in the formula, R is —H, —F, —Cl, —Br, —I, —$NO_2$, —CN, —$CO_2H$, —$SO_3H$, —$NHNH_2$, —SH, —OH, —$NR_1R_2$, an unsubstituted or substituted alkyl group having 1 to 6 carbon atoms, an unsubstituted or substituted alkenyl group having 24 to 6 carbon atoms, or an unsubstituted or substituted aryl group having 6 to 10 carbon atoms, and the $R_1$ and $R_2$ may be each independently H, alkyl having 1 to 3 carbon atoms, or —$COOR_3$, and the $R_3$ may be alkyl having 1 to 6 carbon atoms, L (linker) may be one or more selected from the group consisting of a bond, a substituted or unsubstituted alkyl group having 1 to 20 carbon atoms, a substituted or unsubstituted alkenyl group having 2 to 20 carbon atoms, a substituted or unsubstituted ethylene oxide group having 2 to 50 carbon atoms, a substituted or unsubstituted ethylene amine group having 2 to 50 carbon atoms, a substituted or unsubstituted alkoxy group having 1 to 30 carbon atoms, a substituted or unsubstituted aryl or aryloxy group having 6 to 30 carbon atoms, or a substituted or unsubstituted heteroaryl group or heteroaryloxy group having 5 to 30 carbon atoms.

2. The organic electron-transfer mediator according to claim 1, wherein the unsubstituted alkyl group having 1-20 carbon atoms in the L is one or more kinds selected from the group consisting of a methyl group, an ethyl group, a propyl group, an isopropyl group, an n-butyl group, a sec-butyl group, a t-butyl group, a pentyl group, a hexyl group, a cyclohexyl group, a heptyl group, an octyl group and a decane group; and the substituted or unsubstituted ethylene oxide group having 2 to 50 carbon atoms is one or more kinds selected from the group consisting of ethylene oxide groups in which the number of n in $(—OCH_2CH_2—)_n$ is 1-20; and the substituted or unsubstituted ethylene amine group having 2 to 50 carbo atoms is one or more kinds selected from the group consisting of ethylene amine groups in which the number of n in $(—NHCH_2CH_2—)_n$ is 1-20; and the substituted or unsubstituted alkoxy group having 1 to 30 carbon atoms may be one selected from the group consisting of methoxy, ethoxy, propoxy, isopropoxy, butoxy, tert-butoxy, pentanoxy, hexanoxy, heptanoxy, octanoxy, decanoxy, alkyl-decanoxy, dodecanoxy, alkyl-dodecanoxy, undecanoxy, alkyl-undecanoxy, allyloxy, cycloalkyloxy and cyclohexyloxy; and the substituted or unsubstituted aryl or aryloxy having 6 to 30 carbo atoms is one selected from the group consisting of a phenyl group, a tolyl group, a naphthalene group, a phenanthrene group, an alkyl phenyl group and a phenyloxy group, a benzyloxy group, a tolyloxy group, a naphthalene oxy group, a phenanthrene oxy group, and an alkoxyphenyl group; and the substituted or unsubstituted heteroaryl group or heteroaryloxy group having 5 to 20 carbon atoms is one selected from the group consisting of furyl, thiophenyl, pyrrolyl, imidazolyl, pyrazolyl, thiazolyl, thiadiazolyl, isothiazolyl, isooxazolyl, oxazolyl, oxadiazolyl, triazinyl, tetrazinyl, trazolyl, tetrazolyl, furazanyl, pyridyl, pyrazinyl, pyrimidinyl, pyridazinyl, heteroaryl, benzofuranyl, benzothiophenyl, isobenzofuranyl, benzoimidazolyl, benzothiazolyl, benzoisothiazolyl, benzoixoazolyl, benzooxazolyl, isoindolyl, indolyl, indazolyl, benzothiadiazolyl, quinolyl, isoquinolyl, quinoxalinyl, carbazolyl, phenanthridinyl and benzodioxolyl.

3. The organic electron-transfer mediator according to claim 1, wherein the R is —H, —F, —Cl, —Br, —I, —$NO_2$, —CN, —$CO_2H$, —$SO_3H$, —$NHNH_2$, —SH, —OH, —$NR_1R_2$, an unsubstituted or substituted alkyl group having 1 to 3 carbon atoms, an unsubstituted or substituted alkenyl group having 2 to 3 carbon atoms, or a phenyl group, and the $R_1$ and $R_2$ is each independently H or Boc (t-butoxycarbonyl).

4. The organic electron-transfer mediator according to claim 1, wherein the L is one or more kinds selected from the group consisting of a bond, a substituted or unsubstituted alkylene having 1 to 8 carbon atoms, a substituted or unsubstituted alkenyl group having 2 to 6 carbon atoms, a substituted or unsubstituted ethylene oxide group having 2 to 6 carbon atoms, a substituted or unsubstituted ethylene amine group having 2 to 6 carbon atoms, a substituted or unsubstituted alkoxy group having 1 to 6 carbon atoms, a substituted or unsubstituted aryl or aryloxy group having 6 to 10 carbon atoms, or a substituted or unsubstituted heteroaryl group or heteroaryloxy group having 5 to 12 carbon atoms.

5. The organic electron-transfer mediator according to claim 1, wherein the -L-R is one selected from the following structures:

H, —$CH_2CH_2CH_2SO_3H$,

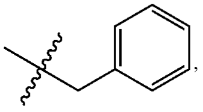

—$CH_2CH_2CH_2CH_2CH_2$—NH(Boc), —$CH_2CH_2CH_2CH_2CH_2CH_2$—NH(Boc), —$CH_2CH_2$—OH, —$CH_2CH_2$—Cl, —$CH_2CH_2CH_2CH_2CH_2$—OH, —$CH_2CH_2OCH_2CH_2$—OH,

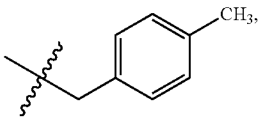

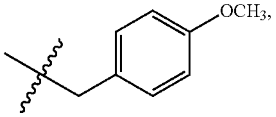

-continued

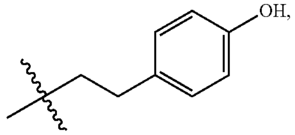

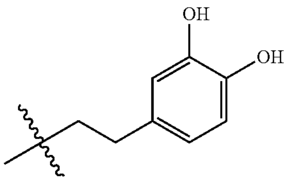

and —$CH_2$—CH═$CH_2$.

6. The organic electron-transfer mediator according to claim 1, wherein the organic electron-transfer mediator having the structure of Chemical formula 1 is represented by any one structure of the following Chemical formulas 2 to 17:

[Chemical formula 2]

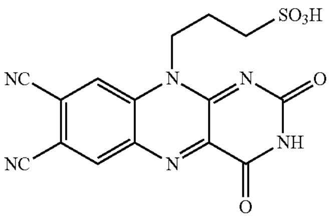

[Chemical formula 3]

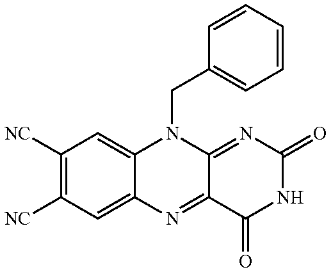

[Chemical formula 4]

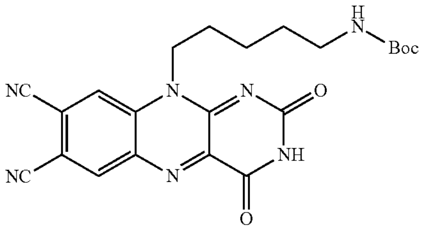

[Chemical formula 5]

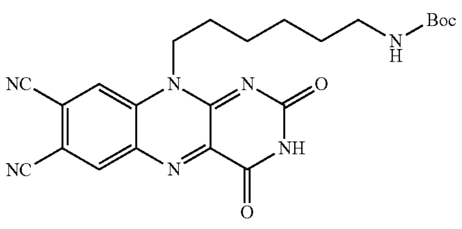

-continued
[Chemical formula 6]
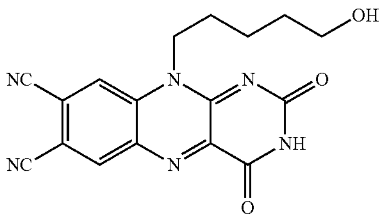
[Chemical formula 7]
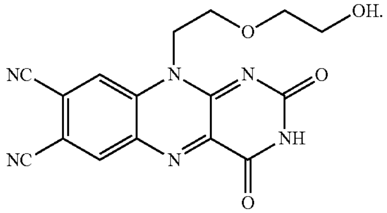
[Chemical formula 8]
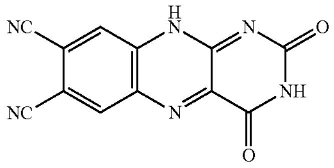
[Chemical formula 9]
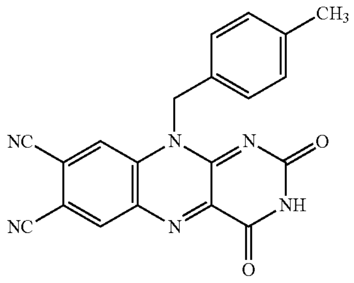
[Chemical formula 10]
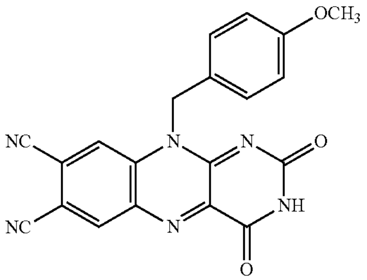
[Chemical formula 11]
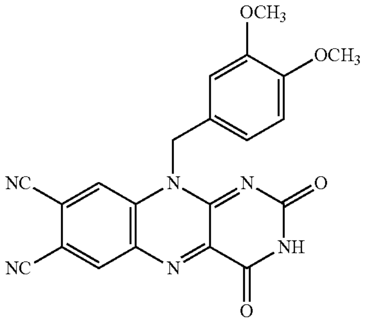
-continued
[Chemical formula 12]
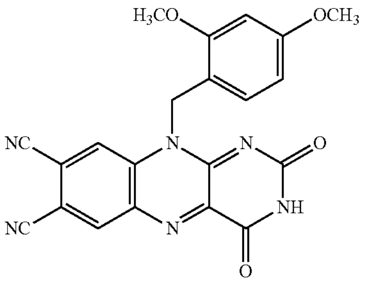
[Chemical formula 13]
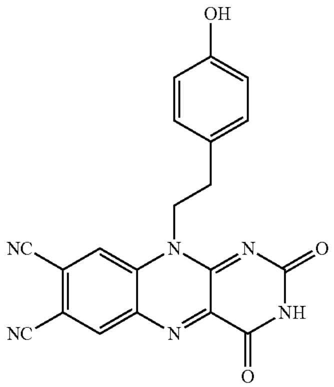
[Chemical formula 14]
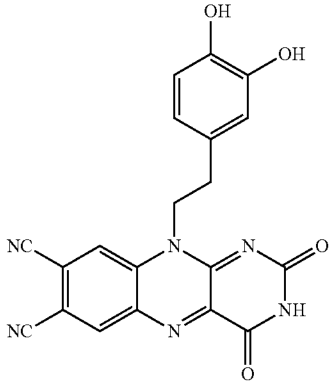
[Chemical formula 15]
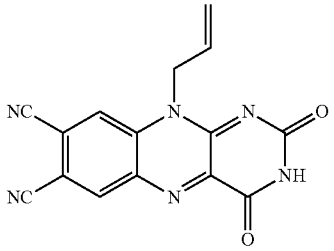
[Chemical formula 16]
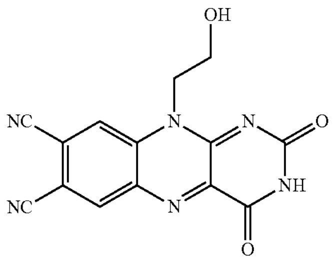

-continued

[Chemical formula 17]

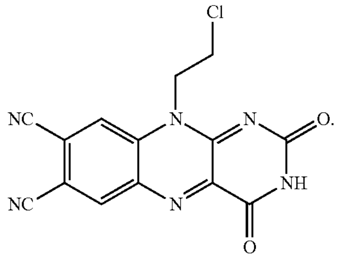

7. A method for preparation of an organic electron-transfer mediator of Chemical formula 2 below comprising i) reacting the compound of Chemical formula 18 below with 1,3-propanesultone to obtain the compound of Chemical formula 19 below; and ii) reacting the compound of Chemical formula 19 obtained in the i) with alloxan monohydrate and boric acid to obtain the compound of Chemical formula 2 below.

[Chemical formula 18]

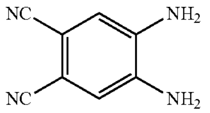

[Chemical formula 19]

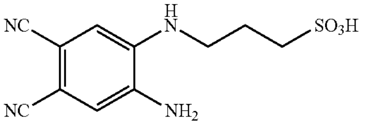

[Chemical formula 2]

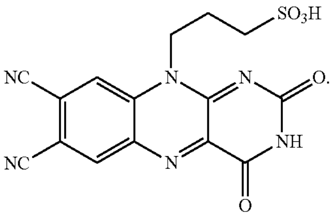

8. The method for preparation according to claim 7, wherein the amount of the 1,3-propanesultone used is 1.0 to 2.0 equivalents based on the compound of Chemical formula 18, and the amount of the alloxan monohydrate used is 1.0 to 1.5 equivalents based on the compound of Chemical formula 19.

9. The method for preparation according to claim 7, wherein the reaction temperature is 50 to 120° C. and the reaction time is 2 days to 4 days in the i), and the reaction temperature is 30 to 80° C. and the reaction time is 2 hours or more in the ii).

10. A method for preparation of an organic electron-transfer mediator according to Chemical formula 1 comprising, i) reacting 1,2-dibromo-4,5-difluorobenzene of Chemical formula 20 below with polymethylhydrosiloxane, and then reacting with Zn(CN)2 under tris(dibenzylideneacetone)dipalladium(0) {Pd2(dba)3} and 1,1'-bis(diphenylphosphino)ferrocene (DPPF) to obtain the compound of Chemical formula 21 below;

ii) reacting the compound of Chemical formula 21 obtained in the i) with ammonia water to obtain the compound of Chemical formula 22;

iii) reacting the compound of Chemical formula 22 obtained in the ii) with the compound of Chemical formula 23 to obtain the compound of Chemical formula 24; and iv) reacting the compound of Chemical formula 24 obtained in the iii) with alloxan monohydrate and boric acid to obtain the compound of Chemical formula 1:

[Chemical formula 20]

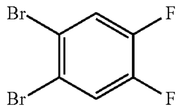

[Chemical formula 21]

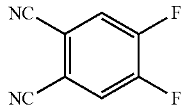

[Chemical formula 22]

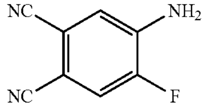

[Chemical formula 23]

$H_2N—L—R$

[Chemical formula 24]

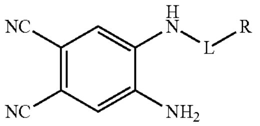

[Chemical formula 1]

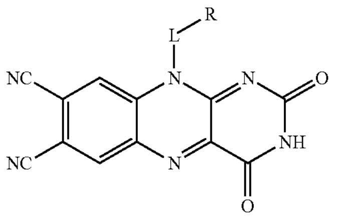

in the formulas, L and R are same as defined in claim 1.

11. An oxidation-reduction polymer, comprising the organic electron-transfer mediator according to any one claim of claim 1 to claim 6, and a polymer backbone selected from the group consisting of poly(vinylpyridine) (PVP), poly(vinylimidazole) (PVI) and poly allyl glycidyl ether (PAGE).

12. The oxidation-reduction polymer according to claim 11, b represented by Chemical formula 25:

[Chemical formula 25]

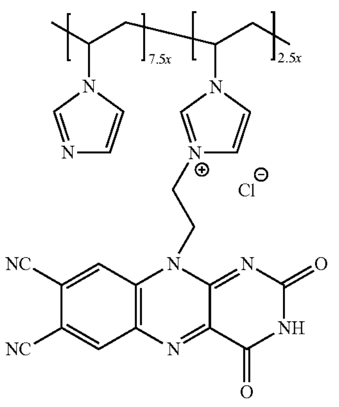

in the formula, X is 5 to 30.

13. A device comprising the organic electron-transfer mediator according to claim 1.

14. The device according to claim 13, wherein the device is an electrochemical biosensor.

15. The device according to claim 13, wherein the device is insertable.

16. A sensing layer for an electrochemical biosensor comprising an enzyme capable of conducting oxidation reduction for a liquid biological sample; and the organic electron-transfer mediator according to claim 1.

17. The sensing layer according to claim 16, wherein the enzyme comprises one or more kinds of oxidoreductases selected from the group consisting of dehydrogenase, oxidase and esterase; or one or more kinds of oxidoreductases selected from the group consisting of dehydrogenase, oxidase and esterase, and one or more kinds of cofactors selected from the group consisting of flavin adenine dinucleotide (FAD), nicotinamide adenine dinucleotide (NAD), and pyrroloquinoline quinone (PQQ).

* * * * *